US011155839B2

(12) United States Patent
Liu et al.

(10) Patent No.: US 11,155,839 B2
(45) Date of Patent: Oct. 26, 2021

(54) RECOMBINANT BACTERIA FOR PRODUCING 3-HYDROXY PROPIONIC ACID, PREPARATION METHOD THEREFOR, AND APPLICATIONS THEREOF

(71) Applicant: Institute of Microbiology, Chinese Academy of Sciences, Beijing (CN)

(72) Inventors: Weifeng Liu, Beijing (CN); Bo Liu, Beijing (CN); Qianqian Cui, Beijing (CN); Guang Zhao, Shandong (CN); Yong Tao, Beijing (CN)

(73) Assignee: INSTITUTE OF MICROBIOLOGY, CHINESE ACADEMY OF SCIENCES, Beijing (CN)

( * ) Notice: Subject to any disclaimer, the term of this patent is extended or adjusted under 35 U.S.C. 154(b) by 93 days.

(21) Appl. No.: 16/604,854

(22) PCT Filed: Apr. 12, 2018

(86) PCT No.: PCT/CN2018/082736
§ 371 (c)(1),
(2) Date: Nov. 8, 2019

(87) PCT Pub. No.: WO2018/188617
PCT Pub. Date: Oct. 18, 2018

(65) Prior Publication Data
US 2020/0157584 A1    May 21, 2020

(30) Foreign Application Priority Data
Apr. 14, 2017    (CN) .......................... 201710247568.7

(51) Int. Cl.
| | | |
|---|---|---|
| *C12N 15/70* | (2006.01) | |
| *C12P 7/52* | (2006.01) | |
| *C12N 9/02* | (2006.01) | |
| *C12N 9/10* | (2006.01) | |
| *C12N 15/74* | (2006.01) | |
| *C12N 1/20* | (2006.01) | |
| *C12R 1/19* | (2006.01) | |

(52) U.S. Cl.
CPC ............... *C12P 7/52* (2013.01); *C12N 1/205* (2021.05); *C12N 9/0008* (2013.01); *C12N 9/1029* (2013.01); *C12N 15/70* (2013.01); *C12N 15/74* (2013.01); *C12R 2001/19* (2021.05); *C12Y 102/01075* (2013.01); *C12Y 203/01041* (2013.01); *C12Y 203/01179* (2013.01); *C12Y 604/01002* (2013.01)

(58) Field of Classification Search
CPC ........... C12P 7/52; C12N 15/70; C12N 15/67; C12N 9/1029; C12Y 102/01075
See application file for complete search history.

(56) References Cited

FOREIGN PATENT DOCUMENTS

| CN | 102695799 A | 9/2012 |
|---|---|---|
| CN | 103497922 A | 1/2014 |
| CN | 103898034 A | 7/2014 |
| CN | 105189757 A | 12/2015 |

OTHER PUBLICATIONS

PCT/CN2018/082736 , Written opinion (English Translation), dated Jun. 28, 2018 (Year: 2018).*
International Search Report dated Jun. 28, 2018 in PCT/CN2018/082736.
Yang P, et al. "Biosynthesis of poly(3-hydroxypropionate) and its copolymers" (in Chinese). Chin Sci Bull (Chin Ver), 2014, 59: 2137-2144.

* cited by examiner

*Primary Examiner* — Tekchand Saidha
(74) *Attorney, Agent, or Firm* — Knobbe, Martens, Olson & Bear, LLP

(57) ABSTRACT

Provided is a method for construction of recombinant bacteria for producing 3-hydroxypropionic acid. The method includes: knocking out fadR, fabF and fabH genes of recipient bacteria, introducing acc genes or gene clusters, alKL and Mcr genes, and enhancing the expression of fadL, fadD, sthA genes and atoSC gene clusters in the recipient bacteria. Also provided is a method for producing 3-hydroxypropionic acid by using the recombinant bacteria.

19 Claims, 1 Drawing Sheet
Specification includes a Sequence Listing.

RECOMBINANT BACTERIA FOR PRODUCING 3-HYDROXY PROPIONIC ACID, PREPARATION METHOD THEREFOR, AND APPLICATIONS THEREOF

TECHNICAL FIELD

The invention relates to recombinant bacteria for producing 3-hydroxypropionic acid, a preparation method therefor, and applications thereof in the technical field of biology.

BACKGROUND ART

The manufacture of chemicals based on utilization of fossil resources faces increasing problems such as resource depletion and environmental pollution. The low-cost manufacture of traditional chemicals with biosynthetic routes has become a promising alternative. Through genetic modification of industrial microbial strains, the utilization of raw materials by microbial cells may be improved, and the conversion rate of products may be improved, thereby reducing production costs.

3-hydroxypropionic acid is an important chemical intermediate and platform compound with broad market prospects. It is also one of the 12 most promising bio-based chemical products in the world, listed by the U.S. Department of Energy in 2004. 3-hydroxypropionic acid not only may be used as an additive or preservative for food or feed, but also may synthesize various important chemicals, including acrylic acid, malonic acid, 1,3 propanediol, acrylamide, poly-3-hydroxypropionic acid and the like, through oxidation, dehydration, reduction, esterification, polymerization and other reactions.

Current methods for producing 3-hydroxypropionic acid mainly include chemical synthesis methods and biosynthesis methods. The chemical methods for preparing 3-hydroxypropionic acid include a 3-hydroxynitrile hydrolysis method, a hydrated acrylic acid method, a 3-hydroxypropanal oxidation method, an allyl alcohol oxidation method, and the like. The biological synthesis method of 3-hydroxypropionic acid mainly uses microbial fermentation to convert raw materials into 3-hydroxypropionic acid, or extracts related enzyme to produce 3-hydroxypropionic acid in a cell-free system. The research on microbial synthesis of 3-hydroxypropionic acid mainly includes three aspects: (1) screening and mutagenizing microbial strains that naturally synthesize 3-hydroxypropionic acid; (2) constructing a recombinant microbial engineering strain to produce 3-hydroxypropionic acid using glucose; and (3) constructing a microbial engineering strain to produce 3-hydroxypropionic acid using glycerol.

The screening and mutagenesis of microorganisms that naturally synthesize 3-hydroxypropionic acid are mainly concentrated in *Candida*, but because the synthesis of 3-hydroxypropionic acid by *Candida* usually requires propionic acid as a carbon source, the economic feasibility is poor.

Construction of the recombinant microbial engineering strains for synthesizing 3-hydroxypropionic acid using glucose as a substrate mainly includes *Escherichia coli*, *Corynebacterium glutamicum* and the like. The synthesis of 3-hydroxypropionic acid by engineering strains mainly utilizes two types of synthetic pathways: (1) a synthetic pathway via 3-hydroxypropionyl-CoA; and (2) a synthetic pathway via malonyl-CoA. Cargill Corporation, USA converts glucose to lactic acid using an engineering strain such as *Escherichia coli* based on the 3-hydroxypropionyl-CoA pathway, and then produces the 3-hydroxypropionic acid by a three-step reaction including catalysis by propionyl-CoA transferase, lactyl-CoA dehydratase, and 3-hydroxypropionyl hydrolase. OPXBIO Inc., USA utilizes the malonyl-CoA pathway to convert a substrate to 3-hydroxypropionic acid by catalysis of acetyl-CoA carboxylase and malonyl-CoA reductase.

Construction of recombinant microbial engineering strains for the synthesis of 3-hydroxypropionic acid using glycerol as a substrate is carried out by oxidizing 3-hydroxypropionaldehyde into 3-hydroxypropionic acid mainly by introducing aldehyde oxidase in *Klebsiella pneumoniae* or *Escherichia coli*.

At present, the main technical limitation of biosynthesis of 3-hydroxypropionic acid is that the raw material price is relatively high, and the theoretical conversion rate of the adopted pathway is low, and a new low-cost raw material rout urgently needs to be developed. Fatty acids are a kind of substance with high degree of reduction. The fatty acid raw materials used for microbial fermentation and biotransformation may be obtained at low prices from sources such as crude oil processing products and waste oil.

SUMMARY

The technical problem to be solved by the present invention is how to produce 3-hydroxypropionic acid.

In order to solve the above technical problem, the present invention provides a construction method of recombinant bacteria at first.

The construction method of the recombinant bacteria provided by the present invention includes: modifying recipient bacteria by A or B to obtain the recombinant bacteria; the A being A6; the B being A6 and all or part of A1, A2, A3, A4, A5, A7 and A8;

A1. knocking out a fatty acid degradation transcription factor fadR gene of the recipient bacteria or inhibiting expression of the fadR gene or inhibiting activity of a protein encoded by the fadR gene;

A2. knocking out a β-ketoacyl-ACP synthase II gene fabF gene of the recipient bacteria or inhibiting expression of the fabF gene or inhibiting activity of a protein encoded by the fabF gene;

A3. knocking out a β-ketoacyl-ACP synthase III gene fabH gene of the recipient bacteria or inhibiting expression of the fabH gene or inhibiting activity of a protein encoded by the fabH gene;

A4. increasing content of a protein encoded by an acetyl-CoA carboxylase acc gene or gene cluster in the recipient bacteria or/and enhancing activity of the protein encoded by the acc gene or gene cluster;

A5. increasing content of a protein encoded by an exogenous alkane uptake outer membrane protein gene alkL gene in the recipient bacteria or/and enhancing activity of the protein encoded by the alkL gene; and A6. increasing content of a protein encoded by a malonyl-CoA reductase gene mcr gene in the recipient bacteria or/and enhancing activity of the protein encoded by the mcr gene;

the recipient bacteria being bacteria or fungi containing the fadR gene, the fabF gene, and the fabH gene.

In the above method, the recipient bacteria may be 1) or 2):

1) *Escherichia coli*; and
2) *Escherichia coli* BW25113.

In the above method, the acc gene or gene cluster may be derived from *Corynebacterium glutamicum* or/and *Rhodococcus opacus*.

The alkL gene may be derived from *Marinobacter hydrocarbonoclasticus* or/and *Pseudomonas putida*.

The mcr gene may be derived from *Chloroflexus aurantiacus*.

In the above method, the fadR gene may encode a protein of the following a1) or a2):

a1) a protein shown in SEQ ID No. 2 in a sequence listing; and a2) a protein having 75% or higher identity with an amino acid sequence of SEQ ID No. 2 and having a same function, obtained by substitution and/or deletion and/or addition of one or more amino acid residues in the amino acid sequence of SEQ ID No. 2 in the sequence listing.

The fabF gene may encode a protein of the following a3) or a4):

a3) a protein shown in SEQ ID No. 14 in the sequence listing;

a4) a protein having 75% or higher identity with an amino acid sequence of SEQ ID No. 14 and having a same function, obtained by substitution and/or deletion and/or addition of one or more amino acid residues in the amino acid sequence of SEQ ID No. 14 in the sequence listing.

The fabH gene may encode a protein of the following a5) or a6):

a5) a protein shown in SEQ ID No. 16 in the sequence listing;

a6) a protein having 75% or higher identity with an amino acid sequence of SEQ ID No. 16 and having a same function, obtained by substitution and/or deletion and/or addition of one or more amino acid residues in the amino acid sequence of SEQ ID No. 16 in the sequence listing.

The acc gene or gene cluster may encode proteins of a7) and a8):

a7) the following a71) or a72):

a71) a protein shown in SEQ ID No. 26 in the sequence listing; and a72) a protein having 75% or higher identity with an amino acid sequence of SEQ ID No. 26 and having a same function, obtained by substitution and/or deletion and/or addition of one or more amino acid residues in the amino acid sequence of SEQ ID No. 26 in the sequence listing; and a8) the following a81) or a82):

a81) a protein shown in SEQ ID No. 27 in the sequence listing; and a82) a protein having 75% or higher identity with an amino acid sequence of SEQ ID No. 27 and having a same function, obtained by substitution and/or deletion and/or addition of one or more amino acid residues in the amino acid sequence of SEQ ID No. 27 in the sequence listing.

The alkL gene may encode a protein of the following a9) or a10):

a9) a protein shown in SEQ ID No. 29 in the sequence listing; and a10) a protein having 75% or higher identity with an amino acid sequence of SEQ ID No. 29 and having a same function, obtained by substitution and/or deletion and/or addition of one or more amino acid residues in the amino acid sequence of SEQ ID No. 29 in the sequence listing.

The mcr gene may encode a protein of the following a11) or a12):

a11) a protein shown in SEQ ID No. 37 in the sequence listing; and a12) a protein having 75% or higher identity with an amino acid sequence of SEQ ID No. 37 and having a same function, obtained by substitution and/or deletion and/or addition of one or more amino acid residues in the amino acid sequence of SEQ ID No. 37 in the sequence listing.

In the above method, A4 may be achieved by introducing the acc gene or gene cluster into the recipient bacteria.

A5 may be achieved by introducing the alkL gene into the recipient bacteria.

A6 may be achieved by introducing the mcr gene into the recipient bacteria.

In the above method, introducing the acc gene or gene cluster into the recipient bacteria may specifically be introducing an expression vector (i.e., an acc gene or a gene cluster expression vector) containing the acc gene or gene cluster into the recipient bacteria.

Introducing the alkL gene into the recipient bacteria may specifically be introducing an expression vector (i.e., an alkL gene expression vector) containing the alkL gene into the recipient bacteria.

Introducing the mcr gene into the recipient bacteria may specifically be introducing an expression vector (i.e., an mcr gene expression vector) containing the mcr gene into the recipient bacteria.

The expression vector may be a plasmid, a cosmid, a phage or a viral vector. The plasmid may specifically be pSB1s or pXB1k, the sequence of the pSB1s is SEQ ID No. 30 in the sequence listing, and the sequence of the pXB1k is SEQ ID No. 35 in the sequence listing.

When the acc gene or gene cluster, the alkL gene and/or the mcr gene are introduced into the recipient bacteria, a single expression vector may be introduced, or a co-expression vector may be introduced. The single expression vector contains only one of the acc gene or gene cluster, the alkL gene, and the mcr gene. The co-expression vector contains at least two of the acc gene or gene cluster, the alkL gene, and the mcr gene.

In an example of the present invention, introduction of the acc gene or gene cluster and the alkL gene into the recipient bacteria is realized by introducing a co-expression vector (i.e., an acc-alkL co-expression vector) containing the two genes or gene clusters into the recipient bacteria, and introduction of the mcr gene into the recipient bacteria is realized by introducing a single expression vector (i.e., an mcr expression vector) containing the gene into the recipient bacteria. The acc-alkL co-expression vector may specifically be a recombinant vector pSB1s-acc-alkL obtained by introducing the acc gene or gene cluster and the alkL gene into the pSB1s. The pSB1s-acc-alkL may express the accBC protein shown in SEQ ID No. 26, the accDA protein shown in SEQ ID No. 27, and the alkL protein shown in SEQ ID No. 29. The mcr expression vector may specifically be a recombinant vector pXB1k-mcr obtained by introducing the mcr gene into the pXB1k. The pXB1k-mcr may express the mcr protein shown in SEQ ID No. 37.

In the above method, the fadR gene may be the following b1) or b2):

b1) a cDNA molecule or DNA molecule shown in SEQ ID No. 1 in the sequence listing; and b2) a cDNA molecule or genomic DNA molecule having 75% or higher identity with a nucleotide sequence defined by b1) and having a same function.

The fabF gene may be the following b3) or b4):

b3) a cDNA molecule or DNA molecule shown in SEQ ID No. 13 in the sequence listing; and b4) a cDNA molecule or genomic DNA molecule having 75% or higher identity with a nucleotide sequence defined by b3) and having a same function.

The fabH gene may be the following b5) or b6):

b5) a cDNA molecule or DNA molecule shown in SEQ ID No. 15 in the sequence listing; and b6) a cDNA molecule or genomic DNA molecule having 75% or higher identity with a nucleotide sequence defined by b5) and having a same function.

The acc gene or gene cluster may be the following b7) or b8):

b7) a cDNA molecule or DNA molecule shown in positions 15-3259 of SEQ ID No. 25 in the sequence listing; and b8) a cDNA molecule or genomic DNA molecule having 75% or higher identity with a nucleotide sequence defined by b7) and having a same function.

The alkL gene may be the following b9) or b10):

b9) a cDNA molecule or DNA molecule shown in SEQ ID No. 28 in the sequence listing; and b10) a cDNA molecule or genomic DNA molecule having 75% or higher identity with a nucleotide sequence defined by b9) and having a same function.

The mcr gene may be the following b11) or b12):

b11) a cDNA molecule or DNA molecule shown in SEQ ID No. 36 in the sequence listing; and b12) a cDNA molecule or genomic DNA molecule having 75% or higher identity with a nucleotide sequence defined by b11) and having a same function.

In the above method, knockout of the fatty acid degrading transcription factor fadR gene of the recipient bacteria in A1 may be carried out by homologous recombination, and specifically, an *Escherichia coli* strain JW1176 having a fadR gene knockout trait may be used.

Knockout of the β-ketoacyl-ACP synthase II gene fabF gene of the recipient bacteria in A2 may be carried out by homologous recombination, and specifically, an *Escherichia coli* strain JW1081 having a fabF gene knockout trait may be used.

Knockout of the β-ketoacyl-ACP synthase III gene fabH gene of the recipient bacteria in A3 may be carried out by homologous recombination, and specifically, an *Escherichia coli* strain JW1077 having a fabH gene knockout trait may be used.

The above method may further include four, any three, any two or any one of the following B1-B4:

B1. increasing content of a protein encoded by a fadL gene in the recipient bacteria or/and enhancing activity of the protein encoded by the fadL gene;

B2. increasing content of a protein encoded by a gene in a fatty acid β oxidation pathway in the recipient bacteria or/and enhancing activity of the protein encoded by the gene in the fatty acid β oxidation pathway;

the gene in the fatty acid β oxidation pathway being selected from one or more of the following genes: a fadD gene encoding fatty acyl-CoA synthase, a fadE gene encoding fatty acyl-CoA dehydrogenase, a fadB gene encoding 3-hydroxyacyl-CoA dehydrogenase, a fadA gene encoding 3-ketoacyl-CoA thiolase, a fadI gene encoding 3-ketoacyl-CoA thiolase, a fadJ gene encoding 3-hydroxyacyl-CoA dehydrogenase and a fadK gene encoding short-chain fatty acyl-CoA synthase;

B3. increasing content of a protein encoded by a sthA gene in the recipient bacteria or/and enhancing activity of the protein encoded by the sthA gene; and B4. increasing content of a protein encoded by a gene in a short-chain fatty acid degradation pathway in the recipient bacteria or/and enhancing activity of the protein encoded by the gene in the short-chain fatty acid degradation pathway.

The gene in the short-chain fatty acid degradation pathway is B4a or B4b:

B4a. a gene in a short-chain fatty acid degradation regulatory gene cluster atoSC gene cluster; and B4b. a gene in a short-chain fatty acid degradation gene cluster atoDAEB gene cluster.

In the above method, the recipient bacteria may further contain the fadL gene, the gene in the fatty acid β oxidation pathway, the sthA gene, and/or the gene in the short-chain fatty acid degradation pathway.

In the above method, the gene in the short-chain fatty acid degradation regulatory gene cluster atoSC gene cluster may be a gene atoC gene encoding an atoC transcription activator and/or a gene atoS gene encoding atoS-sensing histidine kinase.

The gene in the short-chain fatty acid degradation gene cluster atoDAEB gene cluster may be a gene atoA gene encoding an acetoacetyl-CoA transferase α subunit, a gene atoD gene encoding an acetoacetyl-CoA transferase β subunit, a gene atoE gene encoding an acetoacetic acid transport protein, and/or a gene atoB gene encoding an acetyl-CoA acetyltransferase.

In the above method, the fadL gene may encode a protein of the following a17) or a18):

a17) a protein shown in SEQ ID No. 6 in the sequence listing; and a18) a protein having 75% or higher identity with an amino acid sequence of SEQ ID No. 6 and having a same function, obtained by substitution and/or deletion and/or addition of one or more amino acid residues in the amino acid sequence of SEQ ID No. 6 in the sequence listing.

The fadD gene may encode a protein of the following a19) or a20):

a19) a protein shown in SEQ ID No. 9 in the sequence listing; and a20) a protein having 75% or higher identity with an amino acid sequence of SEQ ID No. 9 and having a same function, obtained by substitution and/or deletion and/or addition of one or more amino acid residues in the amino acid sequence of SEQ ID No. 9 in the sequence listing.

The sthA gene may encode a protein of the following a21) or a22):

a21) a protein shown in SEQ ID No. 12 in the sequence listing; and a22) a protein having 75% or higher identity with an amino acid sequence of SEQ ID No. 12 and having a same function, obtained by substitution and/or deletion and/or addition of one or more amino acid residues in the amino acid sequence of SEQ ID No. 12 in the sequence listing.

The atoSC gene cluster may encode proteins of the following a23) and a24):

a23) a protein of the following a231) or a232):

a231) a protein shown in SEQ ID No. 19 in the sequence listing; and a232) a protein having 75% or higher identity with an amino acid sequence of SEQ ID No. 19 and having a same function, obtained by substitution and/or deletion and/or addition of one or more amino acid residues in the amino acid sequence of SEQ ID No. 19 in the sequence listing; and a24) a protein of the following a241) or a242):

a241) a protein shown in SEQ ID No. 21 in the sequence listing; and a242) a protein having 75% or higher identity with an amino acid sequence of SEQ ID No. 21 and having a same function, obtained by substitution and/or deletion and/or addition of one or more amino acid residues in the amino acid sequence of SEQ ID No. 21 in the sequence listing.

In the above method, B1 may be achieved by substituting a promoter $P_{CPA1}$ for a promoter of the fadL gene.

B2 may be achieved by substituting the promoter $P_{CPA1}$ for a promoter of the gene in the fatty acid β oxidation pathway.

B3 may be achieved by substituting the promoter $P_{CPA1}$ for a promoter of the sthA gene.

B4 may be achieved by substituting the promoter $P_{CPA1}$ for a promoter of the gene in the short-chain fatty acid degradation pathway.

In the above method, the promoter of the gene in the short-chain fatty acid degradation pathway may be a promoter of the short-chain fatty acid degradation regulatory gene cluster or a promoter of the short-chain fatty acid degradation gene cluster atoDAEB gene cluster.

In the above method, the promoter $P_{CPA1}$ may be a nucleic acid molecule of the following 1) or 2) or 3):

1) a DNA molecule with a coding sequence being positions 1443-1622 of SEQ ID No. 3 in the sequence listing;

2) a DNA molecule having 75% or higher identity with a nucleotide sequence defined by 1) and having a same function; and 3) a DNA molecule hybridizing to the nucleotide sequence defined by 1) under a stringent condition and having a same function.

In the above method, substitution of the promoter $PP_{CPA1}$ for the promoter of the fadL gene may be achieved by a DNA fragment shown in SEQ ID No. 4 in the sequence listing.

Substitution of the promoter $P_{CPA1}$ for the promoter of the gene in the fatty acid β oxidation pathway may be achieved by a DNA fragment shown in SEQ ID No. 7 in the sequence listing.

Substitution of the promoter $P_{CPA1}$ for the promoter of the sthA gene may be achieved by a DNA fragment shown in SEQ ID No. 10 in the sequence listing.

Substitution of the promoter $P_{CPA1}$ for the promoter of the gene in the short-chain fatty acid degradation pathway may be achieved by a DNA fragment shown in SEQ ID No. 17 in the sequence listing.

In the above method, the 75% or higher identity may be 75%, 80%, 85%, 90%, 91%, 92%, 93%, 94%, 95%, 96%, 97%, 98%, 99% or higher identity.

In order to solve the above technical problem, the present invention also provides a preparation method for the 3-hydroxypropionic acid.

The preparation method for the 3-hydroxypropionic acid provided by the present invention includes: bio-transforming the recombinant bacteria prepared by the preparation method of the recombinant bacteria with fatty acid as a substrate to prepare the 3-hydroxypropionic acid.

In the above preparation method for the 3-hydroxypropionic acid, the fatty acid may be palmitic acid, stearic acid, myristic acid, lauric acid, capric acid, octanoic acid and/or hexanoic acid.

The above preparation method for the 3-hydroxypropionic acid may further include inducing the recombinant bacteria with arabinose prior to the biotransformation.

The above preparation method for the 3-hydroxypropionic acid may specifically be preparation of the 3-hydroxypropionic acid by whole cell catalysis of the fatty acid by using the recombinant bacteria.

In order to solve the above technical problem, the present invention also provides any one of the following Z1-Z4 products:

Z1. recombinant bacteria prepared by the preparation method of the recombinant bacteria;

Z2. protein or a set of proteins, being the following M1 or M2:

M1. M1a and M1b, M1a being a protein encoded by the mcr gene, and M1b being all or part of a protein encoded by the acc gene or gene cluster and a protein encoded by the alkL gene; and M2. the above M1 and M2a, M2a being all or part of a protein encoded by the fadL gene, a protein encoded by the fadD gene, a protein encoded by the sthA gene, and a protein encoded by the atoSC gene cluster;

Z3. a gene or a set of genes, being the following N1 or N2:

N1. N1a and N1b, N1a being the mcr gene, and N1b being all or part of the acc gene or gene cluster and the alkL gene; and N2. the above N1 and N2a, N2a being all or part of the fadL gene, the fadD gene, the sthA gene, and the atoSC gene cluster; and Z4. a set of reagents, consisting of the promoter $P_{CPA1}$ and the gene or the set of genes.

In order to solve the above technical problem, the present invention also provides any one of the following uses of the products:

X1. producing 3-hydroxypropionic acid;

X2. preparing a product for producing a 3-hydroxypropionic acid;

X3. degrading fatty acid; and

X4. preparing a product for degrading a fatty acid.

DETAILED DESCRIPTION

Figure 1:
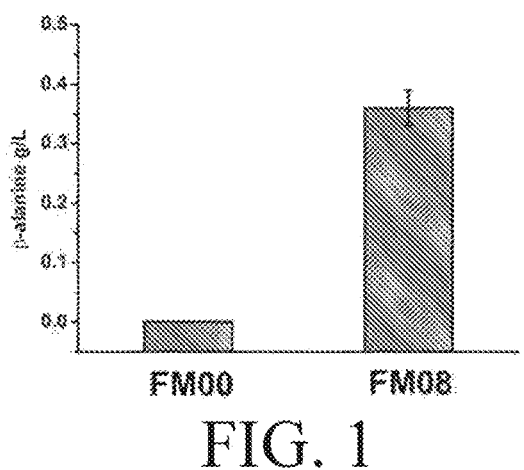
FIG. 1 shows production of β-alanine using FM08.

The present invention will be described in further detail below with embodiments, and the examples are given merely to illustrate the present invention and are not intended to limit the scope of the present invention. The experimental methods in the following examples are conventional methods unless otherwise specified. The materials, reagents, instruments and the like used in the following examples are commercially available unless otherwise specified. For the quantitative tests in the following examples, three replicate experiments are set, and the results are averaged.

The wild-type P1 phage (Thomason L C, Costantino N. 2007. *E. coli* genome manipulation by P1 transduction. *Current Protocols in Molecular Biology:* 1.17. 1-8) in the following examples is available to the public from the Institute of Microbiology, Chinese Academy of Sciences. The biomaterial is used only for repeating the relevant experiments of the present invention and cannot be used for other purposes.

In the following examples, *Escherichia coli* BW25113 (Datsenko K A, Wanner B L. One-step inactivation of chromosomal genes in *Escherichia coli* K-12 using PCR products. Proc. Natl. Acad. Sci. U.S.A. 2,000; 97(12):6640-6645) is non-pathogenic bacteria with a clear genetic background, short generation time, easy cultivation, and low-price culture medium raw materials. The *Escherichia coli* BW25113 is available to the public from the Institute of Microbiology, Chinese Academy of Sciences. The biomaterial is used only for repeating the relevant experiments of the present invention and cannot be used for other purposes.

Example 1. Construction of Recombinant *Escherichia coli* Engineering Strain FM07

In the present example, a basic strain FM07 which may be used for preparing a strain for producing β-alanine and 3-hydroxypropionic acid was prepared. A preparation method of the strain was as follows, and primers used were shown in Table 1.

(1) Knockout of Fatty Acid Degradation Transcription Factor fadR.

Starting from *Escherichia coli* BW25113, a fadR gene of *Escherichia coli* BW25113 was knocked out, and a mutant FM01 of *Escherichia coli* BW25113 was obtained. The specific steps were as follows:

(1-a) Preparation of P1 Phage Containing *Escherichia coli* Gene Fragment Having fadR Knockout Trait.

The *Escherichia coli* gene fragment having the fadR knockout trait was derived from an *Escherichia coli* strain JW1176. The strain was a W3110 series strain having the fadR knockout trait. JW1176 was a product of the National Institute of Genetics (NIG, Japan). A kanamycin resistance gene (about 1300 bp) with an FRT site at two ends was substituted for a gene fadR encoding a fatty acid degradation transcription factor to knock out the fadR gene. (Baba T, Ara T, et al. Construction of *Escherichia coli* K-12 in-frame, single-gene knockout mutants: the Keio collection. Mol. Syst. Biol. 2006; 2:2006.0008). The preparation process of the P1 phage was as follows: a JW1176 strain was cultured overnight at 37° C., and then transferred to an LB medium containing 5 mmol/L $CaCl_2$ and 0.1% glucose and cultured for 1 h at 37° C., then a wild type P1 phage was added and culture was continued for 1-3 h, a few drops of chloroform were added for further culture for a few minutes, and a supernatant was obtained by centrifuging to obtain a phage P1vir fadR containing the *Escherichia coli* gene fragment having the fadR knockout trait.

(1-b) Construction of *Escherichia coli* Strain FM01-Kan Using P1 Phage Transduction Technology:

1.5 mL of bacteria solution of *Escherichia coli* BW25113 (recipient bacteria) cultured overnight was centrifuged at 10000 g for 2 minutes, and then BW25113 bacterial cells were resuspended with 0.75 mL of P1 salt solution (containing water as a solvent and 10 mM $CaCl_2$ and 5 mM $MgSO_4$ as solutes). 100 μL of phage P1vir fadR and 100 μL of BW25113 cell suspension were mixed and incubated at 37° C. for 30 min. Then 1 mL of LB medium and 200 μL of 1 mol/L sodium citrate were added, and culture was continued at 37° C. for 1 h. The bacterial cells were collected by centrifugation. After being resuspended in 100 μL of LB medium, the bacterial cells were spread on LB plates containing kanamycin (the concentration of kanamycin was 50 μg/ml). After culturing overnight at 37° C., clones were selected. The fadR-IF/fadR-IR primer was used for PCR amplification and identification (an amplified target band of 1700 bp was positive), and positive clones were selected and named FM01-Kan.

(1-c) Elimination of Resistance:

The pCP20 plasmid (Clontech Company) was transformed into FM01-Kan by a calcium chloride transformation method, the FM01-Kan was cultured overnight at 30° C. in an LB plate containing ampicillin, and then clones were selected to obtain recombinant *Escherichia coli* FM01-Kan/pCP20 containing the plasmid pCP20. After being cultured in an LB medium containing ampicillin resistance at 30° C., the cells were spread on a non-resistant LB plate and cultured at 43° C. overnight, and clones were selected. The fadR-IF/fadR-IR primer was used for PCR amplification and identification (an amplified target band of 400 bp was positive), and positive clones were selected and named FM01.

FM01 is a strain obtained by knocking out the fatty acid degradation transcription factor fadR gene of *Escherichia coli* BW25113. In *Escherichia coli* BW25113, the fadR gene encodes the protein shown in SEQ ID No. 2, and the coding sequence of the fadR gene is shown in SEQ ID No. 1. FadR-IF/fadR-IR obtains a fragment of about 400 bp by amplification from the genomic DNA of FM01, and obtains a fragment of about 1100 bp by amplification from the genomic DNA of *Escherichia coli* BW25113. The primer binding positions of the fadR-IF and fadR-IR are the upstream region and the downstream region of the fadR gene of *Escherichia coli* BW25113, respectively. The results of sequencing analysis show that there is no fadR gene in the genome of FM01, and FM01 is a mutant of *Escherichia coli* BW25113 obtained by knocking out the fadR gene of *Escherichia coli* BW25113.

(2) Enhancement of Expression of fadL Gene by Promoter Substitution.

Starting from the recombinant bacteria FM01, an *Escherichia coli* constitutive promoter $P_{CPA1}$ was substituted for a promoter of the fadL gene in the strain, and recombinant *Escherichia coli* FM02 was obtained. The specific steps were as follows:

(2-a) Preparation of Host Bacteria Containing pKD46 Plasmid:

The pKD46 plasmid (Clontech Company) was transformed into the FM01 strain obtained in the previous step by a calcium chloride transformation method, the strain was cultured overnight at 30° C. in an LB plate containing ampicillin, and then clones were selected to obtain recombinant *Escherichia coli* FM01/pKD46 containing the plasmid pKD46. The recombinant *Escherichia coli* FM01/pKD46 expressed three recombinant proteins of λ phage after arabinose induction, and the host bacteria had the ability of homologous recombination. FM01/pKD46 competent cells were then prepared by washing with 10% glycerol.

(2-b) Preparation of Plasmid for Amplifying Targeting Gene Fragment of Substitution Promoter:

The nucleotide sequence of a CPA1-Lox66-Kan-Lox71 fragment was shown in SEQ ID No. 3. CPA1-Lox66-Kan-Lox71 contained: A. a constitutive promoter $P_{CPA1}$ sequence, the nucleotide sequence of which was positions 1443-1622 of SEQ ID No. 3, and B. a kanamycin resistance gene (LOXP-kan-LOXP) flanked by LOXP, the nucleotide sequence of which was positions 21-1433 of SEQ ID No. 3. The CPA1-Lox66-Kan-Lox71 sequence was ligated to a pUC57 vector by whole gene synthesis (Nanjing Genscript Biotechnology Co., Ltd.) to obtain a recombinant vector pUC57-9K.

(2-c) Preparation of Targeting Fragment fadLup-Kan-$P_{CPA1}$-fadLdown:

Using pUC57-9K as a template, a fadLup-kan-$P_{CPA1}$-fadLdown fragment was amplified using a primer fadL-PF/fadL-PR. The sequence of the fadLup-kan-$P_{CPA1}$-fadLdown fragment was SEQ ID No. 4 in the sequence listing, and the fragment contains (a) a promoter upstream homologous arm fadLup of the fadL gene, the nucleotide sequence of which was positions 1-51 of SEQ ID No. 4; (b) a kanamycin resistance gene (LOXP-kan-LOXP) flanked by LOXP, the nucleotide sequence of which was positions 52-1492 of SEQ ID No. 4; (c) an *Escherichia coli* constitutive promoter $P_{CPA1}$, the nucleotide sequence of which was positions 1493-1670 of SEQ ID No. 4; and (d) a promoter downstream homologous arm fadLdown of the fadL gene, the nucleotide sequence of which was positions 1671-1722 of SEQ ID No. 4.

(2-d) Homologous Recombination:

The above fadLup-kan-$P_{CP41}$-fadLdown fragment was electroporated into the FM01/pKD46 competent cells prepared in (2-a), the cells were placed in an LB plate containing kanamycin (concentration: 50 μg/ml) overnight at 37° C., and clones were selected. A fadL-PIF/fadL-PIR primer was used for PCR amplification and identification (an amplified target band of about 2,000 bp was positive, and an amplified target band of about 400 bp was negative), and positive clones were selected and named FM02-kan. The primer binding positions were the upstream and downstream regions of the promoter of the fadL gene of Escherichia coli BW25113, respectively. The results of sequencing analysis indicate that an FM02-kan genome contains the fadLup-kan-$P_{CP41}$-fadLdown fragment of the step (2-c).

(2-e) Elimination of Resistance:

The pCP20 plasmid (Clontech Company) was transformed into FM02-Kan by a calcium chloride transformation method, the FM02-Kan was cultured overnight at 30° C. in an LB plate containing ampicillin, and then clones were selected to obtain recombinant Escherichia coli FM02-Kan/pCP20 containing the plasmid pCP20. After being cultured in an LB medium containing ampicillin resistance at 30° C., the cells were spread on a non-resistant LB plate and cultured at 43° C. overnight, and clones were selected. The fadL-PIF/fadL-PIR primer was used for PCR amplification and identification (an amplified target band of about 600 bp was positive, and an amplified target band of about 2,000 bp or 400 bp was negative), and positive clones were selected and named FM02.

FM02 is a strain obtained by substituting the constitutive promoter $P_{CP41}$ for a promoter of a fadL gene of FM01. In FM01, the fadL gene encodes the protein shown in SEQ ID No. 6, and the coding sequence of the fadL gene is shown in SEQ ID No. 5. The results of sequencing analysis indicate that the constitutive promoter $P_{CP41}$ is substituted for the fadL gene promoter on the genome of FM02, and expression of the fadL gene is initiated by $P_{CP41}$.

(3) Enhancement of Expression of fadD Gene by Promoter Substitution.

Starting from the recombinant bacteria FM02, the Escherichia coli constitutive promoter $P_{CP41}$ was substituted for a promoter of a fatty acyl-CoA synthase fadD gene in the strain, and recombinant Escherichia coli FM03 was obtained. The specific steps were as follows:

(3-a) Preparation of host bacteria containing pKD46 plasmid:

The pKD46 plasmid was transformed into the FM02 strain obtained in the previous step according to the method of the step (2) to obtain recombinant Escherichia coli FM02/pKD46 containing the plasmid pKD46, and then FM02/pKD46 competent cells were prepared.

(3-b) Preparation of Targeting Fragment fadDup-Kan-$P_{CP41}$-fadDdown:

Using pUC57-9K of the step (2) as a template, a fadD-kan-$P_{CP41}$-fadDdown fragment was amplified using a primer fadD-PF/fadD-PR. The sequence of the fadDup-kan-$P_{CP41}$-fadDdown fragment was SEQ ID No. 7 in the sequence listing, and the fragment contained (a) a promoter upstream homologous arm fadDup of the fadD gene, the nucleotide sequence of which was positions 1-51 of SEQ ID No. 7; (b) a kanamycin resistance gene (LOXP-kan-LOXP) flanked by LOXP, the nucleotide sequence of which was positions 52-1492 of SEQ ID No. 7; (c) an Escherichia coli constitutive promoter $P_{CP41}$, the nucleotide sequence of which was positions 1493-1670 of SEQ ID No. 7; and (d) a promoter downstream homologous arm fadDdown of the fadD gene, the nucleotide sequence of which was positions 1671-1722 of SEQ ID No. 7.

(3-c) Homologous Recombination:

The above fadDup-kan-$P_{CP41}$-fadDdown fragment was electroporated into the FM02/pKD46 competent cells prepared in (3-a), the cells were placed in an LB plate containing kanamycin (concentration: 50 μg/ml) overnight at 37° C., and clones were selected. A fadD-PIF/fadD-PIR primer was used for PCR amplification and identification (an amplified target band of 2,000 bp was positive, and an amplified target band of about 400 bp in length was negative), and positive clones were selected and named FM03-kan. The primer binding positions were the upstream and downstream regions of the promoter of the fadD gene of Escherichia coli BW25113, respectively. The results of sequencing analysis indicate that an FM03-kan genome contains the fadDup-kan-$P_{CP41}$-fadDdown fragment of the step (3-b).

(3-d) Elimination of Resistance:

The kanamycin resistance of FM03-kan was eliminated using the pCP20 plasmid according to the method of the step (2). The fadD-PIF/fadD-PIR primer was used for PCR amplification and identification (an amplified target band of about 600 bp was positive, and an amplified target band of about 2,000 bp or 400 bp was negative), and positive clones were selected and named FM03.

FM03 is a strain obtained by substituting the constitutive promoter $P_{CP41}$ for the promoter of the fadD gene of FM02. In FM02, the fadD gene encodes the protein shown in SEQ ID No. 9, and the coding sequence of the fadD gene is shown in SEQ ID No. 8. The results of sequencing analysis indicate that the constitutive promoter $P_{CP41}$ is substituted for the fadD gene promoter on the genome of FM03, and the expression of the fadD gene is initiated by $P_{CP41}$.

(4) Enhancement of Expression of sthA Gene by Promoter Substitution.

Starting from the recombinant bacteria FM03, the Escherichia coli constitutive promoter $P_{CP41}$ was substituted for a promoter of a fatty acyl-CoA synthase sthA gene in the strain, and recombinant Escherichia coli FM04 was obtained. The specific steps were as follows:

(4-a) Preparation of Host Bacteria Containing pKD46 Plasmid:

The pKD46 plasmid was transformed into the FM03 strain obtained in the previous step according to the method of the step (2) to obtain recombinant Escherichia coli FM03/pKD46 containing the plasmid pKD46, and then FM03/pKD46 competent cells were prepared.

(4-b) Preparation of Targeting Fragment sthAup-Kan-$P_{CP41}$-sthAdown:

Using pUC57-9K of the step (2) as a template, a sthAup-kan-$P_{CP41}$-sthAdown fragment was amplified using a primer sthA-PF/sthA-PR. The sequence of the sthAup-kan-$P_{CP41}$-sthAdown fragment was SEQ ID No. 10 in the sequence listing, and the fragment contained (a) a promoter upstream homologous arm fadDup of the sthA gene, the nucleotide sequence of which was positions 1-51 of SEQ ID No. 10; (b) a kanamycin resistance gene (LOXP-kan-LOXP) flanked by LOXP, the nucleotide sequence of which was positions 52-1492 of SEQ ID No. 10; (c) an Escherichia coli constitutive promoter $P_{CP41}$, the nucleotide sequence of which was positions 1493-1670 of SEQ ID No. 10; and (d) a promoter downstream homologous arm fadDdown of the sthA gene, the nucleotide sequence of which was positions 1671-1722 of SEQ ID No. 10.

(4-c) Homologous Recombination:

The above sthAup-kan-$P_{CPA1}$-sthAdown fragment was electroporated into the FM03/pKD46 competent cells prepared in (4-a), the cells were placed in an LB plate containing kanamycin (concentration: 50 µg/ml) overnight at 37° C., and clones were selected. A sthA-PIF/sthA-PIR primer was used for PCR amplification and identification (an amplified target band of 2,000 bp was positive, and an amplified target band of about 400 bp was negative), and positive clones were selected and named FM04-kan. The primer binding positions were the upstream and downstream regions of the promoter of the sthA gene of *Escherichia coli* BW25113, respectively. The results of sequencing analysis indicate that the genome of FM04-kan contains the sthAup-kan-$P_{CPA1}$-sthAdown fragment of the step (4-b).

(4-d) Elimination of Resistance:

The kanamycin resistance of FM04-kan was eliminated using the pCP20 plasmid according to the method of the step (2). The sthA-PIF/sthA-PIR primer was used for PCR amplification and identification (an amplified target band of about 600 bp was positive, and an amplified target band of about 2,000 bp or 400 bp was negative), and positive clones were selected and named FM04.

FM04 is a strain obtained by substituting the constitutive promoter $P_{CPA1}$ for the promoter of the sthA gene of FM03. In FM03, the sthA gene encodes the protein shown in SEQ ID No. 12, and the coding sequence of the sthA gene is shown in SEQ ID No. 11. The results of sequencing analysis indicate that the constitutive promoter $P_{CPA1}$ is substituted for the sthA gene promoter on the genome of FM04, and the expression of the sthA gene is initiated by $P_{CPA1}$.

(5) Knockout of β-Ketoacyl-ACP Synthase II Gene fabF.

Starting from the recombinant bacteria FM04, the fabF gene of FM04 was knocked out to obtain FM05. The specific steps were as follows:

(5-a) Preparation of P1 Phage Containing *Escherichia coli* Gene Fragment Having fabF Knockout Trait.

The *Escherichia coli* gene fragment having the fabF knockout trait was derived from *Escherichia coli* strain JW1081. JW1081 was a product of the National Institute of Genetics (NIG, Japan). According to the P1 phage preparation method of the step (1), the strain JW1081 was substituted for the JW1176 strain, and the phage P1vir fabF containing the *Escherichia coli* gene fragment having the fabF knockout trait was obtained.

(5-b) Construction of *Escherichia coli* Strain FM05-Kan Using P1 Phage Transduction Technology:

According to the method of the step (1), the FM04 of the step (4) was substituted for the *Escherichia coli* BW25113. A fabF-IF/fabF-IR primer was used for PCR amplification and identification (an amplified target band of about 1700 bp was positive), and positive clones were selected and named FM05-Kan.

(5-c) Elimination of Resistance:

According to the method of the step (1), FM05-Kan was substituted for FM01-Kan, and the kanamycin resistance of the strain was eliminated. The fabF-IF/fabF-IR primer was used for PCR amplification and identification (an amplified target band of 400 bp was positive), and positive clones were selected and named FM05.

FM05 is a strain obtained by knocking out the fabF gene of FM04. In FM04, the fabF gene encodes the protein shown in SEQ ID No. 14, and the coding sequence of the fabF gene is shown in SEQ ID No. 13. FadF-IF/fadF-IR obtains a fragment of about 400 bp by amplification from the genomic DNA of FM05, and obtains a fragment of about 1600 bp by amplification from the genomic DNA of FM04. The fabF-IF and fabF-IR primer binding positions are the upstream region and the downstream region of the fabF gene of *Escherichia coli* BW25113, respectively. The results of sequencing analysis show that there is no fabF gene in the genome of FM05, and FM05 is a strain obtained by knocking out the fabF gene of FM04.

(6) Knockout of Gene fabH of β-Ketoacyl-ACP Synthase III.

Starting from the recombinant bacteria FM05, the fabH gene of FM05 was knocked out to obtain FM06. The specific steps were as follows:

(6-a) Preparation of P1 Phage Containing *Escherichia coli* Gene Fragment Having fabH Knockout Trait.

The *Escherichia coli* gene fragment having the fabH knockout trait was derived from *Escherichia coli* strain JW1077. JW1077 was a product of the National Institute of Genetics (NIG, Japan). According to the P1 phage preparation method of the step (1), the strain JW1077 was substituted for the JW1176 strain, and the phage P1vir fabH containing the *Escherichia coli* gene fragment having the fabH knockout trait was obtained.

(6-b) Construction of *Escherichia coli* Strain FM06-Kan Using P1 Phage Transduction Technology:

According to the method of the step (1), the FM05 of the step (4) was substituted for the *Escherichia coli* BW25113. A fabH-IF/fabH-IR primer was used for PCR amplification and identification (an amplified target band of about 1700 bp was positive), and positive clones were selected and named FM06-Kan.

(6-c) Elimination of Resistance:

According to the method of the step (1), FM06-Kan was substituted for FM01-Kan, and the kanamycin resistance of the strain was eliminated. The fabH-IF/fabH-IR primer was used for PCR amplification and identification (an amplified target band of about 400 bp was positive), and positive clones were selected and named FM06.

FM06 is a strain obtained by knocking out the fabH gene of FM05. In FM05, the fabH gene encodes the protein shown in SEQ ID No. 16, and the coding sequence of the fabH gene is shown in SEQ ID No. 15. FabH-IF/fabH-IR obtains a fragment of about 400 bp by amplification from the genomic DNA of FM06, and obtains a fragment of about 1400 bp by amplification from the genomic DNA of FM05. The fabH-IF and fabH-IR primer binding positions are the upstream region and the downstream region of the fabH gene of *Escherichia coli* BW25113, respectively. The results of sequencing analysis show that there is no fabH gene in the genome of FM06, and FM06 is a strain obtained by knocking out the fabH gene of FM05.

(7) Enhancement of Expression of atoS Gene and atoC Gene by Promoter Substitution.

Starting from the recombinant bacteria FM06, the *Escherichia coli* constitutive promoter $P_{CPA1}$ was substituted for the promoter of the short-chain fatty acid degradation regulatory gene cluster atoSC (the gene cluster contained the atoS gene and the atoC gene), and recombinant *Escherichia coli* FM07 was obtained. The specific steps were as follows:

(7-a) Preparation of Host Bacteria Containing pKD46 Plasmid:

The pKD46 plasmid was transformed into the FM06 strain obtained in the previous step according to the method of the step (2) to obtain recombinant *Escherichia coli* FM06/pKD46 containing the plasmid pKD46, and then FM06/pKD46 competent cells were prepared.

(7-b) Preparation of Targeting Fragment atoSCup-Kan-P$_{CPA1}$-atoSCdown:

Using pUC57-9K of the step (2) as a template, an atoS-Cup-kan-PCPA1-atoSCdown fragment was amplified using a primer atoSC-PF/atoSC-PR. The sequence of the atoSCup-kan-P$_{CPA1}$-atoSCdown fragment was SEQ ID No. 17 in the sequence listing, and the fragment contained (a) a promoter upstream homologous arm atoSCup of the atoSC gene cluster, the nucleotide sequence of which was positions 1-51 of SEQ ID No. 17; (b) a kanamycin resistance gene (LOXP-kan-LOXP) flanked by LOXP, the nucleotide sequence of which was positions 52-1492 of SEQ ID No. 17; (c) an *Escherichia coli* constitutive promoter P$_{CPA1}$, the nucleotide sequence of which was positions 1493-1670 of SEQ ID No. 17; and (d) a promoter downstream homologous arm atoSC-down of the atoSC gene cluster, the nucleotide sequence of which was positions 1671-1722 of SEQ ID No. 17.

(7-c) Homologous Recombination:

The above atoSCup-kan-P$_{CPA1}$-atoSCdown fragment was electroporated into the FM06/pKD46 competent cells prepared in (7-a), the cells were placed in an LB plate containing kanamycin (concentration: 50 μg/ml) overnight at 37° C., and clones were selected. An atoSC-PIF/atoSC-PIR primer was used for PCR amplification and identification (an amplified target band of 2,000 bp was positive, and an amplified target band of 400 bp was negative), and positive clones were selected and named FM07-kan. The primer binding positions were the upstream and downstream regions of a promoter of the atoSC gene cluster of *Escherichia coli* BW25113, respectively. The results of sequencing analysis indicate that the genome of FM07-kan contains the atoSCup-kan-P$_{CPA1}$-atoSCdown fragment of the step (7-b).

(7-d) Elimination of Resistance:

The kanamycin resistance of FM07-kan was eliminated using the pCP20 plasmid according to the method of the step (2). The atoSC-PIF/atoSC-PIR primer was used for PCR amplification and identification (an amplified target band of about 600 bp was positive, and an amplified target band of about 2,000 bp or 400 bpbp was negative), and positive clones were selected and named FM07.

FM07 is a strain obtained by substituting the constitutive promoter P$_{CPA1}$ for the promoter of the atoSC gene cluster of FM06. In FM06, the atoS gene in the atoSC gene cluster encodes the protein shown in SEQ ID No. 19, the coding sequence of the atoS gene is shown in SEQ ID No. 18, the atoC gene encodes the protein shown in SEQ ID No. 21, and the coding sequence of the atoC gene is shown in SEQ ID No. 20. The results of sequencing analysis indicate that the constitutive promoter P$_{CPA1}$ is substituted for the promoter of the atoSC gene cluster on the genome of FM07, and the expression of the atoS gene and the atoC gene in the atoSC gene cluster is initiated by P$_{CPA1}$.

TABLE 1

Sequence listing of primers used in Example 1

| Primer | Sequence | Application |
|---|---|---|
| fadR-IF | 5'-AAATAATCAATGATGTTTTTATGTT-3' | Step (1) |
| fadR-IR | 5'-ATAATCGCGCACCGCTGGATCGGGG-3' | Step (1) |
| fadL-PF | 5'-CTTAAAAATGATCTAAAACAAAATTCACCCGAA TCCATGAGTGCGCCACCGTCTCGAGAATATCCTCC TT-3' | Step (2) |
| fadL-PR | 5'-GCGACTGCGAGAGCAGACTTTGTAAACAGGGTT TTCTGGCTCATGACCATGGTATATCTCCTTCTTAA AA-3' | Step (2) |
| fadL-PIF | 5'-GGGGTTTCATCAGCACTACATTTAC-3' | Step (2) |
| fadL-PIR | 5'-CGGTCAAACATAGTAATCAATGCGG-3' | Step (2) |
| fadD-PF | 5'-TACGGTAAAGATAAAAATAAATAGTGACGCGC TTCGCAACCTTTTCGTTGGTCTCGAGAATATCCTC CTT-3' | Step (3) |
| fadD-PR | 5'-ATCTCCGTCGGAACGTCCGCGGGATAACGGTTA AGCCAAACCTTCTTCAAGGTATATCTCCTTCTTAA AA-3' | Step (3) |
| fadD-PIF | 5'-TGGTTTTATGGCGGTCGTGGCTGGC-3' | Step (3) |
| fadD-PIR | 5'-TGTTGCAAATAAGCGGCAAACGCGC-3' | Step (3) |
| sthA-PF | 5'-TCCAATAAAACGTCAGGGCAAAAGTAAGAAAC AGACAAAGCAAAGGCCGCGTCTCGAGAATATCCT CCTT-3' | Step (4) |
| sthA-PR | 5'-CCGGGGCCGGAACCTATTACTATGGCATCGTAATC GTAGGAATGTGGCATGGTATATCTCCTTCTTAAAA-3' | Step (4) |
| sthA-PIF | 5'-GGCACTATACCAGAGAATGAACATA-3' | Step (4) |
| sthA-PIR | 5'-TTGAATTCTATAATGCGGCTGACGG-3' | Step (4) |
| fabF-IF | 5'-AGCTGGTAATGGCTCTGGAAGAAGA-3' | Step (5) |
| fabF-IR | 5'-GGTAAAACAACCATCACCAAACTGC-3' | Step (5) |

TABLE 1-continued

Sequence listing of primers used in Example 1

| Primer | Sequence | Application |
|---|---|---|
| fabH-IF | 5'-TGCGGTCGCGATTGAACAGGCAGTG-3' | Step (6) |
| fabH-IR | 5'-AGTTTGCCAGGTTTTATTCAGTTCT-3' | Step (6) |
| atoSC-PF | 5'-CTCAGGTGACCGATGGAGTGTGGTTAAGGTAGCGGTAAAAGCGTGTTACCGTCTCGAGAATATCCTCCTT-3' | Step (7) |
| atoSC-PR | 5'-ATCATTTGATTGCGTAAGCGGCGTGGATAAATCCACTTCATATAATGCATGGTATATCTCCTTCTTAAAA-3' | Step (7) |
| atoSC-PIF | 5'-TCTCGCTGATGTAACGCATTAACGA-3' | Step (7) |
| atoSC-PIR | 5'-TCATAGCGATCGCCTAGTGCCTGAT-3' | Step (7) |

Example 2 Preparation of Strain FM08 for Producing β-Alanine and Production of β-Alanine I. Preparation of Strain FM08 for Producing β-Alanine A preparation method of FM08 was as follows, and primers used were shown in Table 2.

(1) Construction of Plasmid Expressing *Chloroflexus Aurantiacus* Malonyl-CoA Reductase Truncation Gene mcrC.

(1-a) PCR Amplification of mcrC Gene.

The nucleotide sequence of the modified *Chloroflexus aurantiacus* malonyl-CoA reductase truncation gene mcrC was shown in SEQ ID No. 22, and the mcrC gene encoded the protein shown in SEQ ID No. 23 in the sequence listing. The mcrC gene shown in SEQ ID No. 22 was gene-synthesized, and then the mcrC gene shown in SEQ ID No. 22 was ligated to the pUC57 vector by a Gibson assembly method (Gibson D G, Young L, et al. Enzymatic assembly of DNA molecules up to several hundred kilobases. Nat. methods. 2009; 6(5):343-345) to obtain a vector pUC57-mcrC. Using mcrC-F and mcrC-R as primers and the vector pUC57-mcrC as a template, PCR amplification was carried out using high-fidelity TransStart FastPfu DNA polymerase (Beijing TransGen Biotech Co., Ltd., product catalogue: AP221) to obtain a mcrC gene fragment with a correct sequence.

(1-b) Construction of Recombinant Expression Vector Containing mcrC Gene.

A vector pLB1a (the nucleotide sequence of the vector pLB1a was shown in SEQ ID No. 24) was digested with NcoI and XhoI, and a large fragment LB1a-NX of the vector was recovered. The mcrC gene fragment with the correct sequence obtained in the above (1-a) was ligated with the LB1a-NX fragment by the Gibson assembly method. *Escherichia coli* DH5α competent cells were transformed by a CaCl$_2$ method (Beijing TransGen Biotech Co., Ltd., product catalogue: CD201). The cells were spread on an LB plate containing ampicillin and cultured overnight at 37° C. Clones were selected and identified by a primer F105-F/mcrC-R. The positive clones with the correct sequence of the target fragment were selected, and the obtained positive recombinant plasmid was named pLB1a-mcrC.

(2) Construction of Plasmid Expressing *Corynebacterium glutamicum* Acetyl-CoA Carboxylase Acc Gene Cluster.

The *Corynebacterium glutamicum* acetyl-CoA carboxylase acc gene cluster was gene-synthesized and ligated to the pUC57 vector by the Gibson assembly method to obtain a vector pUC57-acc. The nucleotide sequence of the acc gene cluster was shown in SEQ ID No. 25. The sequence of the RBS1 site preceding the accBC gene was positions 2-7 of SEQ ID No. 25. The nucleotide sequence of accBC was positions 15-1790 of SEQ ID No. 25, and the amino acid sequence was SEQ ID No. 26. The nucleotide sequence of accDA was positions 1805-3259 of SEQ ID No. 25, and the amino acid sequence was SEQ ID No. 27. The RBC2 site was contained between the accBC and accDA sequences, and the sequence was positions 1792-1797 of SEQ ID No. 25. Using acc-F and acc-R as a primers and the vector pUC57-acc as a template, the acc gene fragment with the correct sequence was amplified by PCR using high-fidelity TransStart FastPfu DNA polymerase.

The plasmid pLB1a-mcrC of the step (1) was digested with XhoI and EcoRI to obtain a large fragment LB1a-mcrC-XE. The above acc gene fragment was ligated with the LB1a-mcrC-XE fragment by the Gibson assembly method. *Escherichia coli* DH5a competent cells were transformed by the CaCl$_2$ method. The cells were spread on an LB plate containing ampicillin and cultured overnight at 37° C. Clones were selected and identified by a primer acc-F/T58-R. The positive clones with the correct sequence of the target fragment were selected and the obtained positive recombinant plasmid was named pLB1a-mcrC-acc.

(3) Construction of Plasmid Expressing *Marinobacter hydrocarbonoclasticus* Exogenous Alkane Uptake Outer Membrane Protein Gene alkL Gene.

The genomic DNA of *Marinobacter hydrocarbonoclasticus* was extracted using a bacterial genome extraction kit (Tiangen Biotech Co., Ltd., product catalogue: DP302). Using the extracted total DNA of the *Marinobacter hydrocarbonoclasticus* genome as a template, the alkL gene fragment was amplified by PCR with a primer alkL-F/alkL-R, and an RBS sequence was introduced into the primer. The vector pLB1a-mcrC-acc obtained by the step (2) was digested with EcoRI and PstI to obtain a large fragment LB1a-mcrC-acc-EP. The above alkL gene fragment was ligated with the LB1a-mcrC-acc-EP fragment by the Gibson assembly method. *Escherichia coli* DH5a was transformed and identified with a primer alkL-F/T58-R. Positive clones with the correct sequence of the target fragment were selected, and the obtained positive recombinant plasmid was named pLB1a-mcrC-acc-alkL.

PLB1a-mcrC-acc-alkL contains the mcrC gene shown in SEQ ID No. 22, the acc gene cluster shown in SEQ ID No. 25, and the DNA fragment shown in SEQ ID No. 28, where the positions 2-7 of SEQ ID No. 28 are the sequence of RBS, and the positions 15-686 of SEQ ID No. 28 are the nucleotide sequence of alkL. PLB1a-mcrC-acc-alkL may express the mcrC protein shown in SEQ ID No. 23, the accBC protein shown in SEQ ID No. 26, the accDA protein shown in SEQ ID No. 27 and the alkL protein shown in SEQ ID No. 29.

(4) Construction of Plasmid Expressing *Escherichia coli* β-Alanine Aminotransferase Gene Baat Gene (puuE Gene)

Genomic DNA was extracted from *Escherichia coli*, and the puuE gene fragment was amplified with a primer puuE-F/puuE-R. A vector pSB1s (the nucleotide sequence of the vector pSB1s was shown in SEQ ID No. 30) was digested with NcoI and XhoI, and a large fragment SB1s-NX of the vector was recovered. The puuE gene fragment was ligated with the SB1s-NX fragment by the Gibson assembly method. *Escherichia coli* DH5a was transformed and identified by a primer F105-F/puuE-R. Positive clones with the correct sequence of the target fragment were selected, and the obtained positive recombinant plasmid was named pSB1s-puuE.

(5) Construction of Plasmid Expressing *Bacillus subtilis* Glutamate Dehydrogenase Gene Gdh Gene (rocG Gene)

Genomic DNA was extracted from *Escherichia coli*, a rocG gene fragment was amplified with a primer rocG-F/rocG-R, and the RBS sequence was introduced into the primer. A large fragment SB1s-puuE-XP was obtained by digesting the vector pSB1s-puuE of the step (4) with XhoI and PstI. The rocG gene fragment was ligated with the SB1s-puuE-XP fragment. *Escherichia coli* DH5a was transformed and identified with a primer rocG-F/T-58. Positive clones with the correct sequence of the target fragment were selected to extract plasmid, and the obtained positive recombinant plasmid was named pSB1s-puuE-rocG.

PSB1s-puuE-rocG contains the puuE gene shown in SEQ ID No. 31 and the DNA fragment shown in SEQ ID No. 33, where the positions 2-7 of SEQ ID No. 33 are the sequence of RBS, and the positions 15-1289 of SEQ ID No. 33 are the sequence of the rocG gene. PSB1s-puuE-rocG may express the puuE protein shown in SEQ ID No. 32 and the rocG protein shown in SEQ ID No. 34.

(6) Construction of Recombinant *Escherichia coli* FM08.

Competent cells were prepared from the strain FM07 of Example 1, and the pLB1a-mcrC-acc-alkL and pSB1s-puuE-rocG prepared in the above steps were introduced into FM07. The cells were spread on an LB plate containing streptomycin and ampicillin and cultured overnight at 37° C. Positive clones containing the pLB1a-mcrC-acc-alkL and pSB1s-puuE-rocG were selected and named FM08.

FM08 was a strain obtained by transforming *Escherichia coli* BW25113 as the following (a1)-(a12):

(a1) the fatty acid degradation transcription factor fadR gene was knocked out;

(a2) the *Escherichia coli* constitutive promoter $P_{CP41}$ was substituted for the fadL gene promoter;

(a3) the *Escherichia coli* constitutive promoter $P_{CP41}$ was substituted for the fadD gene promoter;

(a4) the *Escherichia coli* constitutive promoter $P_{CP41}$ was substituted for the sthA gene promoter;

(a5) the β-ketoacyl-ACP synthase II gene fabF gene was knocked out;

(a6) the β-ketoacyl-ACP synthase III gene fabH gene was knocked out;

(a7) the *Escherichia coli* constitutive promoter $P_{CP41}$ was substituted for the atoSC gene cluster promoter;

(a8) the malonyl-CoA reductase truncation gene mcrC gene was introduced;

(a9) the acetyl-CoA carboxylase acc gene cluster was introduced;

(a10) the exogenous alkane uptake outer membrane protein gene alkL gene was introduced;

(a11) the β-alanine aminotransferase gene puuE gene was introduced; and (a12) the glutamate dehydrogenase gene rocG gene was introduced.

Competent cells were prepared from the strain FM07, and plasmids pSB1s and pLB1a were introduced into the FM07 by the CaCl$_2$ method. The cells were spread on an LB plate containing streptomycin and ampicillin and cultured overnight at 37° C. Clones containing the plasmids pSB1s and pLB1a were selected and named FM00 as a control.

TABLE 2

Sequence listing of primers used in Example 2

| Primer | Sequence | Application |
|---|---|---|
| mcrC-F | 5'-GCTAACAGGAGGAATTAACCATGGCAGATCTCC ATCACCATCATC-3' | Step (1) |
| mcrC-R | 5'-CACTAGTACCAGATCTACCCTCGAGTTACACGGT AATCGCCCGTCCGCGA-3' | Step (1) |
| acc-F | 5'-ACGGGCGATTACCGTGTAACCAGGAGGAATTAA CATGTCAGTCGAGACTAGGAAGATCA-3' | Step (2) |
| acc-R | 5'-GCTGCAGACCGAGCTCACCGAATTCTTACTGCGC TAAACGCTCAAATCGT-3' | Step (2) |
| alkL-F | 5'-TGAGCGTTTAGCGCAGTAAGCAGGAGGAATTAA CATGAAACCTAAAATCATTAGTAAAG-3' | Step (3) |
| alkL-R | 5'-GGCTGCCGCGCGGCACCAGCTTAAAAGCGATAC GCAACGCCGATA-3' | Step (3) |
| puuE-F | 5'-ACTAGTACCAGATCTACCCTATGAGCAACAATG AATTCCATCAGC-3' | Step (4) |
| puuE-R | 5'-CACTAGTACCAGATCTACCCTCGAGTTAATCGCT CAGCGCATCCTGCAAA-3' | Step (4) |
| rocG-F | 5'-GGATGCGCTGAGCGATTAACCAGGAGGAATTAA CATGTCAGCAAAGCAAGTCTCGAAAG-3' | Step (5) |

TABLE 2-continued

Sequence listing of primers used in Example 2

| Primer | Sequence | Application |
|---|---|---|
| rocG-R | 5'-GGCTGCCGCGCGGCACCAGCTTAGACCCATCCG CGGAAACGCGAT-3' | Step (5) |
| F105-F | 5'-TAGCATTTTTATCCATAAGATTAGC-3' | Steps (1, 4) |
| T58-R | 5'-TTTCACTTCTGAGTTCGGCATGGGG-3' | Steps (2, 3, 5) |

II. Preparation of β-Alanine

1. Preparation of Media

A medium: The A medium was a sterile medium consisting of solutes and a solvent, where the solvent was water, and the solutes and their concentrations were: 25 mM of $NaHPO_4$, 25 mM of $KH_2PO_4$, 50 mM of $NH_4Cl$, 5 mM of $Na_2SO_4$, 2 mM of $MgSO_4$, 0.5% by volume of glycerol, 0.5% by mass of yeast powder, 50 µM of $FeCl_3$, 20 µM of $CaCl_2$, 10 µM of $MnCl_2$, 10 µM of $ZnSO_4$, 2 µM of $CoCl_2$, 2 µM of $NiCl_2$, 2 µM of $Na_2MO_4$, 2 µM of $Na_2SeO_3$ and 2 µM of $H_3BO_3$.

B medium: The B medium was a sterile medium obtained by adding palmitic acid, a polyoxyethylene ether Brij58 emulsifier, Biotin and vitamin B6 to the A medium, where the mass percentage concentration of the palmitic acid was 0.5%, the mass percentage concentration of the polyoxyethylene ether Brij58 emulsifier was 0.2%, the concentration of the Biotin was 40 mg/L, and the concentration of the vitamin B6 was 10 mg/L.

C medium: The C medium was a sterile medium obtained by adding palmitic acid, the polyoxyethylene ether Brij58 emulsifier, Biotin, $NaHCO_3$, vitamin B6 and glutamic acid to the A medium, where the mass percentage concentration of the palmitic acid was 1%, the mass percentage concentration of the polyoxyethylene ether Brij58 emulsifier was 0.2%, the concentration of the Biotin was 40 mg/L, the concentration of the $NaHCO_3$ was 20 mM, the concentration of the vitamin B6 was 10 mg/L, and the concentration of the glutamic acid was 2 mM.

2. Preparation of β-Alanine

The experiment was repeated for three times, and the specific steps of each experiment were as follows:

2.1. Culture of Bacterial Cells.

The strain FM08 obtained in the step I and cultured overnight was cultured according to the following method: the strain was inoculated into 20 ml of the A medium containing streptomycin and kanamycin (the concentration of both streptomycin and kanamycin was 50 mg/L) at an inoculum size of 1%, and cultured at 37° C. for 12 h to collect the bacterial cells; the collected bacterial cells were transferred to 20 ml of the B medium containing streptomycin and kanamycin (the concentration of both streptomycin and kanamycin was 50 mg/L), and cultured at 37° C. for 6 h to obtain a culture solution; the $OD_{600}$ of the culture solution was 6; an arabinose inducer was added to the culture solution to allow the concentration of the arabinose inducer in the culture solution to be 0.2% by mass, the cells were cultured at 37° C. for 12 h, and the cells were collected to obtain FM08 cells.

According to the above method, FM00 was cultured in the A medium and the B medium free of streptomycin and kanamycin to obtain FM00 cells.

2.2. Whole Cell Catalytic Production of β-Alanine.

30 mg (i.e., $1 \times 10^{11}$ cfu) by dry weight of the FM08 cells collected in the above step 2.1 were suspended in a shake flask containing 20 ml of the C medium and cultured at 37° C. for 24 h. Then a supernatant was collected after centrifugation and filtered by a 0.22 µm filter to obtain a filtrate, and the filtrate was an FM08 sample to be tested.

According to the above method, FM00 cells were substituted for FM08, and the other steps were unchanged, to obtain the FM00 sample to be tested.

Using β-alanine (Sigma, 05159-100G) as a standard, the content of β-alanine in each sample to be tested was quantitatively analyzed by HPLC using a standard curve method (external standard method).

The quantitative test results are shown in FIG. 1. The average content of β-alanine in the FM08 sample to be tested is 0.36 g/L (i.e., 0.36 g/$5 \times 10^{12}$ cfu), and the mass percentage concentration of palmitic acid is 0.78%. The average content of β-alanine in the FM00 sample to be tested is 0 mg/L, and the mass percentage concentration of palmitic acid is 0.89%. The conversion rate of β-alanine prepared with palmitic acid as a substrate using FM08 is 16.36%, and β-alanine could not be obtained using FM00. It is indicated that β-alanine may be prepared using FM08.

Example 3 Preparation of Strain FI08 for Producing 3-Hydroxypropionic Acid and Production of 3-Hydroxypropionic Acid I. Preparation of Strain FI08 for Producing 3-Hydroxypropionic Acid A preparation method of FI08 was as follows, and primers used were shown in Table 3.

(1) Construction of plasmid expressing *Corynebacterium glutamicum* acetyl-CoA carboxylase acc gene cluster.

(1-a) Extraction of genomic DNA of *Corynebacterium glutamicum* and PCR amplification of acc gene cluster.

The genomic DNA of *Corynebacterium glutamicum* was extracted using a bacterial genome extraction kit (Tiangen Biotech Co., Ltd., product catalogue: DP302). Using the extracted total DNA of the *Corynebacterium glutamicum* genome as a template and accBC-F and accL-R as primers, a gene fragment accBC was amplified by PCR using high-fidelity TransStart FastPfu DNA polymerase, and the target fragment was recovered by agarose gel electrophoresis. With the total DNA of the *Corynebacterium glutamicum* genome as a template and accL-F and accDA-R as primers, a gene fragment accDA was amplified by PCR using high-fidelity TransStart FastPfu DNA polymerase, and the target fragment was recovered by agarose gel electrophoresis. A NheI site was introduced into the accDA-R primer to facilitate insertion of a subsequent gene fragment; and the 3' terminal of the accBC fragment and the 5' terminal of the accDA fragment introduced complementary sequences containing RBS by primers for the next round of assembly.

Using a mixture of the two fragments of accBC and accDA as a template and accBC-F and accDA-R as primers, the acc fragment with a full-length gene sequence was further PCR-amplified, and the target fragment was recovered by agarose gel electrophoresis.

(1-b) Construction of Recombinant Expression Vector Containing Acc Gene.

A vector pSB1s (the nucleotide sequence of the vector pSB1s was shown in SEQ ID No. 30) was digested with NcoI and XhoI, and a large fragment SB1s-NX of the vector was recovered. The above acc fragment was ligated with the SB1s-NX fragment by the Gibson assembly method. Escherichia coli DH5a competent cells were transformed by the CaCl$_2$) method. The cells were uniformly spread on an LB plate containing streptomycin and cultured overnight at 37° C. Clones were selected, and the clones capable of amplifying the target fragment were identified by a primer F-105/accL-R and sequenced. The positive clones were selected, plasmids were extracted, and the obtained positive plasmid was named pSB1s-acc. The pSB1s-acc contains a DNA fragment shown in positions 15-3259 of SEQ ID No. 25.

(2) Construction of Plasmid Expressing *Marinobacter hydrocarbonoclasticus* Exogenous Alkane Uptake Outer Membrane Protein Gene alkL Gene.

Genomic DNA was extracted from *Marinobacter hydrocarbonoclasticus*, the alkL gene fragment was amplified with a primer alkL-F/alkL-R', and the RBS sequence was introduced into the primer. A large fragment SB1s-acc-HS was obtained by digesting the vector pSB1s-acc with NheI and SpeI. The alkL fragment was ligated with the SB1s-acc-HS fragment by the Gibson assembly method. *Escherichia coli* DH5a was transformed and identified with a primer alkL-F/T-58. Positive clones with the correct sequence of the target fragment were selected, plasmids were extracted, and the obtained positive recombinant plasmid was named pSB1s-acc-alkL.

PSB1s-acc-alkL contains the DNA fragment shown in positions 15-3259 of SEQ ID No. 25 and the DNA fragment shown in SEQ ID No. 28. The positions 2-7 of SEQ ID No. 28 are the sequence of RBS, and the positions 15-686 of SEQ ID No. 28 are the nucleotide sequence of alkL. The pSB1s-acc-alkL may express the accBC protein shown in SEQ ID No. 26, the accDA protein shown in SEQ ID No. 27, and the alkL protein shown in SEQ ID No. 29.

(3) Construction of Plasmid Expressing *Chloroflexus aurantiacus* Malonyl-CoA Reductase Gene Mcr.

(3-a) PCR Amplification of Mcr Gene.

The nucleotide sequence of the modified *Chloroflexus aurantiacus* malonyl-CoA reductase gene mcr gene was shown in SEQ ID No. 36, where the nucleotide sequence of the N-terminal domain of mcr was positions 1-1689 of SEQ ID No. 36, the nucleotide sequence of the C-terminal domain of mcr was positions 1704-3749 of SEQ ID No. 36, the RBS site was contained between the N-terminal domain and the C-terminal domain, and the sequence was positions 1691-1696 of SEQ ID No. 36. The mcr gene sequence was obtained by whole gene synthesis and ligated to the pUC57 vector by the Gibson assembly method to obtain the vector pUC57-mcr. Using pUC57-mcr as a template, a primer mcr-F/mcr-R was used for amplification to obtain the mcr gene fragment with the correct sequence.

(3-b) Construction of Recombinant Expression Vector Containing Mcr Gene.

The mcr gene fragment with the correct sequence obtained by the above (3-a) was subjected to agarose gel electrophoresis to recover the target fragment. A vector pXB1k (the nucleotide sequence of the vector pXB1k was shown in SEQ ID No. 35) was digested with NcoI and XhoI, and a large fragment XB1k-NX of the vector was recovered. The mcr gene fragment with the correct sequence obtained in the above (3-a) was ligated with the XB1k-NX fragment by the Gibson assembly method. *Escherichia coli* DH5a competent cells were transformed by the CaCl$_2$ method. The cells were spread on an LB plate containing streptomycin and cultured overnight at 37° C. Clones were selected, and the clones capable of amplifying the target fragment were identified by a primer F-105/mcr-R and sequenced. The positive clones were selected, plasmids were extracted, and the obtained positive plasmid was named pXB1k-mcr.

PXB1k-mcr contains the DNA fragment shown in SEQ ID No. 36 and may express the mcr protein shown in SEQ ID No. 37.

(4) Construction of Recombinant *Escherichia coli* FM08.

Competent cells were prepared from the strain FM07 of Example 1, and the plasmids pSB1s-acc-alkL and pXB1k-mcr were transformed into FM07 by the CaCl$_2$ method. The cells were spread on an LB plate containing streptomycin and kanamycin and cultured overnight at 37° C. Positive clones containing the pSB1s-acc-alkL and pXB1k-mcr were selected and named FI08.

FI08 was a strain obtained by transforming *Escherichia coli* BW25113 as the following (b1)-(b10):

(b1) the fatty acid degradation transcription factor fadR gene was knocked out;

(b2) the *Escherichia coli* constitutive promoter $P_{CPA1}$ was substituted for the fadL gene promoter;

(b3) the *Escherichia coli* constitutive promoter $P_{CPA1}$ was substituted for the fadD gene promoter;

(b4) the *Escherichia coli* constitutive promoter $P_{CPA1}$ was substituted for the sthA gene promoter;

(b5) the β-ketoacyl-ACP synthase II gene fabF gene was knocked out;

(b6) the β-ketoacyl-ACP synthase III gene fabH gene was knocked out;

(b7) the *Escherichia coli* constitutive promoter $P_{CPA1}$ was substituted for the atoSC gene cluster promoter;

(b8) the acetyl-CoA carboxylase acc gene cluster was introduced;

(b9) the exogenous alkane uptake outer membrane protein gene alkL gene was introduced; and (b10) the malonyl-CoA reductase gene mcr gene was introduced.

Competent cells were prepared from the strain FM07 of Example 1, and plasmids pSB1s and pXB1k were introduced into the FM07 by the CaCl$_2$) method. The cells were spread on an LB plate containing streptomycin and ampicillin and cultured overnight at 37° C. Clones containing the plasmids pSB1s and pXB1k were selected and named FC00 as a control.

TABLE 3

Sequence listing of primers used in Example 3

| Primer | Sequence | Application |
|---|---|---|
| accBC-F | 5'-GCTAACAGGAGGAATTAACATGTCAGTCGAGAC TAGGAAGATCA-3' | Step (1) |
| accL-R | 5'-AAGTGTGTTCCATGCCCCACACCATGTTAATTCC TCCTGTTACTTGATCTCGAGGAGAACAACG-3' | Step (1) |
| accL-F | 5'-CGTTGTTCTCCTCGAGATCAAGTAACAGGAGGA ATTAACATGGTGTGGGCATGGAACACACTT-3' | Step (1) |
| accDA-R | 5'-ACTAGTACCAGATCTACCCTGCTAGCTTACTGCG CTAAACGCTCAAATCGT-3' | Step (1) |
| alkL-F | 5'-TGAGCGTTTAGCGCAGTAAGCAGGAGGAATTAA CATGAAACCTAAAATCATTAGTAAAG-3' | Step (2) |
| alkL-R' | 5'-CCGAGCTCACCGAATTCACCTTAAAAGCGATAC GCAACGCCGATA-3' | Step (2) |
| mcr-F | 5'-GCTAACAGGAGGAATTAACCATGGGCAGCAGCC ATCACCATCATC-3' | Step (3) |
| mcr-R | 5'-ACTAGTACCAGATCTACCCTTTACACGGTAATCG CCCGTCCGCGA-3' | Step (3) |
| F-105 | 5'-TAGCATTTTTATCCATAAGATTAGC-3' | Steps (1, 3) |
| T-58 | 5'-TTTCACTTCTGAGTTCGGCATGGGG-3' | Step (2) |

II. Preparation of 3-Hydroxypropionic Acid (3-HP)

1. Preparation of Media

D medium: The D medium was a sterile medium obtained by adding palmitic acid and a polyoxyethylene ether Brij58 emulsifier to the A medium of Example 2, where the mass percentage concentration of the palmitic acid was 0.5%, and the mass percentage concentration of the polyoxyethylene ether Brij58 emulsifier was 0.2%.

E medium: The E medium was a sterile medium obtained by adding palmitic acid, a polyoxyethylene ether Brij58 emulsifier, Biotin and $NaHCO_3$ to the A medium of Example 2, where the mass percentage concentration of the palmitic acid was 1%, the mass percentage concentration of the polyoxyethylene ether Brij58 emulsifier was 0.2%, the concentration of the Biotin was 40 mg/L, and the concentration of the $NaHCO_3$ was 20 mM.

2. Preparation of 3-Hydroxypropionic Acid

The experiment was repeated for three times, and the specific steps of each experiment were as follows:

2.1. Culture of Bacterial Cells.

The strain FI08 obtained in the step I and cultured overnight was cultured according to the following method: the strain was inoculated into 20 ml of the A medium containing streptomycin and kanamycin (the concentration of both streptomycin and kanamycin was 50 mg/L) of Example 2 at an inoculum size of 1%, and cultured at 37° C. for 12 h to collect the bacterial cells; the collected cells were transferred to 20 ml of the D medium containing streptomycin and kanamycin (the concentration of both streptomycin and kanamycin was 50 mg/L), and cultured at 37° C. for 6 h to obtain a culture solution; the $OD_{600}$ of the culture solution was 6; an arabinose inducer was added to the culture solution to allow the concentration of the arabinose inducer in the culture solution to be 0.2% by mass, the cells were cultured at 37° C. for 12 h, and the cells were collected to obtain FI08 cells.

According to the above method, FC00 was cultured in the A medium and the D medium free of streptomycin and kanamycin to obtain FC00 cells.

2.2. Whole Cell Catalytic Production of 3-Hydroxypropionic Acid.

30 mg (i.e., $1 \times 10^{11}$ cfu) by dry weight of the FI08 cells collected in the above step 2.1 were suspended in a shake flask containing 20 ml of the E medium and cultured at 37° C. for 24 h. A supernatant was collected after centrifugation and filtered by a 0.22 μm filter to obtain a filtrate, and the filtrate was a sample of FI08 to be tested.

According to the above method, FC00 cells were substituted for FI08, and the other steps were unchanged, to obtain the FC00 sample to be tested.

Using 3-hydroxypropionic acid (TCI, H0297-10G) as a standard, the content of 3-hydroxypropionic acid in each sample to be tested was quantitatively analyzed by HPLC using a standard curve method (external standard method).

Figure 2:
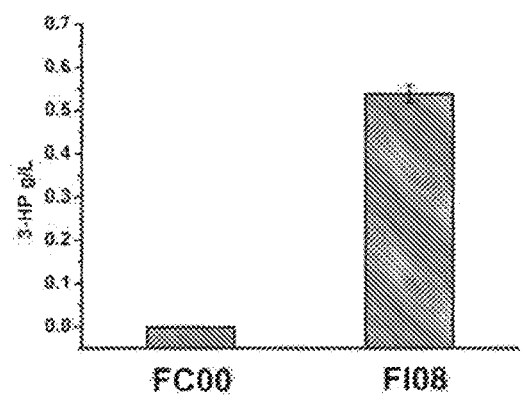
FIG. 2 shows production of 3-hydroxypropionic acid using FI08.

The quantitative test results are shown in FIG. 2. The average content of 3-hydroxypropionic acid in the FI08 sample to be tested is 0.539 g/L (i.e., 0.539 g/$5 \times 10^{12}$ cfu), and the mass percentage concentration of palmitic acid is 0.81%. The average content of 3-hydroxypropionic acid in the FC00 sample to be tested is 0 mg/L, and the mass percentage concentration of palmitic acid is 0.91%. The conversion rate of 3-hydroxypropionic acid prepared with palmitic acid as a substrate using FI08 is 28.37%, and 3-hydroxypropionic acid could not be obtained using FC00. It is indicated that 3-hydroxypropionic acid may be prepared using FI08.

Example 4 Preparation of Strain FA11 for Producing β-Alanine and Production of β-Alanine I. Preparation of Strain FA11 for Production of β-Alanine A preparation method of FA11 was as follows, and primers used were shown in Table 4.

(1) Knockout of Glyoxylate Pathway Transcriptional Repressor Gene iclR

Starting from the recombinant strain FM07 of Example 1, the iclR gene of FM07 was knocked out to obtain FA08, and the specific steps were as follows:

(1-a) Preparation of P1 Phage Containing *Escherichia coli* Gene Fragment Having iclR Knockout Trait.

The *Escherichia coli* gene fragment having the iclR knockout trait was derived from *Escherichia coli* strain JW3978. JW3978 was a product of the National Institute of Genetics (NIG, Japan). According to the P1 phage preparation method of the step (1) of Example 1, the strain JW3978 was substituted for the JW1176 strain, and the phage P1vir iclR containing the *Escherichia coli* gene fragment having the iclR knockout trait was obtained.

(1-b) Construction of *Escherichia coli* Strain FA08-Kan Using P1 Phage Transduction Technology:

The recombinant strain FM07 of Example 1 was substituted for *Escherichia coli* BW25113 according to the method of the step (1) in Example 1. An iclR-IF/iclR-IR primer was used for PCR amplification and identification (an amplified target band of 1700 bp was positive), and positive clones were selected and named FA08-Kan.

(1-c) Elimination of Resistance:

According to the method of the step (1) of Example 1, FA08-Kan was substituted for FM01-Kan, and the kanamycin resistance of the strain was eliminated. The iclR-IF/iclR-IR primer was used for PCR amplification and identification (an amplified target band of 400 bp was positive), and positive clones were selected and named FA08.

FA08 is a strain obtained by knocking out the iclR gene of FM07 in Example 1. In FM07, the iclR gene encodes the protein shown in SEQ ID No. 39, and the coding sequence of the iclR gene is shown in SEQ ID No. 38. IclR-IF/iclR-IR obtains a fragment of about 400 bp by amplification from the genomic DNA of FA08, and obtains a fragment of about 1200 bp by amplification from the genomic DNA of FM07. The primer binding positions of the iclR-IF and iclR-IR are the upstream region and the downstream region of the iclR gene of *Escherichia coli* BW25113, respectively. The results of sequencing analysis show that there is no iclR gene on the genome of FA08, and FA08 is a strain obtained by knocking out the iclR gene of FM07 in Example 1.

(2) Knockout of α-Ketoglutarate Decarboxylase Gene sucA.

Starting from FA08, the sucA gene of FA08 was knocked out to obtain FA09, and the specific steps were as follows:

(2-a) Preparation of P1 Phage Containing *Escherichia coli* Gene Fragment Having sucA Knockout Trait.

The *Escherichia coli* gene fragment having the sucA knockout trait was derived from *Escherichia coli* strain JW0715. JW0715 was a product of the National Institute of Genetics (NIG, Japan). According to the P1 phage preparation method of the step (1) of Example 1, the strain JW0715 was substituted for the JW1176 strain, and the phage P1vir sucA containing the *Escherichia coli* gene fragment having the sucA knockout trait was obtained.

(2-b) Construction of *Escherichia coli* Strain FA09-Kan Using P1 Phage Transduction Technology:

FA08 was substituted for *Escherichia coli* BW25113 according to the method of the step (1) in Example 1. A sucA-IF/sucA-IR primer was used for PCR amplification and identification (an amplified target band of 1700 bp was positive), and positive clones were selected and named FA00-Kan.

(2-c) Elimination of Resistance:

According to the method of the step (1) of Example 1, FA09-Kan was substituted for FM01-Kan, and the kanamycin resistance of the strain was eliminated. The sucA-IF/sucA-IR primer was used for PCR amplification and identification (an amplified target band of 400 bp was positive), and positive clones were selected and named FA09.

FA09 is a strain obtained by knocking out the sucA gene of FA08. In FA08, the sucA gene encodes the protein shown in SEQ ID No. 41, and the coding sequence of the sucA gene is shown in SEQ ID No. 40. SucA-IF/sucA-IR obtains a fragment of about 400 bp by amplification from the genomic DNA of FA09, and obtains a fragment of about 3200 bp by amplification from the genomic DNA of FM08. The primer binding positions of the sucA-IF and sucA-IR are the upstream region and the downstream region of the sucA gene of *Escherichia coli* BW25113, respectively. The results of sequencing analysis show that there is no sucA gene in the genome of FA00, and FA09 is a strain obtained by knocking out the sucA gene of FA08.

(3) Enhancement of Expression of aceB Gene and aceA Gene by Promoter Substitution.

Starting from the recombinant bacteria FA09, the *Escherichia coli* constitutive promoter $P_{CP41}$ was substituted for the promoter of the glyoxylate pathway aceBA gene cluster (the gene cluster contained the aceB gene and the aceA gene), and recombinant *Escherichia coli* FA10 was obtained. The specific steps were as follows:

(3-a) Preparation of Host Bacteria Containing pKD46 Plasmid:

The pKD46 plasmid was transformed into the FA09 strain obtained in the previous step according to the method of the step (2) of Example 1 to obtain recombinant *Escherichia coli* FA09/pKD46 containing the plasmid pKD46, and then FA09/pKD46 competent cells were prepared.

(3-b) Preparation of Targeting Fragment aceBAup-Kan-$P_{CP41}$-aceBAdown:

Using pUC57-9K of the step (2) of Example 1 as a template, an aceBAup-kan-$P_{CP41}$-aceBAdown fragment was amplified using a primer aceBA-PF/aceBA-PR. The sequence of the aceBAup-kan-$P_{CP41}$-aceBAdown fragment was SEQ ID No. 42 in the sequence listing, and the fragment contained (a) a promoter upstream homologous arm aceBAup of the aceBA gene cluster, the nucleotide sequence of which was positions 1-51 of SEQ ID No. 42; (b) a kanamycin resistance gene (LOXP-kan-LOXP) flanked by LOXP, the nucleotide sequence of which was positions 52-1492 of SEQ ID No. 42; (c) an *Escherichia coli* constitutive promoter $P_{CP41}$, the nucleotide sequence of which was positions 1493-1670 of SEQ ID No. 42; and (d) a promoter downstream homologous arm aceBAdown of the aceBA gene cluster, the nucleotide sequence of which was positions 1671-1722 of SEQ ID No. 42.

(3-c) Homologous Recombination:

The above aceBAup-kan-$P_{CP41}$-aceBAdown fragment was electroporated into the FA09/pKD46 competent cells prepared in (3-a), the cells were placed in an LB plate containing kanamycin (concentration: 50 μg/ml) overnight at 37° C., and clones were selected. An aceBA-PIF/aceBA-PIR primer was used for PCR amplification and identification (an amplified target band of about 2,000 bp was positive, and an amplified target band of about 400 bp was negative), and the positive clones were selected and named FA10-kan. The primer binding positions were the upstream and downstream regions of the promoter of the aceBA gene cluster of *Escherichia coli* BW25113, respectively. The results of sequencing analysis indicate that the genome of FA10-kan contains the aceBAup-kan-$P_{CP41}$-aceBAdown fragment of the step (3-b).

(3-d) Elimination of Resistance:

The kanamycin resistance of FA10-kan was eliminated using the pCP20 plasmid according to the method of the step (2) of Example 1. The aceBA-PIF/aceBA-PIR primer was used for PCR amplification and identification (an amplified target band of about 600 bp was positive, and an amplified target band of about 2,000 or 400 bp was negative), and positive clones were selected and named FA10.

FA10 is a strain obtained by substituting the constitutive promoter $P_{CP41}$ for the promoter of the aceBA gene cluster of FA09. In FA09, the aceB gene in the aceBA gene cluster encodes the protein shown in SEQ ID No. 44, the coding sequence of the aceB gene is shown in SEQ ID No. 43, the aceA gene encodes the protein shown in SEQ ID No. 46, and the coding sequence of the aceA gene is shown in SEQ ID No. 45. The results of sequencing analysis indicate that the constitutive promoter $P_{CP41}$ is substituted for the promoter of aceBA gene cluster on the genome of FA10, and the expression of the aceB gene and the aceA gene in the aceBA gene cluster is initiated by the $P_{CP41}$.

(4) Construction of Plasmid Expressing *Escherichia coli* Aspartate Aminotransferase Gene aspC.

(4-a) Extraction of *Escherichia coli* Genomic DNA and PCR Amplification of aspC Gene.

The genomic DNA of *Escherichia coli* was extracted using a bacterial genome extraction kit (Tiangen Biotech Co., Ltd., product catalogue: DP302). Using the extracted total DNA of the *Escherichia coli* genome as a template and aspC-F and aspC-R as primers, PCR amplification was carried out using high-fidelity TransStart FastPfu DNA polymerase (Beijing TransGen Biotech Co., Ltd., product catalogue: AP221) to obtain a gene fragment aspC of the correct sequence.

(4-b) Construction of Recombinant Expression Vector Containing aspC Gene.

A vector pLB1a (the nucleotide sequence of the vector pLB1a was shown in SEQ ID No. 24) was digested with NcoI and XhoI, and a large fragment LB1a-NX of the vector was recovered. The gene fragment aspC with the correct sequence obtained in the above step was ligated with the LB1a-NX fragment by the Gibson assembly method. *Escherichia coli* DH5a competent cells were transformed by the CaCl$_2$) method. The cells were uniformly spread on an LB plate containing ampicillin and cultured overnight at 37° C. Clones were selected and identified by a primer F105-F/aspC-R. The positive clones with the correct sequence of the target fragment were selected, and the obtained positive recombinant plasmid was named pLB1a-aspC.

(5) Construction of Plasmid Expressing *Escherichia coli* Glutamate Dehydrogenase Gene gdhA Gene.

Genomic DNA was extracted from *Escherichia coli*, a gdhA gene fragment was amplified with a primer gdhA-F/gdhA-R, and the RBS sequence was introduced into the primer. A large fragment LB1a-aspC-XP was obtained by digesting the vector pLB1a-aspC with XhoI and SpeI. The gdhA gene fragment was ligated with the LB1a-aspC-XP fragment by the Gibson assembly method. *Escherichia coli* DH5a was transformed and identified by a primer gdhA-F/T58-R. Positive clones with the correct sequence of the target fragment were selected, and the obtained positive recombinant plasmid was named pLB1a-aspC-gdhA.

(6) Construction of Plasmid Expressing *Marinobacter hydrocarbonoclasticus* Exogenous Alkane Uptake Outer Membrane Protein Gene alkL Gene.

Genomic DNA was extracted from *Marinobacter hydrocarbonoclasticus*, the alkL gene fragment was amplified with a primer alkL-F"/alkL-R", and the RBS sequence was introduced into the primer. A large fragment LB1a-aspC-gdhA-PE was obtained by digesting the vector pLB1a-aspC-gdhA with SpeI and EcoRI. The alkL gene fragment was ligated with the LB1a-aspC-gdhA-PE fragment by the Gibson assembly method. *Escherichia coli* DH5a was transformed and identified by the primer alkL-F/T58-R. Positive clones with the correct sequence of the target fragment were selected, and the obtained positive recombinant plasmid was named pLB1a-aspC-gdhA-alkL.

The pLB1a-aspC-gdhA-alkL contains the aspC gene shown in SEQ ID No. 47, the gdhA gene shown in SEQ ID No. 49, and the DNA fragment (containing the alkL gene) shown in SEQ ID No. 28. The positions 2-7 of SEQ ID No. 49 are the sequence of RBS, and the positions 15-1358 of SEQ ID No. 49 are the sequence of the gdhA gene. The pLB1a-aspC-gdhA-alkL may express the aspC protein shown in SEQ ID No. 48, the gdhA protein shown in SEQ ID No. 50, and the alkL protein shown in SEQ ID No. 29.

(7) Construction of Plasmid Expressing *Tribolium castaneum* L-Aspartate-α-Decarboxylase Gene panD Gene.

The L-aspartate-α-decarboxylase gene panD gene of *Tribolium castaneum* was obtained by whole gene synthesis and ligated to the pUC57 vector to obtain a vector pUC57-panD. The nucleotide sequence of the panD gene was shown in SEQ ID No. 51. Using panD-F and panD-R as primers and vector pUC57-panD plasmid as a template, a panD gene fragment was amplified by PCR using high-fidelity TransStart FastPfu DNA polymerase. A vector pXB1k (the nucleotide sequence of the vector pXB1k was shown in SEQ ID No. 35) was digested with NcoI and XhoI, and a large fragment XB1k-NX of the vector was recovered. The panD gene fragment was ligated with the XB1k-NX fragment by the Gibson assembly method. *Escherichia coli* DH5a was transformed, the cells were spread on an LB plate containing kanamycin and cultured at 37° C. overnight, and clones were selected. A primer F105-F/panD-R was used for identification. The positive clones with the correct sequence of the target fragment were selected, plasmids were extracted, and the obtained positive recombinant plasmid was named pXB1k-panD. The pXB1k-panD contains the panD gene shown in SEQ ID No. 51 and may express the panD protein shown in SEQ ID No. 52.

(8) Construction of Recombinant *Escherichia coli* FA11.

Competent cells were prepared from the strain FA10 obtained in step (3), and the plasmids pLB1a-aspC-gdhA-alkL and pXB1k-panD were transformed into FA10 by the CaCl$_2$ method. The cells were spread on an LB plate containing ampicillin and kanamycin and cultured overnight at 37° C. Positive clones containing the pLB1a-aspC-gdhA-alkL and pXB1k-panD were selected and named FA11.

FA11 was a strain obtained by transforming *Escherichia coli* BW25113 as the following (c1)-(c14):

(c1) the fatty acid degradation transcription factor fadR gene was knocked out;

(c2) the *Escherichia coli* constitutive promoter $P_{CP41}$ was substituted for the fadL gene promoter;

(c3) the *Escherichia coli* constitutive promoter $P_{CP41}$ was substituted for the fadD gene promoter;

(c4) the *Escherichia coli* constitutive promoter $P_{CP41}$ was substituted for the sthA gene promoter;

(c5) the β-ketoacyl-ACP synthase II gene fabF gene was knocked out;

(c6) the β-ketoacyl-ACP synthase III gene fabH gene was knocked out;

(c7) the *Escherichia coli* constitutive promoter $P_{CP41}$ was substituted for the atoSC gene cluster promoter;

(c8) the glyoxylate pathway transcriptional repressor gene iclR gene was knocked out;

(c9) the α-ketoglutarate decarboxylase gene sucA gene was knocked out;

(c10) the *Escherichia coli* constitutive promoter $P_{CP41}$ was substituted for the aceBA gene cluster promoter;

(c11) the aspartate aminotransferase gene aspC gene was introduced;

(c12) the glutamate dehydrogenase gene gdhA gene was introduced;

(c13) the exogenous alkane uptake outer membrane protein gene alkL gene was introduced; and (c14) the L-aspartate-α-decarboxylase gene panD gene was introduced.

Competent cells were prepared from the strain FA10, and plasmids pLB1a and pXB1k were transformed into the FA10 by the CaCl$_2$) method. The cells were spread on an LB plate containing ampicillin and kanamycin and cultured overnight at 37° C. Positive clones containing pLB1a and pXB1k were selected and named FA00.

TABLE 4

Sequence listing of primers used in Example 4

| Primer | Sequence | Application |
|---|---|---|
| iclR-IF | 5'-CACTTGCTCCCGACACGCTCAACCC-3' | Step (1) |
| iclR-IR | 5'-TAAAAGTTTCGGTGGAATGAGATCT-3' | Step (1) |
| sucA-IF | 5'-GATAAGCGCAGCGCATCAGGCGTAA-3' | Step (2) |
| sucA-IR | 5'-TTCCAGAACCGCATCCAGAATGCCG-3' | Step (3) |
| aceBA-PF | 5'-CGTTAAGCGATTCAGCACCTTACCTCAGGCACCTTCGGGTGCCTTTTTTAGTCTCGAGAATATCCTCCTT-3' | Step (3) |
| aceBA-PR | 5'-TACGGCCTTGTGAAAGCCAGTTCATCGGTTGTTGTTGCCTGTTCAGTCATGGTATATCTCCTTCTTAAAA-3' | Step (3) |
| aceBA-PIF | 5'-AATGATCCGCAAAATACACCGCGAG-3' | Step (3) |
| aceBA-PIR | 5'-ATAAAATCAGGCAACGTTCCGTTAT-3' | Step (3) |
| aspC-F | 5'-GCTAACAGGAGGAATTAACCATGTTTGAGAACATTACCGCCGCTC-3' | Step (4) |
| aspC-R | 5'-CACTAGTACCAGATCTACCCTCGAGTTACAGCACTGCCACAATCGCTTCG-3' | Step (4) |
| gdhA-F | 5'-GATTGTGGCAGTGCTGTAACCAGGAGGAATTAACATGGATCAGACATATTCTCTGGAGT-3' | Step (5) |
| ghdA-R | 5'-CGAGCTCACCGAATTCACCACTAGTTTAAATCACACCCTGCGCCAGCATC-3' | Step (5) |
| alkL-F" | 5'-GGCGCAGGGTGTGATTTAAACAGGAGGAATTAACATGAAACCTAAAATCATTAGTAAAG-3' | Step (6) |
| alkL-R" | 5'-GCTGCAGACCGAGCTCACCGTTAAAAGCGATACGCAACGCCGATA-3' | Step (6) |
| panD-F | 5'-GCTAACAGGAGGAATTAACCATGCCAGCAACCGGTGAGGATCAGG-3' | Step (7) |
| panD-R | 5'-CACTAGTACCAGATCTACCCTCGAGCGATGCGGAAGAAGTTCGGATGGCC-3' | Step (7) |
| F105-F | 5'-TAGCATTTTTATCCATAAGATTAGC-3' | Steps (4, 7) |
| T58-R | 5'-TTTCACTTCTGAGTTCGGCATGGGG-3' | Steps (5, 6) |

II. Preparation of β-Alanine

1. Preparation of Media

F medium: The F medium was a sterile medium obtained by adding palmitic acid, a polyoxyethylene ether Brij58 emulsifier and vitamin B6 to the A medium of Example 2, where the mass percentage concentration of the palmitic acid was 0.5%, the mass percentage concentration of the polyoxyethylene ether Brij58 emulsifier was 0.2%, and the concentration of the vitamin B6 was 40 mg/L.

G medium: The G medium was a sterile medium obtained by adding palmitic acid, a polyoxyethylene ether Brij58 emulsifier, vitamin B6 and glutamic acid to the A medium of Example 2, where the mass percentage concentration of the palmitic acid was 1%, the mass percentage concentration of the polyoxyethylene ether Brij58 emulsifier was 0.2%, the concentration of the vitamin B6 was 10 mg/L, and the concentration of the glutamic acid was 2 mM.

2. Preparation of β-Alanine

The experiment was repeated for three times, and the specific steps of each experiment were as follows:

2.1. Culture of Bacterial Cells.

The strain FA11 obtained in the step I and cultured overnight was cultured according to the following method. The strain was inoculated into 20 ml of the A medium containing streptomycin and kanamycin (the concentration of both streptomycin and kanamycin was 50 mg/L) of Example 2 at an inoculum size of 1%, and cultured at 37° C. for 12 h to collect the bacterial cells; the collected cells were transferred to 20 ml of the F medium containing streptomycin and kanamycin (the concentration of both streptomycin and kanamycin was 50 mg/L), and cultured at 37° C. for 6 h to obtain a culture solution; the $OD_{600}$ of the culture solution was 6; an arabinose inducer was added to the culture solution to allow the mass percentage concentration of the arabinose inducer in the culture solution to be 0.2%, the cells were cultured at 37° C. for 12 h, and the cells were collected to obtain FA11 cells.

According to the above method, FA00 was cultured in the A medium and the F medium free of streptomycin and kanamycin to obtain FA00 cells.

2.2. Whole Cell Catalytic Production of β-Alanine.

30 mg (i.e., $1\times10^{11}$ cfu) by dry weight of the FA11 cells collected in the above step 2.1 were suspended in a shake flask containing 20 ml of the G medium and cultured at 37° C. for 24 h. Then a supernatant was collected after centrifugation and filtered by a 0.22 μm filter to obtain a filtrate, and the filtrate was an FA11 sample to be tested.

According to the above method, FA00 cells were substituted for FA11, and the other steps were unchanged, to obtain the FA00 sample to be tested.

Using β-alanine (Sigma, 05159-100G) as a standard, the content of β-alanine in each sample to be tested was quantitatively analyzed by HPLC using a standard curve method (external standard method).

Figure 3:
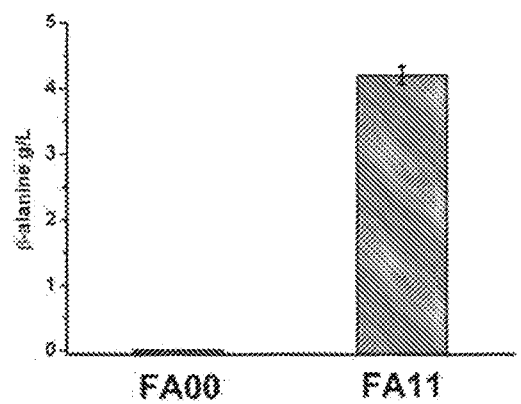
FIG. 3 shows production of β-alanine using FA11.

The quantitative test results are shown in FIG. 3. The average content of β-alanine in the FA11 sample to be tested is 4.2 g/L (i.e., 4.2 g/$5\times10^{12}$ cfu), and the mass percentage concentration of palmitic acid is 0.31%. The average content of β-alanine in the FA00 sample to be tested is 0 g/L, and the mass percentage concentration of palmitic acid is 0.90%. The conversion rate of β-alanine prepared with palmitic acid as a substrate using FA11 is 60.87%, and β-alanine could not be obtained using FA00. It is indicated that β-alanine may be prepared using FA11.

INDUSTRIAL APPLICATION

The present invention synthesizes 3-hydroxypropionic acid from a fatty acid as a raw material, and the theoretical conversion rate reaches 217.86%, which is significantly higher than that from glucose (the theoretical conversion rate is 100%). The present invention also prepares recombinant bacteria for producing the 3-hydroxypropionic acid from a fatty acid as a raw material. The recombinant bacteria may be used to produce 3-hydroxypropionic acid by microbial fermentation and biotransformation using a fatty acid raw material obtained from crude oil processing products, waste oil, or the like at a low price. Therefore, the use of the fatty acid raw material to synthesize 3-hydroxypropionic acid has a potential cost advantage. The conversion rate of 3-hydroxypropionic acid produced by using the recombinant bacteria of the present invention from a fatty acid as a raw material is 28.37%, indicating that 3-hydroxypropionic acid may be produced using the recombinant bacteria of the present invention.

What is claimed is:

1. A recombinant bacteria that contains a fadR gene, a fabF gene, and a fabH gene, the bacteria comprising a genetic modification that increases content of a protein encoded by a malonyl-CoA reductase gene mcr gene and/or that enhances activity of the protein encoded by the mcr gene.

2. A preparation method for 3-hydroxypropionic acid, comprising: bio-transforming the recombinant bacteria according to claim 1 with fatty acid as a substrate to prepare the 3-hydroxypropionic acid.

3. The method according to claim 2, wherein the fatty acid is palmitic acid, stearic acid, myristic acid, lauric acid, capric acid, octanoic acid and/or hexanoic acid.

4. A method of producing 3-hydroxypropionic acid comprising obtaining the recombinant bacteria according to claim 1 and exposing the recombinant bacteria to a fatty acid to produce the 3-hydroxypropionic acid.

5. A method of degrading fatty acid comprising obtaining a recombinant bacteria according to claim 1.

6. A method of preparing a product for degrading a fatty acid comprising obtaining a recombinant bacteria according to claim 1.

7. The recombinant bacteria according to claim 1, further comprising all or part of A1 through A5:
A1. a knocked out fatty acid degradation transcription factor fadR gene or a modification that inhibits expression of the fadR gene or inhibits activity of a protein encoded by the fadR gene;
A2. a knocked out a β-ketoacyl-ACP synthase II gene fabF gene or a modification that inhibits expression of the fabF gene or inhibits activity of a protein encoded by the fabF gene;
A3. a knocked out a β-ketoacyl-ACP synthase III gene fabH gene or a modification that inhibits expression of the fabH gene or inhibits activity of a protein encoded by the fabH gene;
A4. a modification that increases content of a protein encoded by an acetyl-CoA carboxylase acc gene or gene cluster and/or that enhances activity of the protein encoded by the acc gene or gene cluster; or
A5. a modification that increases content of a protein encoded by an exogenous alkane uptake outer membrane protein gene alkL gene and/or that enhances activity of the protein encoded by the alkL gene.

8. A method of constructing the recombinant bacteria according to claim 1, comprising: modifying a recipient bacteria by
increasing the content of the protein encoded by a malonyl-CoA reductase gene mcr gene in the recipient bacteria or/and enhancing activity of the protein encoded by the mcr gene;
the recipient bacteria being bacteria containing the fadR gene, the fabF gene, and the fabH gene.

9. The method according to claim 8, wherein the recipient bacteria is selected from the group consisting of:
1) *Escherichia coli*; and
2) *Escherichia coli* BW25113.

10. The method according to claim 8 wherein the acc gene or gene cluster is derived from *Corynebacterium glutamicum* or/and *Rhodococcus opacus*;
the alkL gene is derived from *Marinobacter hydrocarbonoclasticus* or/and *Pseudomonas putida*; and
the mcr gene is derived from *Chloroflexus aurantiacus*.

11. The method according to claim 8, wherein:
the fadR gene encodes a protein of the following a1) or a2):
a1) a protein shown in SEQ ID No. 2 in a sequence listing; and
a2) a protein having a same function obtained by substitution and/or deletion and/or addition of one or more amino acid residues in an amino acid sequence of SEQ ID No. 2 in the sequence listing;
the fabF gene encodes a protein of the following a3) or a4):
a3) a protein shown in SEQ ID No. 14 in the sequence listing; and
a4) a protein having a same function obtained by substitution and/or deletion and/or addition of one or more amino acid residues in an amino acid sequence of SEQ ID No. 14 in the sequence listing;
the fabH gene encodes a protein of the following a5) or a6):
a5) a protein shown in SEQ ID No. 16 in the sequence listing; and
a6) a protein having a same function obtained by substitution and/or deletion and/or addition of one or more amino acid residues in an amino acid sequence of SEQ ID No. 16 in the sequence listing;
the acc gene or gene cluster encodes proteins of the following a7) and a8):
a7) the following a71) or a72):
a71) a protein shown in SEQ ID No. 26 in the sequence listing; and
a72) a protein having a same function obtained by substitution and/or deletion and/or addition of one or more amino acid residues in an amino acid sequence of SEQ ID No. 26 in the sequence listing;
a8) the following a81) or a82):
a81) a protein shown in SEQ ID No. 27 in the sequence listing; and
a82) a protein having a same function obtained by substitution and/or deletion and/or addition of one or more amino acid residues in an amino acid sequence of SEQ ID No. 27 in the sequence listing;
the alkL gene encodes a protein of the following a9) or a10):
a9) a protein shown in SEQ ID No. 29 in the sequence listing; and
a10) a protein having a same function obtained by substitution and/or deletion and/or addition of one or more amino acid residues in an amino acid sequence of SEQ ID No. 29 in the sequence listing; and
the mcr gene encodes a protein of the following a11) or a12):
a11) a protein shown in SEQ ID No. 37 in the sequence listing; and
a12) a protein having a same function obtained by substitution and/or deletion and/or addition of one or more amino acid residues in an amino acid sequence of SEQ ID No. 37 in the sequence listing.

12. The method according to claim 8, wherein:
A4 is achieved by introducing the acc gene or gene cluster into the recipient bacteria;
A5 is achieved by introducing the alkL gene into the recipient bacteria; and
A6 is achieved by introducing the mcr gene into the recipient bacteria.

13. The method according to claim 8, wherein:
the fadR gene is the following b1) or b2):
b1) a cDNA molecule or DNA molecule shown in SEQ ID No. 1 in the sequence listing; and b2) a cDNA molecule or genomic DNA molecule having 75% or higher identity with a nucleotide sequence defined by b1) and having a same function;

the fabF gene is the following b3) or a4):
b3) a cDNA molecule or DNA molecule shown in SEQ ID No. 13 in the sequence listing; and
b4) a cDNA molecule or genomic DNA molecule having 75% or higher identity with a nucleotide sequence defined by b3) and having a same function;

the fabH gene is the following b5) or b6):
b5) a cDNA molecule or DNA molecule shown in SEQ ID No. 15 in the sequence listing; and
b6) a cDNA molecule or genomic DNA molecule having 75% or higher identity with a nucleotide sequence defined by b5) and having a same function;

the acc gene or gene cluster is the following b7) or b8):
b7) a cDNA molecule or DNA molecule shown in positions 15-3259 of SEQ ID No. 25 in the sequence listing; and
b8) a cDNA molecule or genomic DNA molecule having 75% or higher identity with a nucleotide sequence defined by b7) and having a same function;

the alkL gene is the following b9) or b10):
b9) a cDNA molecule or DNA molecule shown in SEQ ID No. 28 in the sequence listing; and
b10) a cDNA molecule or genomic DNA molecule having 75% or higher identity with a nucleotide sequence defined by b9) and having a same function; and the mcr gene is the following b11) or b12):
b11) a cDNA molecule or DNA molecule shown in SEQ ID No. 36 in the sequence listing; and
b12) a cDNA molecule or genomic DNA molecule having 75% or higher identity with a nucleotide sequence defined by b11) and having a same function.

14. The method according to claim 8, wherein the method further comprises one or more the following B1-B4:
B1. increasing content of a protein encoded by a fadL gene in the recipient bacteria or/and enhancing activity of the protein encoded by the fadL gene;
B2. increasing content of a protein encoded by a gene in a fatty acid β oxidation pathway in the recipient bacteria or/and enhancing activity of the protein encoded by the gene in the fatty acid β oxidation pathway;
the gene in the fatty acid β oxidation pathway being selected from one or more of the following genes: a fadD gene encoding fatty acyl-CoA synthase, a fadE gene encoding fatty acyl-CoA dehydrogenase, a fadB gene encoding 3-hydroxyacyl-CoA dehydrogenase, a fadA gene encoding 3-ketoacyl-CoA thiolase, a fadI gene encoding 3-ketoacyl-CoA thiolase, a fadJ gene encoding 3-hydroxyacyl-CoA dehydrogenase and a fadK gene encoding short-chain fatty acyl-CoA synthase;
B3. increasing content of a protein encoded by a sthA gene in the recipient bacteria or/and enhancing activity of the protein encoded by the sthA gene; and
B4. increasing content of a protein encoded by a gene in a short-chain fatty acid degradation pathway in the recipient bacteria or/and enhancing activity of the protein encoded by the gene in the short-chain fatty acid degradation pathway;
wherein the gene in the short-chain fatty acid degradation pathway is B4a or B4b:
B4a. a gene in a short-chain fatty acid degradation regulatory gene cluster atoSC gene cluster; and
B4b. a gene in a short-chain fatty acid degradation gene cluster atoDAEB gene cluster.

15. The method according to claim 14, wherein the gene in the short-chain fatty acid egradation regulatory gene cluster atoSC gene cluster is a gene atoC gene encoding an atoC transcription activator and/or a gene atoS gene encoding atoS-sensing histidine kinase; and the gene in the short-chain fatty acid degradation gene cluster atoDAEB gene cluster is a gene atoA gene encoding an acetoacetyl-CoA transferase α subunit, a gene atoD gene encoding an acetoacetyl-CoA transferase β subunit, a gene atoE gene encoding an acetoacetic acid transport protein, and/or a gene atoB gene encoding an acetyl-CoA acetyltransferase.

16. The method according to claim 14, wherein:
the fadL gene encodes a protein of the following a17) or a18):
a17) a protein shown in SEQ ID No. 6 in the sequence listing; and
a18) a protein having a same function obtained by substitution and/or deletion and/or addition of one or more amino acid residues in an amino acid sequence of SEQ ID No. 6 in the sequence listing;
the fadD gene encodes a protein of the following a19) or a20):
a19) a protein shown in SEQ ID No. 9 in the sequence listing; and
a20) a protein having a same function obtained by substitution and/or deletion and/or addition of one or more amino acid residues in an amino acid sequence of SEQ ID No. 9 in the sequence listing;
the sthA gene encodes a protein of the following a21) or a22):
a21) a protein shown in SEQ ID No. 12 in the sequence listing; and
a22) a protein having a same function obtained by substitution and/or deletion and/or addition of one or more amino acid residues in an amino acid sequence of SEQ ID No. 12 in the sequence listing; and
the atoSC gene cluster encodes proteins of the following a23) and a24):
a23) a protein of the following a231) or a232):
a231) a protein shown in SEQ ID No. 19 in the sequence listing; and
a232) a protein having a same function obtained by substitution and/or deletion and/or addition of one or more amino acid residues in an amino acid sequence of SEQ ID No. 19 in the sequence listing; and
a24) a protein of the following a241) or a242):
a241) a protein shown in SEQ ID No. 21 in the sequence listing; and
a242) a protein having a same function obtained by substitution and/or deletion and/or addition of one or more amino acid residues in an amino acid sequence of SEQ ID No. 21 in the sequence listing.

17. The method according to claim 14, wherein:
B1 is achieved by substituting a promoter $P_{CP41}$ for a promoter of the fadL gene;
B2 is achieved by substituting the promoter $P_{CP41}$ for a promoter of the gene in the fatty acid β oxidation pathway;
B3 is achieved by substituting the promoter $P_{CP41}$ for a promoter of the sthA gene; and
B4 is achieved by substituting the promoter $P_{CP41}$ for a promoter of the gene in the short chain fatty acid degradation pathway.

18. The method according to claim 17, wherein the promoter $P_{CPA1}$ is a nucleic acid molecule of the following 1) or 2) or 3):
1) a DNA molecule with a coding sequence comprising positions 1443-1622 of SEQ ID No. 3 in the sequence listing;
2) a DNA molecule having 75% or higher identity with a nucleotide sequence defined by 1) and having a same function; and
3) a DNA molecule hybridizing to the nucleotide sequence defined by 1) under a stringent condition and having a same function.

19. The method according to claim 8, wherein the method further comprises all or part of the following A1 through A5:
A1. knocking out a fatty acid degradation transcription factor fadR gene of the recipient bacteria or inhibiting expression of the fadR gene or inhibiting activity of a protein encoded by the fadR gene;
A2. knocking out a β-ketoacyl-ACP synthase II gene fabF gene of the recipient bacteria or inhibiting expression of the fabF gene or inhibiting activity of a protein encoded by the fabF gene;
A3. knocking out a β-ketoacyl-ACP synthase III gene fabH gene of the recipient bacteria or inhibiting expression of the fabH gene or inhibiting activity of a protein encoded by the fabH gene;
A4. increasing content of a protein encoded by an acetyl-CoA carboxylase acc gene or gene cluster in the recipient bacteria or/and enhancing activity of the protein encoded by the acc gene or gene cluster; or
A5. increasing content of a protein encoded by an exogenous alkane uptake outer membrane protein gene alkL gene in the recipient bacteria or/and enhancing activity of the protein encoded by the alkL gene.

* * * * *

SEQUENCE LISTING

```
<160> NUMBER OF SEQ ID NOS: 52

<210> SEQ ID NO 1
<211> LENGTH: 720
<212> TYPE: DNA
<213> ORGANISM: Artificial sequence
<220> FEATURE:
<223> OTHER INFORMATION: synthetic nucleotide

<400> SEQUENCE: 1
atggtcatta aggcgcaaag cccggcgggt ttcgcggaag agtacattat tgaaagtatc      60
tggaataacc gcttccctcc cgggactatt ttgcccgcag aacgtgaact ttcagaatta     120
attggcgtaa cgcgtactac gttacgtgaa gtgttacagc gtctggcacg agatggctgg     180
ttgaccattc aacatggcaa gccgacgaag gtgaataatt tctgggaaac ttccggttta     240
aatatccttg aaacactggc gcgactggat cacgaaagtg tgccgcagct tattgataat     300
ttgctgtcgg tgcgtaccaa tatttccact attttttattc gcaccgcgtt tcgtcagcat     360
cccgataaag cgcaggaagt gctggctacc gctaatgaag tggccgatca cgccgatgcc     420
tttgccgagc tggattacaa catattccgc ggcctggcgt ttgcttccgg caacccgatt     480
tacggtctga ttcttaacgg gatgaaaggg ctgtatacgc gtattggtcg tcactatttc     540
gccaatccgg aagcgcgcag tctggcgctg ggcttctacc acaaactgtc ggcgttgtgc     600
agtgaaggcg cgcacgatca ggtgtacgaa acagtgcgtc gctatgggca tgagagtggc     660
gagatttggc accggatgca gaaaaatctg ccgggtgatt tagccattca ggggcgataa     720

<210> SEQ ID NO 2
<211> LENGTH: 239
<212> TYPE: PRT
<213> ORGANISM: Artificial sequence
<220> FEATURE:
```

<223> OTHER INFORMATION: synthetic peptide

<400> SEQUENCE: 2

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
            85                  90                  95

Leu Ile Asp Asn Leu Leu Ser Val Arg Thr Asn Ile Ser Thr Ile Phe
        100                 105                 110

Ile Arg Thr Ala Phe Arg Gln His Pro Asp Lys Ala Gln Glu Val Leu
    115                 120                 125

Ala Thr Ala Asn Glu Val Ala Asp His Ala Asp Ala Phe Ala Glu Leu
130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
            165                 170                 175

Arg His Tyr Phe Ala Asn Pro Glu Ala Arg Ser Leu Ala Leu Gly Phe
        180                 185                 190

Tyr His Lys Leu Ser Ala Leu Cys Ser Glu Gly Ala His Asp Gln Val
    195                 200                 205

Tyr Glu Thr Val Arg Arg Tyr Gly His Glu Ser Gly Glu Ile Trp His
210                 215                 220

Arg Met Gln Lys Asn Leu Pro Gly Asp Leu Ala Ile Gln Gly Arg
225                 230                 235
```

<210> SEQ ID NO 3
<211> LENGTH: 1622
<212> TYPE: DNA
<213> ORGANISM: Artificial sequence
<220> FEATURE:
<223> OTHER INFORMATION: synthetic nucleotide

<400> SEQUENCE: 3

```
gtctcgagaa tatcctcctt ataacttcgt ataatgtatg ctatacgaac ggtaagagcg    60
cttttgaagc tggggtgggc gaagaactcc agcatgagat ccccgcgctg gaggatcatc   120
cagccggcgt cccggaaaac gattccgaag cccaaccttt catagaaggc ggcggtggaa   180
tcgaaatctc gtgatggcag gttggcgtc gcttggtcgg tcatttggaa ccccagagtc   240
ccgctcagaa gaactcgtca agaaggcgat agaaggcgat gcgctgcgaa tcgggagcgg   300
cgataccgta agcacgagg aagcggtcag cccattcgcc gccaagctct tcagcaatat   360
cacgggtagc caacgctatg tcctgatagc ggtccgccac acccagccgg ccacagtcga   420
tgaatccaga aaagcggcca ttttccacca tgatattcgg caagcaggca tcgccatggg   480
tcacgacgag atcctcgccg tcgggcatgc gcgccttgag cctggcgaac agttcggctg   540
gcgcgagccc ctgatgctct tcgtccagat catcctgatc gacaagaccg gcttccatcc   600
```

```
gagtacgtgc tcgctcgatg cgatgtttcg cttggtggtc gaatgggcag gtagccggat      660
caagcgtatg cagccgccgc attgcatcag ccatgatgga tactttctcg gcaggagcaa      720
ggtgagatga caggagatcc tgccccggca cttcgcccaa tagcagccag tcccttcccg      780
cttcagtgac aacgtcgagc acagctgcgc aaggaacgcc cgtcgtggcc agccacgata      840
gccgcgctgc ctcgtcctgc agttcattca gggcaccgga caggtcggtc ttgacaaaaa      900
gaaccgggcg cccctgcgct gacagccgga acacggcggc atcagagcag ccgattgtct      960
gttgtgccca gtcatagccg aatagcctct ccacccaagc ggccggagaa cctgcgtgca     1020
atccatcttg ttcaatcatg cgaaacgatc ctcatcctgt ctcttgatca gatcttgatc     1080
ccctgcgcca tcagatcctt ggcggcaaga aagccatcca gtttactttg cagggcttcc     1140
caaccttacc agagggcgcc ccagctggca attccggttc gcttgctgtc cataaaaccg     1200
cccagtctag ctatcgccat gtaagcccac tgcaagctac ctgctttctc tttgcgcttg     1260
cgttttccct tgtccagata gcccagtagc tgacattcat ccggggtcag caccgttttct     1320 gcggactggc tttctacgtg ttccgcttcc tttagcagcc cttgcgccct gagtgcttgc     1380
ggcagcgtga ggggatcttt accgttcgta taatgtatgc ataccaagt tatgaagcta      1440 gcttatcaaa aagagtattg acataaagtc taacctatag ataattacag ccatcgagag     1500
ggacacggcg atttgctgtc accggatgtg cttccggtc tgatgagtcc gtgaggacga      1560
aacagcctct acaaataatt ttgtttaaga attcaaaaga tcttttaaga aggagatata     1620
cc                                                                    1622
```

<210> SEQ ID NO 4
<211> LENGTH: 1722
<212> TYPE: DNA
<213> ORGANISM: Artificial sequence
<220> FEATURE:
<223> OTHER INFORMATION: synthetic nucleotide

<400> SEQUENCE: 4

```
cttaaaaatg atctaaaaca aaattcaccc gaatccatga gtgcgccacc gtctcgagaa       60
tatcctcctt ataacttcgt ataatgtatg ctatacgaac ggtaagagcg cttttgaagc      120
tggggtgggc gaagaactcc agcatgagat ccccgcgctg gaggatcatc agccggcgt      180 cccggaaaac gattccgaag cccaaccttt catagaaggc ggcggtggaa tcgaaatctc      240
gtgatggcag gttgggcgtc gcttggtcgg tcatttggaa cccagagtc ccgctcagaa      300 gaactcgtca agaaggcgat agaaggcgat gcgctgcgaa tcgggagcgg cgataccgta      360
aagcacgagg aagcggtcag cccattcgcc gccaagctct tcagcaatat cacgggtagc      420
caacgctatg tcctgatagc ggtccgccac acccagccgg ccacagtcga tgaatccaga      480
aaagcggcca ttttccacca tgatattcgg caagcaggca tcgccatggg tcacgacgag      540
atcctcgccg tcgggcatgc gcgccttgag cctggcgaac agttcggctg gcgcgagccc     600
ctgatgctct tcgtccagat catcctgatc gacaagaccg gcttccatcc gagtacgtgc      660
tcgctcgatg cgatgtttcg cttggtggtc gaatgggcag gtagccggat caagcgtatg      720
cagccgccgc attgcatcag ccatgatgga tactttctcg gcaggagcaa ggtgagatga      780
caggagatcc tgccccggca cttcgcccaa tagcagccag tcccttcccg cttcagtgac      840
aacgtcgagc acagctgcgc aaggaacgcc cgtcgtggcc agccacgata gccgcgctgc      900
ctcgtcctgc agttcattca gggcaccgga caggtcggtc ttgacaaaaa gaaccgggcg      960
cccctgcgct gacagccgga acacggcggc atcagagcag ccgattgtct gttgtgccca     1020
```

```
gtcatagccg aatagcctct ccacccaagc ggccggagaa cctgcgtgca atccatcttg    1080
ttcaatcatg cgaaacgatc ctcatcctgt ctcttgatca gatcttgatc ccctgcgcca    1140
tcagatcctt ggcggcaaga aagccatcca gtttactttg cagggcttcc caaccttacc    1200
agagggcgcc ccagctggca attccggttc gcttgctgtc cataaaaccg cccagtctag    1260
ctatcgccat gtaagcccac tgcaagctac ctgctttctc tttgcgcttg cgttttccct    1320
tgtccagata gcccagtagc tgacattcat ccggggtcag caccgtttct gcggactggc    1380
tttctacgtg ttccgcttcc tttagcagcc cttgcgccct gagtgcttgc ggcagcgtga    1440
ggggatcttt accgttcgta taatgtatgc tataccaagt tatgaagcta gcttatcaaa    1500
aagagtattg acataaagtc taacctatag ataattacag ccatcgagag ggacacggcg    1560
atttgctgtc accggatgtg ctttccggtc tgatgagtcc gtgaggacga aacagcctct    1620
acaaataatt ttgtttaaga attcaaaaga tcttttaaga aggagatata ccatggtcat    1680
gagccagaaa accctgttta caaagtctgc tctcgcagtc gc                       1722

<210> SEQ ID NO 5
<211> LENGTH: 1347
<212> TYPE: DNA
<213> ORGANISM: Artificial sequence
<220> FEATURE:
<223> OTHER INFORMATION: synthetic nucleotide

<400> SEQUENCE: 5
atggtcatga gccagaaaac cctgtttaca aagtctgctc tcgcagtcgc agtggcactt      60
atctccaccc aggcctggtc ggcaggcttt cagttaaacg aattttcttc ctctggcctg     120
ggccgggctt attcagggga aggcgcaatt gccgatgatg caggtaacgt cagccgtaac     180
cccgcattga ttactatgtt tgaccgcccg acattttctg cgggtgcggt ttatattgac     240
ccggatgtaa atatcagcgg aacgtctcca tctggtcgta gcctgaaagc cgataacatc     300
gcgcctacgg catgggttcc gaacatgcac tttgttgcac cgattaacga ccaatttggt     360
tggggcgctt ctattacctc taactatggt ctggctacag agtttaacga tacttatgca     420
ggcggctctg tcgggggtac aaccgacctt gaaaccatga acctgaactt aagcggtgcg     480
tatcgcttaa ataatgcatg gagctttggt cttggtttca acgccgtcta cgctcgcgcg     540
aaaattgaac gtttcgcagg cgatctgggg cagttggttg ctggccaaat tatgcaatct     600
cctgctggcc aaactcagca agggcaagca ttggcagcta ccgccaacgg tattgacagt     660
aataccaaaa tcgctcatct gaacggtaac cagtgggggct ttggctggaa cgccggaatc     720
ctgtatgaac tggataaaaa taaccgctat gcactgacct accgttctga agtgaaaatt     780
gacttcaaag gtaactacag cagcgatctt aatcgtgcgt ttaataacta cggtttgcca     840
attcctaccg cgacaggtgg cgcaacgcaa tcgggttatc tgacgctgaa cctgcctgaa     900
atgtgggaag tgtcaggtta accgtgttt gatccacagt gggcgattca ctatagcctg     960
gcttacacca gctggagtca gttccagcag ctgaaagcga cctcaaccag tggcgacacg    1020
ctgttccaga acatgaaggg ctttaaagat gcttaccgca tcgcgttggg taccacttat    1080
tactacgatg ataactggac cttccgtacc ggtatcgcct tgatgacag cccagttcct    1140 gcacagaatc gttctatctc cattccggac caggaccgtt tctggctgag tgcaggtacg    1200
acttacgcat taataaaga tgcttcagtc gacgttggtg tttcttatat gcacggtcag    1260
agcgtgaaaa ttaacgaagg cccataccag ttcgagtctg aaggtaaagc ctggctgttc    1320
```
ggtactaact ttaactacgc gttctga 1347

<210> SEQ ID NO 6
<211> LENGTH: 448
<212> TYPE: PRT
<213> ORGANISM: Artificial sequence
<220> FEATURE:
<223> OTHER INFORMATION: synthetic peptide

<400> SEQUENCE: 6

```
Met Val Met Ser Gln Lys Thr Leu Phe Thr Lys Ser Ala Leu Ala Val
1               5                   10                  15

Ala Val Ala Leu Ile Ser Thr Gln Ala Trp Ser Ala Gly Phe Gln Leu
            20                  25                  30

Asn Glu Phe Ser Ser Ser Gly Leu Gly Arg Ala Tyr Ser Gly Glu Gly
        35                  40                  45

Ala Ile Ala Asp Asp Ala Gly Asn Val Ser Arg Asn Pro Ala Leu Ile
    50                  55                  60

Thr Met Phe Asp Arg Pro Thr Phe Ser Ala Gly Ala Val Tyr Ile Asp
65                  70                  75                  80

Pro Asp Val Asn Ile Ser Gly Thr Ser Pro Ser Gly Arg Ser Leu Lys
                85                  90                  95

Ala Asp Asn Ile Ala Pro Thr Ala Trp Val Pro Asn Met His Phe Val
            100                 105                 110

Ala Pro Ile Asn Asp Gln Phe Gly Trp Gly Ala Ser Ile Thr Ser Asn
        115                 120                 125

Tyr Gly Leu Ala Thr Glu Phe Asn Asp Thr Tyr Ala Gly Gly Ser Val
    130                 135                 140

Gly Gly Thr Thr Asp Leu Glu Thr Met Asn Leu Asn Leu Ser Gly Ala
145                 150                 155                 160

Tyr Arg Leu Asn Asn Ala Trp Ser Phe Gly Leu Gly Phe Asn Ala Val
                165                 170                 175

Tyr Ala Arg Ala Lys Ile Glu Arg Phe Ala Gly Asp Leu Gly Gln Leu
            180                 185                 190

Val Ala Gly Gln Ile Met Gln Ser Pro Ala Gly Gln Thr Gln Gln Gly
        195                 200                 205

Gln Ala Leu Ala Ala Thr Ala Asn Gly Ile Asp Ser Asn Thr Lys Ile
    210                 215                 220

Ala His Leu Asn Gly Asn Gln Trp Gly Phe Gly Trp Asn Ala Gly Ile
225                 230                 235                 240

Leu Tyr Glu Leu Asp Lys Asn Asn Arg Tyr Ala Leu Thr Tyr Arg Ser
                245                 250                 255

Glu Val Lys Ile Asp Phe Lys Gly Asn Tyr Ser Ser Asp Leu Asn Arg
            260                 265                 270

Ala Phe Asn Asn Tyr Gly Leu Pro Ile Pro Thr Ala Thr Gly Gly Ala
        275                 280                 285

Thr Gln Ser Gly Tyr Leu Thr Leu Asn Leu Pro Glu Met Trp Glu Val
    290                 295                 300

Ser Gly Tyr Asn Arg Val Asp Pro Gln Trp Ala Ile His Tyr Ser Leu
305                 310                 315                 320

Ala Tyr Thr Ser Trp Ser Gln Phe Gln Gln Leu Lys Ala Thr Ser Thr
                325                 330                 335

Ser Gly Asp Thr Leu Phe Gln Lys His Glu Gly Phe Lys Asp Ala Tyr
            340                 345                 350

Arg Ile Ala Leu Gly Thr Thr Tyr Tyr Tyr Asp Asp Asn Trp Thr Phe
```

|  |  | 355 |  |  |  | 360 |  |  |  | 365 |  |
|---|---|---|---|---|---|---|---|---|---|---|---|

Arg Thr Gly Ile Ala Phe Asp Asp Ser Pro Val Pro Ala Gln Asn Arg
    370                  375                380

Ser Ile Ser Ile Pro Asp Gln Asp Arg Phe Trp Leu Ser Ala Gly Thr
385                  390                395                400

Thr Tyr Ala Phe Asn Lys Asp Ala Ser Val Asp Val Gly Val Ser Tyr
                405                410                415

Met His Gly Gln Ser Val Lys Ile Asn Glu Gly Pro Tyr Gln Phe Glu
        420                  425                430

Ser Glu Gly Lys Ala Trp Leu Phe Gly Thr Asn Phe Asn Tyr Ala Phe
            435                440                445

<210> SEQ ID NO 7
<211> LENGTH: 1722
<212> TYPE: DNA
<213> ORGANISM: Artificial sequence
<220> FEATURE:
<223> OTHER INFORMATION: synthetic nucleotide

<400> SEQUENCE: 7

| | | | | | |
|---|---|---|---|---|---|
| tacggtaaag | ataaaaataa | atagtgacgc | gcttcgcaac | cttttcgttg | gtctcgagaa | 60 |
| tatcctcctt | ataacttcgt | ataatgtatg | ctatacgaac | ggtaagagcg | cttttgaagc | 120 |
| tggggtgggc | gaagaactcc | agcatgagat | ccccgcgctg | gaggatcatc | agccggcgt | 180 |
| cccggaaaac | gattccgaag | cccaaccttt | catagaaggc | ggcggtggaa | tcgaaatctc | 240 |
| gtgatggcag | gttgggcgtc | gcttggtcgg | tcatttggaa | ccccagagtc | ccgctcagaa | 300 |
| gaactcgtca | agaaggcgat | agaaggcgat | gcgctgcgaa | tcgggagcgg | cgataccgta | 360 |
| aagcacgagg | aagcggtcag | cccattcgcc | gccaagctct | tcagcaatat | cacgggtagc | 420 |
| caacgctatg | tcctgatagc | ggtccgccac | acccagccgg | ccacagtcga | tgaatccaga | 480 |
| aaagcggcca | ttttccacca | tgatattcgg | caagcaggca | tcgccatggg | tcacgacgag | 540 |
| atcctcgccg | tcgggcatgc | gcgccttgag | cctggcgaac | agttcggctg | gcgcgagccc | 600 |
| ctgatgctct | tcgtccagat | catcctgatc | gacaagaccg | gcttccatcc | gagtacgtgc | 660 |
| tcgctcgatg | cgatgtttcg | cttggtggtc | gaatgggcag | gtagccggat | caagcgtatg | 720 |
| cagccgccgc | attgcatcag | ccatgatgga | tactttctcg | gcaggagcaa | ggtgagatga | 780 |
| caggagatcc | tgccccggca | cttcgcccaa | tagcagccaa | tcccttcccg | cttcagtgac | 840 |
| aacgtcgagc | acagctgcgc | aaggaacgcc | cgtcgtggcc | agccacgata | gccgcgctgc | 900 |
| ctcgtcctgc | agttcattca | gggcaccgga | caggtcggtc | ttgacaaaaa | gaaccgggcg | 960 |
| cccctgcgct | gacagccgga | acacggcggc | atcagagcag | ccgattgtct | gttgtgccca | 1020 |
| gtcatagccg | aatagcctct | ccacccaagc | ggccggagaa | cctgcgtgca | atccatcttg | 1080 |
| ttcaatcatg | cgaaacgatc | ctcatcctgt | ctcttgatca | gatcttgatc | ccctgcgcca | 1140 |
| tcagatcctt | ggcggcaaga | aagccatcca | gtttactttg | cagggcttcc | caaccttacc | 1200 |
| agagggcgcc | ccagctggca | attccggttc | gcttgctgtc | cataaaaccg | cccagtctag | 1260 |
| ctatcgccat | gtaagcccac | tgcaagctac | ctgctttctc | tttgcgcttg | cgttttccct | 1320 |
| tgtccagata | gcccagtagc | tgacattcat | ccggggtcag | caccgtttct | gcggactggc | 1380 |
| tttctacgtg | ttccgcttcc | tttagcagcc | cttgcgccct | gagtgcttgc | ggcagcgtga | 1440 |
| ggggatcttt | accgttcgta | taatgtatgc | tataccaagt | tatgaagcta | gcttatcaaa | 1500 |
| aagagtattg | acataaagtc | taacctatag | ataattacag | ccatcgagag | ggacacggcg | 1560 |

```
atttgctgtc accggatgtg ctttccggtc tgatgagtcc gtgaggacga aacagcctct   1620
acaaataatt ttgtttaaga attcaaaaga tcttttaaga aggagatata ccttgaagaa   1680
ggtttggctt aaccgttatc cgcggacgt tccgacggag at                      1722

<210> SEQ ID NO 8
<211> LENGTH: 1686
<212> TYPE: DNA
<213> ORGANISM: Artificial sequence
<220> FEATURE:
<223> OTHER INFORMATION: synthetic nucleotide

<400> SEQUENCE: 8
ttgaagaagg tttggcttaa ccgttatccc gcggacgttc cgacggagat caaccctgac     60
cgttatcaat ctctggtaga tatgtttgag cagtcggtcg cgcgctacgc cgatcaacct    120
gcgtttgtga atatggggga ggtaatgacc ttccgcaagc tggaagaacg cagtcgcgcg    180
tttgccgctt atttgcaaca agggttgggg ctgaagaaag cgatcgcgt tgcgttgatg     240 atgcctaatt tattgcaata tccggtggcg ctgtttggca ttttgcgtgc cgggatgatc    300
gtcgtaaacg ttaacccgtt gtataccccg cgtgagcttg agcatcagct taacgatagc    360
ggcgcatcgg cgattgttat cgtgtctaac tttgctcaca cactggaaaa agtggttgat    420
aaaaccgccg ttcagcacgt aattctgacc cgtatgggcg atcagctatc tacggcaaaa    480
ggcacggtag tcaatttcgt tgttaaatac atcaagcgtt tggtgccgaa ataccatctg    540
ccagatgcca tttcatttcg tagcgcactg cataacggct accggatgca gtacgtcaaa    600
cccgaactgg tgccggaaga tttagctttt ctgcaataca ccggcggcac cactggtgtg    660
gcgaaaggcg cgatgctgac tcaccgcaat atgctggcga acctggaaca ggttaacgcg    720
acctatggtc cgctgttgca tccgggcaaa gagctggtgg tgacggcgct gccgctgtat    780 cacattttg ccctgaccat taactgcctg ctgtttatcg aactgggtgg gcagaacctg    840
cttatcacta acccgcgcga tattccaggg ttggtaaaag agttagcgaa atatccgttt    900
accgctatca cgggcgttaa caccttgttc aatgcgttgc tgaacaataa agagttccag    960
cagctggatt tctccagtct gcatctttcc gcaggcggtg gatgccagt gcagcaagtg   1020 gtggcagagc gttgggtgaa actgaccgga cagtatctgc tggaaggcta tggccttacc   1080
gagtgtgcgc cgctggtcag cgttaaccca tatgatattg attatcatag tggtagcatc   1140
ggtttgccgg tgccgtcgac ggaagccaaa ctggtggatg atgatgataa tgaagtacca   1200
ccaggtcaac cgggtgagct ttgtgtcaaa ggaccgcagg tgatgctggg ttactggcag   1260
cgtcccgatg ctaccgatga aatcatcaaa atggctggt tacacaccgg cgacatcgcg   1320
gtaatggatg aagaaggatt cctgcgcatt gtcgatcgta aaaaagacat gattctggtt   1380
tccggtttta acgtctatcc caacgagatt gaagatgtcg tcatgcagca tcctggcgta   1440
caggaagtcg cggctgttgg cgtaccttcc ggctccagtg gtgaagcggt gaaaatcttc   1500
gtagtgaaaa aagatccatc gcttaccgaa gagtcactgg tgactttttg ccgccgtcag   1560
ctcacgggat acaaagtacc gaagctggtg gagtttcgtg atgagttacc gaaatctaac   1620
gtcggaaaaa ttttgcgacg agaattacgt gacgaagcgc gcggcaaagt ggacaataaa   1680
gcctga                                                             1686

<210> SEQ ID NO 9
<211> LENGTH: 561
<212> TYPE: PRT
<213> ORGANISM: Artificial sequence
```

<220> FEATURE:
<223> OTHER INFORMATION: synthetic peptide

<400> SEQUENCE: 9

```
Leu Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
    370                 375                 380

Pro Ser Thr Glu Ala Lys Leu Val Asp Asp Asp Asn Glu Val Pro
385                 390                 395                 400
```

Pro Gly Gln Pro Gly Glu Leu Cys Val Lys Gly Pro Gln Val Met Leu
            405                 410                 415
Gly Tyr Trp Gln Arg Pro Asp Ala Thr Asp Glu Ile Ile Lys Asn Gly
        420                 425                 430
Trp Leu His Thr Gly Asp Ile Ala Val Met Asp Glu Glu Gly Phe Leu
    435                 440                 445
Arg Ile Val Asp Arg Lys Lys Asp Met Ile Leu Val Ser Gly Phe Asn
450                 455                 460
Val Tyr Pro Asn Glu Ile Glu Asp Val Val Met Gln His Pro Gly Val
465                 470                 475                 480
Gln Glu Val Ala Ala Val Gly Val Pro Ser Gly Ser Ser Gly Glu Ala
                485                 490                 495
Val Lys Ile Phe Val Val Lys Lys Asp Pro Ser Leu Thr Glu Glu Ser
            500                 505                 510
Leu Val Thr Phe Cys Arg Arg Gln Leu Thr Gly Tyr Lys Val Pro Lys
        515                 520                 525
Leu Val Glu Phe Arg Asp Glu Leu Pro Lys Ser Asn Val Gly Lys Ile
    530                 535                 540
Leu Arg Arg Glu Leu Arg Asp Glu Ala Arg Gly Lys Val Asp Asn Lys
545                 550                 555                 560
Ala

<210> SEQ ID NO 10
<211> LENGTH: 1722
<212> TYPE: DNA
<213> ORGANISM: Artificial sequence
<220> FEATURE:
<223> OTHER INFORMATION: synthetic nucleotide

<400> SEQUENCE: 10

```
tccaataaaa cgtcagggca aaagtaagaa acagacaaag caaaggccgc gtctcgagaa      60
tatcctcctt ataacttcgt ataatgtatg ctatacgaac ggtaagagcg cttttgaagc     120
tggggtgggc gaagaactcc agcatgagat ccccgcgctg gaggatcatc cagccggcgt     180
cccggaaaac gattccgaag cccaaccttt catagaaggc ggcggtggaa tcgaaatctc     240
gtgatggcag gttgggcgtc gcttggtcgg tcatttggaa ccccagagtc ccgctcagaa     300
gaactcgtca gaaggcgat agaaggcgat gcgctgcgaa tcgggagcgg cgataccgta     360
aagcacgagg aagcggtcag cccattcgcc gccaagctct tcagcaatat cacgggtagc     420
caacgctatg tcctgatagc ggtccgccac acccagccgg ccacagtcga tgaatccaga     480
aaagcggcca ttttccacca tgatattcgg caagcaggca tcgccatggg tcacgacgag     540
atcctcgccg tcgggcatgc gcgccttgag cctggcgaac agttcggctg cgcgagccc      600
ctgatgctct tcgtccagat catcctgatc gacaagaccg gcttccatcc gagtacgtgc     660
tcgctcgatg cgatgtttcg cttggtggtc gaatgggcag gtagccggat caagcgtatg     720
cagccgccgc attgcatcag ccatgatgga ctttctcg gcaggagcaa ggtgagatga     780
caggagatcc tgccccggca cttcgcccaa tagcagccag tcccttcccg cttcagtgac     840
aacgtcgagc acagctgcgc aaggaacgcc cgtcgtggcc agccacgata gccgcgctgc     900
ctcgtcctgc agttcattca gggcaccgga caggtcggtc ttgacaaaaa gaaccgggcg     960
cccctgcgct gacagccgga acacggcggc atcagagcag ccgattgtct gttgtgccca    1020
gtcatagccg aatagcctct ccacccaagc ggccggagaa cctgcgtgca atccatcttg    1080
```

| | |
|---|---:|
| ttcaatcatg cgaaacgatc ctcatcctgt ctcttgatca gatcttgatc ccctgcgcca | 1140 |
| tcagatcctt ggcggcaaga aagccatcca gtttactttg cagggcttcc caaccttacc | 1200 |
| agagggcgcc ccagctggca attccggttc gcttgctgtc cataaaaccg cccagtctag | 1260 |
| ctatcgccat gtaagcccac tgcaagctac ctgctttctc tttgcgcttg cgttttccct | 1320 |
| tgtccagata gcccagtagc tgacattcat ccggggtcag caccgtttct gcggactggc | 1380 |
| tttctacgtg ttccgcttcc tttagcagcc cttgcgccct gagtgcttgc ggcagcgtga | 1440 |
| ggggatcttt accgttcgta taatgtatgc tataccaagt tatgaagcta gcttatcaaa | 1500 |
| aagagtattg acataaagtc taacctatag ataattacag ccatcgagag ggacacggcg | 1560 |
| atttgctgtc accggatgtg ctttccggtc tgatgagtcc gtgaggacga aacagcctct | 1620 |
| acaaataatt ttgtttaaga attcaaaaga tcttttaaga aggagatata ccatgccaca | 1680 |
| ttcctacgat tacgatgcca tagtaatagg ttccggcccc gg | 1722 |

<210> SEQ ID NO 11
<211> LENGTH: 1401
<212> TYPE: DNA
<213> ORGANISM: Artificial sequence
<220> FEATURE:
<223> OTHER INFORMATION: synthetic nucleotide

<400> SEQUENCE: 11

| | |
|---|---:|
| atgccacatt cctacgatta cgatgccata gtaataggtt ccggccccgg cggcgaaggc | 60 |
| gctgcaatgg gcctggttaa gcaaggtgcg cgcgtcgcag ttatcgagcg ttatcaaaat | 120 |
| gttggcggcg gttgcaccca ctggggcacc atcccgtcga agctctccg tcacgccgtc | 180 |
| agccgcatta tagaattcaa tcaaaaccca ctttacagcg accattcccg actgctccgc | 240 |
| tcttcttttg ccgatatcct taaccatgcc gataacgtga ttaatcaaca aacgcgcatg | 300 |
| cgtcagggat tttacgaacg taatcactgt gaaatattgc agggaaacgc tcgctttgtt | 360 |
| gacgagcata cgttggcgct ggattgcccg acggcagcg ttgaaacact aaccgctgaa | 420 |
| aaatttgtta ttgcctgcgg ctctcgtcca tatcatccaa cagatgttga tttcacccat | 480 |
| ccacgcattt acgacagcga ctcaattctc agcatgcacc acgaaccgcg ccatgtactt | 540 |
| atctatggtg ctggagtgat cggctgtgaa tatgcgtcga tcttccgcgg tatggatgta | 600 |
| aaagtggatc tgatcaacac ccgcgatcgc ctgctggcat ttctcgatca agagatgtca | 660 |
| gattctctct cctatcactt ctggaacagt ggcgtagtga ttcgtcacaa cgaagagtac | 720 |
| gagaagatcg aaggctgtga cgatggtgtg atcatgcatc tgaagtcggg taaaaaactg | 780 |
| aaagctgact gcctgctcta tgccaacggt cgcaccggta taccgattc gctggcgtta | 840 |
| cagaacattg gctagaaaac tgacagccgc ggacagctga aggtcaacag catgtatcag | 900 |
| accgcacagc cacacgttta cgcggtgggc gacgtgattg gttatccgag cctggcgtcg | 960 |
| gcggcctatg accaggggcg cattgccgcg caggcgctgg taaaaggcga agccaccgca | 1020 |
| catctgattg aagatatccc taccggtatt tacaccatcc cggaaatcag ctctgtgggc | 1080 |
| aaaaccgaac agcagctgac cgcaatgaaa gtgccatatg aagtgggccg cgcccagttt | 1140 |
| aaacatctgg cacgcgcaca aatcgtcggc atgaacgtgg cacgctgaa aattttgttc | 1200 |
| catcgggaaa caaaagagat tctgggtatt cactgctttg gcgagcgcgc tgccgaaatt | 1260 |
| attcatatcg gtcaggcgat tatggaacag aaaggtggcg gcaacactat tgagtacttc | 1320 |
| gtcaacacca cctttaacta cccgacgatg gcggaagcct atcgggtagc tgcgttaaac | 1380 |
| ggtttaaacc gcctgtttta a | 1401 |

<210> SEQ ID NO 12
<211> LENGTH: 466
<212> TYPE: PRT
<213> ORGANISM: Artificial sequence
<220> FEATURE:
<223> OTHER INFORMATION: synthetic peptide

<400> SEQUENCE: 12

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
                20                  25                  30

Ala Val Ile Glu Arg Tyr Gln Asn Val Gly Gly Gly Cys Thr His Trp
            35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365
```

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465

<210> SEQ ID NO 13
<211> LENGTH: 1242
<212> TYPE: DNA
<213> ORGANISM: Artificial sequence
<220> FEATURE:
<223> OTHER INFORMATION: synthetic nucleotide

<400> SEQUENCE: 13
gtgtctaagc gtcgtgtagt tgtgaccgga ctgggcatgt tgtctcctgt cggcaatacc      60
gtagagtcta cctggaaagc tctgcttgcc ggtcagagtg gcatcagcct aatcgaccat     120
ttcgatacta gcgcctatgc aacgaaattt gctggcttag taaaggattt taactgtgag     180
gacattatct cgcgcaaaga acagcgcaag atggatgcct tcattcaata tggaattgtc     240
gctggcgttc aggccatgca ggattctggc cttgaaataa cggaagagaa cgcaacccgc     300
attggtgccg caattggctc cgggattggc ggcctcggac tgatcgaaga aaaccacaca     360
tctctgatga acgtggtcc acgtaagatc agcccattct tcgttccgtc aacgattgtg     420
aacatggtgg caggtcatct gactatcatg tatggcctgc gtggcccgag catctctatc     480
gcgactgcct gtacttccgg cgtgcacaac attggccatg ctgcgcgtat tatcgcgtat     540
ggcgatgctg acgtgatggt tgcaggtggc gcagagaaag ccagtacgcc gctgggcgtt     600
ggtggttttg cgcggcacg tgcattatct acccgcaatg ataacccgca agcggcgagc     660
cgcccgtggg ataaagagcg tgatggtttc gtactgggcg atggtgccgg tatgctggta     720
cttgaagagt acgaacacgc gaaaaaacgc ggtgcgaaaa tttacgctga actcgtcggc     780
tttggtatga gcagcgatgc ttatcatatg acgtcaccgc agaaaatgg cgcaggcgca     840 gctctggcga tggcaaatgc tctgcgtgat gcaggcattg aagcgagtca gattggctac     900
gttaacgcgc acggtacttc tacgccggct ggcgataaag ctgaagcgca ggcggtgaaa     960
accatcttcg gtgaagctgc aagccgtgtg ttggtaagct ccacgaaatc tatgaccggt    1020
cacctgttag gtgcggcggg tgcagtagaa tctatctact ccatcctggc gctgcgcgat    1080
caggctgttc cgccaaccat caacctggat aacccggatg aaggttgcga tctggatttc    1140
gtaccgcacg aagcgcgtca ggttagcgga atggaataca ctctgtgtaa ctccttcggc    1200
ttcggtggca ctaatggttc tttgatcttt aaaaagatct aa                      1242

<210> SEQ ID NO 14
<211> LENGTH: 413
<212> TYPE: PRT
<213> ORGANISM: Artificial sequence
<220> FEATURE:
<223> OTHER INFORMATION: synthetic peptide

<400> SEQUENCE: 14

```
Val Ser Lys Arg Arg Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
            35                  40                  45

Lys Phe Ala Gly Leu Val Lys Asp Phe Asn Cys Glu Asp Ile Ile Ser
            50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
            115                 120                 125

Lys Ile Ser Pro Phe Phe Val Pro Ser Thr Ile Val Asn Met Val Ala
            130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
            195                 200                 205

Leu Ser Thr Arg Asn Asp Asn Pro Gln Ala Ala Ser Arg Pro Trp Asp
            210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
            260                 265                 270

Pro Pro Glu Asn Gly Ala Gly Ala Ala Leu Ala Met Ala Asn Ala Leu
            275                 280                 285

Arg Asp Ala Gly Ile Glu Ala Ser Gln Ile Gly Tyr Val Asn Ala His
            290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
            355                 360                 365

Leu Asp Asn Pro Asp Glu Gly Cys Asp Leu Asp Phe Val Pro His Glu
            370                 375                 380

Ala Arg Gln Val Ser Gly Met Glu Tyr Thr Leu Cys Asn Ser Phe Gly
385                 390                 395                 400
```

Phe Gly Gly Thr Asn Gly Ser Leu Ile Phe Lys Lys Ile
            405                 410

<210> SEQ ID NO 15
<211> LENGTH: 954
<212> TYPE: DNA
<213> ORGANISM: Artificial sequence
<220> FEATURE:
<223> OTHER INFORMATION: synthetic nucleotide

<400> SEQUENCE: 15

```
atgtatacga agattattgg tactggcagc tatctgcccg aacaagtgcg gacaaacgcc      60
gatttggaaa aaatggtgga cacctctgac gagtggattg tcactcgtac cggtatccgc     120
gaacgccaca ttgccgcgcc aaacgaaacc gtttcaacca tgggctttga agcggcgaca     180
cgcgcaattg agatggcggg cattgagaaa gaccagattg cctgatcgt tgtggcaacg      240
acttctgcta cgcacgcttt cccgagcgca gcttgtcaga ttcaaagcat gttgggcatt     300
aaaggttgcc cggcatttga cgttgcagca gcctgcgcag gtttcaccta tgcattaagc     360
gtagccgatc aatacgtgaa atctggggcg gtgaagtatg ctctggtcgt cggttccgat     420
gtactggcgc gcacctgcga tccaaccgat cgtgggacta ttattatttt tggcgatggc     480
gcgggcgctg cggtgctggc tgcctctgaa gagccgggaa tcatttccac ccatctgcat     540
gccgacggta gttatggtga attgctgacg ctgccaaacg ccgaccgcgt gaatccagag     600
aattcaattc atctgacgat ggcgggcaac gaagtcttca aggttgcggt aacggaactg     660
gcgcacatcg ttgatgagac gctggcggcg aataatcttg accgttctca actggactgg     720
ctggttccgc atcaggctaa cctgcgtatt atcagtgcaa cggcgaaaaa actcggtatg     780
tctatggata atgtcgtggt gacgctggat cgccacggta ataccctgc ggcctctgtc      840
ccgtgcgcgc tggatgaagc tgtacgcgac gggcgcatta agccggggca gttggttctg     900
cttgaagcct ttggcggtgg attcacctgg ggctccgcgc tggttcgttt ctag            954
```

<210> SEQ ID NO 16
<211> LENGTH: 317
<212> TYPE: PRT
<213> ORGANISM: Artificial sequence
<220> FEATURE:
<223> OTHER INFORMATION: synthetic peptide

<400> SEQUENCE: 16

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

```
Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315
```

<210> SEQ ID NO 17
<211> LENGTH: 1722
<212> TYPE: DNA
<213> ORGANISM: Artificial sequence
<220> FEATURE:
<223> OTHER INFORMATION: synthetic nucleotide

<400> SEQUENCE: 17

```
ctcaggtgac cgatggagtg tggttaaggt agcggtaaaa gcgtgttacc gtctcgagaa      60
tatcctcctt ataacttcgt ataatgtatg ctatacgaac ggtaagagcg cttttgaagc     120
tggggtgggc gaagaactcc agcatgagat ccccgcgctg gaggatcatc agccggcgt      180
cccggaaaac gattccgaag cccaaccttt catagaaggc ggcggtggaa tcgaaatctc     240
gtgatggcag gttgggcgtc gcttggtcgg tcatttggaa ccccagagtc ccgctcagaa     300
gaactcgtca agaaggcgat agaaggcgat gcgctgcgaa tcgggagcgg cgataccgta     360
aagcacgagg aagcggtcag cccattcgcc gccaagctct tcagcaatat cacgggtagc     420
caacgctatg tcctgatagc ggtccgccac acccagccgg ccacagtcga tgaatccaga     480
aaagcggcca ttttccacca tgatattcgg caagcaggca tcgccatggg tcacgacgag     540
atcctcgccg tcgggcatgc gcgccttgag cctggcgaac agttcggctg cgcgagccc      600
ctgatgctct tcgtccagat catcctgatc gacaagaccg gcttccatcc gagtacgtgc     660
tcgctcgatg cgatgtttcg cttggtggtc gaatgggcag gtagccggat caagcgtatg     720
cagccgccgc attgcatcag ccatgatgga ctttctcg gcaggagcaa ggtgagatga      780
caggagatcc tgccccggca cttcgcccaa tagcagccag tcccttcccg cttcagtgac     840
aacgtcgagc acagctgcgc aaggaacgcc cgtcgtggcc agccacgata gccgcgctgc     900
ctcgtcctgc agttcattca gggcaccgga caggtcggtc ttgacaaaaa gaaccgggcg     960
```

| | |
|---|---|
| cccctgcgct gacagccgga acacggcggc atcagagcag ccgattgtct gttgtgccca | 1020 |
| gtcatagccg aatagcctct ccacccaagc ggccggagaa cctgcgtgca atccatcttg | 1080 |
| ttcaatcatg cgaaacgatc ctcatcctgt ctcttgatca gatcttgatc ccctgcgcca | 1140 |
| tcagatcctt ggcggcaaga aagccatcca gtttactttg cagggcttcc caaccttacc | 1200 |
| agagggcgcc ccagctggca attccggttc gcttgctgtc cataaaaccg cccagtctag | 1260 |
| ctatcgccat gtaagcccac tgcaagctac ctgctttctc tttgcgcttg cgttttccct | 1320 |
| tgtccagata gcccagtagc tgacattcat ccggggtcag caccgtttct gcggactggc | 1380 |
| tttctacgtg ttccgcttcc tttagcagcc cttgcgccct gagtgcttgc ggcagcgtga | 1440 |
| ggggatcttt accgttcgta atgtatgc ataccaagt tatgaagcta gcttatcaaa | 1500 |
| aagagtattg acataaagtc taacctatag ataattacag ccatcgagag ggacacggcg | 1560 |
| atttgctgtc accggatgtg ctttccggtc tgatgagtcc gtgaggacga aacagcctct | 1620 |
| acaaataatt ttgtttaaga attcaaaaga tcttttaaga aggagatata ccatgcatta | 1680 |
| tatgaagtgg atttatccac gccgcttacg caatcaaatg at | 1722 |

<210> SEQ ID NO 18
<211> LENGTH: 1827
<212> TYPE: DNA
<213> ORGANISM: Artificial sequence
<220> FEATURE:
<223> OTHER INFORMATION: synthetic nucleotide

<400> SEQUENCE: 18

| | |
|---|---|
| atgcattata tgaagtggat ttatccacgc cgcttacgca atcaaatgat cctgatggca | 60 |
| atcctgatgg tcattgtccc aacgcttact attggttata tcgtagaaac ggaaggacgt | 120 |
| tcagcagtct tatctgaaaa agagaaaaaa ctttctgccg tggtcaacct gcttaatcag | 180 |
| gcactaggcg atcgctatga tctctacatc gacttaccac gtgaggagcg tatccgcgca | 240 |
| ttaaatgcag aacttgcccc cattaccgaa aatatcactc acgccttccc tggcatcggt | 300 |
| gctggttatt acaacaaaat gctggatgcg ataatcacct acgcgccttc agcgctatat | 360 |
| cagaataatg tcggcgttac cattgccgca gatcaccctg gtcgcgaagt gatgcgtaca | 420 |
| aataccccctt tagtttattc aggcaggcag gtgcgcggcg atattttgaa ttcaatgctc | 480 |
| cccattgagc gtaatggtga atcctcggc tatatctggg ccaatgaatt aaccgaagat | 540 |
| attcgccgcc aggcctggaa atggatgtg aggattatca ttgtgctcac cgctggtttg | 600 |
| ctgataagcc tgctgttgat tgtccttttc tcccgtcgcc tgagcgccaa tattgatatc | 660 |
| atcaccgatg gcctctcgac tctggcacaa atattccca ctcgattacc acaattgccc | 720 |
| ggtgaaatgg gcaaatcag tcagagtgtt aataacctcg cccaggcact gcgtgaaacg | 780 |
| cggacactta acgatctgat tattgaaaac gctgccgatg gcgtcattgc cattgaccgc | 840 |
| cagggtgatg taaccaccat gaacccagca gcagaagtta tcactggcta tcaacgccat | 900 |
| gaactggtag gcagcctta ctccatgttg ttcgacaata ctcagttcta cagtccagta | 960 |
| ctggatacgc tggaacatgg caccgaacat gtggcgctgg agatcagttt tccaggtcgt | 1020 |
| gaccgcacca ttgaactcag tgtcactacc agtcgtattc ataacacgca cggtgaaatg | 1080 |
| ataggtgctt tggtgatttt ctctgattta actgcccgca agaaaccca gccgccgcatg | 1140 |
| gcgcaagcag aacgcctcgc cacactgggt gagctgatgg ctggcgtcgc gcatgaagta | 1200 |
| cgtaatccgt taacgctat tcgtggttat gtacagatct gcgccaaca aaccagtgac | 1260 |
| ccaatacatc aggaatatct gtccgtagta ctcaaagaaa tcgattcaat taacaaagtt | 1320 |

```
attcagcaat tgctcgaatt ttcacgtcca cgccacagtc aatggcaaca agtcagcctc   1380
aatgcattgg ttgaagaaac tctggtactg gtacaaaccg ccggcgtaca agcgcgggtc   1440
gacttcataa gcgaactgga taatgaatta agcccgatta acgccgatcg tgaactgctc   1500
aaacaggtac tactgaatat cctgatcaat gccgtccagg ctatcagcgc acgagggaaa   1560
attcgcattc aaacctggca atacagcgac tcacaacagg ccatttcgat agaggacaac   1620
ggctgtggca ttgatctctc gctgcaaaaa aagatcttcg atccctttt caccaccaaa   1680 gcctcaggaa ccgggcttgg tctggcgtta agtcaacgca tcattaatgc ccatcagggt   1740
gatattcgcg tcgccagttt gccgggctac ggcgcaacct tcacgcttat tttaccgatc   1800
aacccgcagg gaaatcagac tgtatga                                      1827

<210> SEQ ID NO 19
<211> LENGTH: 608
<212> TYPE: PRT
<213> ORGANISM: Artificial sequence
<220> FEATURE:
<223> OTHER INFORMATION: synthetic peptide

<400> SEQUENCE: 19
```

Met His Tyr Met Lys Trp Ile Tyr Pro Arg Arg Leu Arg Asn Gln Met
1               5                   10                  15

Ile Leu Met Ala Ile Leu Met Val Ile Val Pro Thr Leu Thr Ile Gly
            20                  25                  30

Tyr Ile Val Glu Thr Glu Gly Arg Ser Ala Val Leu Ser Glu Lys Glu
        35                  40                  45

Lys Lys Leu Ser Ala Val Val Asn Leu Leu Asn Gln Ala Leu Gly Asp
    50                  55                  60

Arg Tyr Asp Leu Tyr Ile Asp Leu Pro Arg Glu Glu Arg Ile Arg Ala
65                  70                  75                  80

Leu Asn Ala Glu Leu Ala Pro Ile Thr Glu Asn Ile Thr His Ala Phe
                85                  90                  95

Pro Gly Ile Gly Ala Gly Tyr Tyr Asn Lys Met Leu Asp Ala Ile Ile
            100                 105                 110

Thr Tyr Ala Pro Ser Ala Leu Tyr Gln Asn Asn Val Gly Val Thr Ile
        115                 120                 125

Ala Ala Asp His Pro Gly Arg Glu Val Met Arg Thr Asn Thr Pro Leu
    130                 135                 140

Val Tyr Ser Gly Arg Gln Val Arg Gly Asp Ile Leu Asn Ser Met Leu
145                 150                 155                 160

Pro Ile Glu Arg Asn Gly Glu Ile Leu Gly Tyr Ile Trp Ala Asn Glu
                165                 170                 175

Leu Thr Glu Asp Ile Arg Arg Gln Ala Trp Lys Met Asp Val Arg Ile
            180                 185                 190

Ile Ile Val Leu Thr Ala Gly Leu Leu Ile Ser Leu Leu Leu Ile Val
        195                 200                 205

Leu Phe Ser Arg Arg Leu Ser Ala Asn Ile Asp Ile Thr Asp Gly
    210                 215                 220

Leu Ser Thr Leu Ala Gln Asn Ile Pro Thr Arg Leu Pro Gln Leu Pro
225                 230                 235                 240

Gly Glu Met Gly Gln Ile Ser Gln Ser Val Asn Asn Leu Ala Gln Ala
                245                 250                 255

Leu Arg Glu Thr Arg Thr Leu Asn Asp Leu Ile Ile Glu Asn Ala Ala
            260                 265                 270

Asp Gly Val Ile Ala Ile Asp Arg Gln Gly Asp Val Thr Thr Met Asn
        275                 280                 285

Pro Ala Ala Glu Val Ile Thr Gly Tyr Gln Arg His Glu Leu Val Gly
    290                 295                 300

Gln Pro Tyr Ser Met Leu Phe Asp Asn Thr Gln Phe Tyr Ser Pro Val
305                 310                 315                 320

Leu Asp Thr Leu Glu His Gly Thr Glu His Val Ala Leu Glu Ile Ser
                325                 330                 335

Phe Pro Gly Arg Asp Arg Thr Ile Glu Leu Ser Val Thr Thr Ser Arg
            340                 345                 350

Ile His Asn Thr His Gly Glu Met Ile Gly Ala Leu Val Ile Phe Ser
        355                 360                 365

Asp Leu Thr Ala Arg Lys Glu Thr Gln Arg Arg Met Ala Gln Ala Glu
    370                 375                 380

Arg Leu Ala Thr Leu Gly Glu Leu Met Ala Gly Val Ala His Glu Val
385                 390                 395                 400

Arg Asn Pro Leu Thr Ala Ile Arg Gly Tyr Val Gln Ile Leu Arg Gln
                405                 410                 415

Gln Thr Ser Asp Pro Ile His Gln Glu Tyr Leu Ser Val Val Leu Lys
            420                 425                 430

Glu Ile Asp Ser Ile Asn Lys Val Ile Gln Gln Leu Leu Glu Phe Ser
        435                 440                 445

Arg Pro Arg His Ser Gln Trp Gln Gln Val Ser Leu Asn Ala Leu Val
    450                 455                 460

Glu Glu Thr Leu Val Leu Val Gln Thr Ala Gly Val Gln Ala Arg Val
465                 470                 475                 480

Asp Phe Ile Ser Glu Leu Asp Asn Glu Leu Ser Pro Ile Asn Ala Asp
                485                 490                 495

Arg Glu Leu Leu Lys Gln Val Leu Leu Asn Ile Leu Ile Asn Ala Val
            500                 505                 510

Gln Ala Ile Ser Ala Arg Gly Lys Ile Arg Ile Gln Thr Trp Gln Tyr
        515                 520                 525

Ser Asp Ser Gln Gln Ala Ile Ser Ile Glu Asp Asn Gly Cys Gly Ile
    530                 535                 540

Asp Leu Ser Leu Gln Lys Lys Ile Phe Asp Pro Phe Phe Thr Thr Lys
545                 550                 555                 560

Ala Ser Gly Thr Gly Leu Gly Leu Ala Leu Ser Gln Arg Ile Ile Asn
                565                 570                 575

Ala His Gln Gly Asp Ile Arg Val Ala Ser Leu Pro Gly Tyr Gly Ala
            580                 585                 590

Thr Phe Thr Leu Ile Leu Pro Ile Asn Pro Gln Gly Asn Gln Thr Val
        595                 600                 605

<210> SEQ ID NO 20
<211> LENGTH: 1386
<212> TYPE: DNA
<213> ORGANISM: Artificial sequence
<220> FEATURE:
<223> OTHER INFORMATION: synthetic nucleotide

<400> SEQUENCE: 20
atgactgcta ttaatcgcat ccttattgtg gatgatgaag ataatgttcg ccgtatgctg      60
agcaccgctt ttgcactaca aggattcgaa acacattgtg cgaacaacgg acgcacagca     120
ttacacctgt ttgccgatat tcaccctgat gtggtgttga tggatatccg catgccagag     180

```
atggacggca tcaaggcact aaaggagatg cgcagccatg agacccggac acccgttatt    240
ctgatgacgg cctatgcgga agtggaaacc gccgtcgaag cgctacgctg cggagccttc    300
gactatgtta ttaaaccgtt tgatctcgat gagttgaatt taatcgttca gcgcgcttta    360
caactccagt caatgaaaaa agagatccgt catctgcacc aggcactgag caccagctgg    420
caatgggggc acattctcac caacagcccg gcgatgatgg acatctgcaa agacaccgcc    480
aaaattgccc tttctcaggc cagcgtcttg attagcggtg aaagcggcac cgggaaagag    540
ttgattgcca gagcgattca ctacaattcg cggcgggcaa aggggccgtt cattaaagtc    600
aactgcgcgg cgctgccgga atcgttgctc gaaagtgaac tgtttggtca tgaaaaaggt    660
gcatttactg gtgcacaaac cttgcgtcag ggattatttg aacgagccaa cgaaggtact    720
ctgctcctcg acgaaattgg cgaaatgccg ctggtactac aagccaaatt actacgcatt    780
ctacaggaac gggaatttga acggattggc ggccatcaga ccataaaagt tgatatccgc    840
atcattgctg ccaccaaccg cgacttgcag gcaatggtaa agaaggcac cttccgtgaa    900 gatctctttt atcgccttaa cgttattcat ttaatactgc cgcctctgcg cgatcgccgg    960
gaagatattt ccctgttagc taatcacttt ttgcaaaaat tcagtagtga aatcagcgc   1020 gatattatcg acatcgatcc gatggcaatg tcactgctta ccgcctggtc atggccggga   1080
aatattcgag agctttccaa cgttattgaa cgcgccgtcg tgatgaattc aggcccgatc   1140 atttttctg aggatcttcc gccacagatt cgtcagccag tctgtaatgc tggcgaggta   1200
aaaacagccc ctgtcggtga gcgtaattta aagaggaaa ttaaacgcgt cgaaaaacgc   1260
atcattatgg aagtgctgga acaacaagaa ggaaaccgaa cccgcactgc tttaatgctg   1320
ggcatcagtc gccgtgcatt gatgtataaa ctccaggaat acggtatcga tccggcggat   1380
gtataa                                                               1386
```

<210> SEQ ID NO 21
<211> LENGTH: 461
<212> TYPE: PRT
<213> ORGANISM: Artificial sequence
<220> FEATURE:
<223> OTHER INFORMATION: synthetic peptide

<400> SEQUENCE: 21

```
Met Thr Ala Ile Asn Arg Ile Leu Ile Val Asp Asp Glu Asp Asn Val
1               5                   10                  15

Arg Arg Met Leu Ser Thr Ala Phe Ala Leu Gln Gly Phe Glu Thr His
            20                  25                  30

Cys Ala Asn Asn Gly Arg Thr Ala Leu His Leu Phe Ala Asp Ile His
        35                  40                  45

Pro Asp Val Val Leu Met Asp Ile Arg Met Pro Glu Met Asp Gly Ile
    50                  55                  60

Lys Ala Leu Lys Glu Met Arg Ser His Glu Thr Arg Thr Pro Val Ile
65                  70                  75                  80

Leu Met Thr Ala Tyr Ala Glu Val Glu Thr Ala Val Glu Ala Leu Arg
                85                  90                  95

Cys Gly Ala Phe Asp Tyr Val Ile Lys Pro Phe Asp Leu Asp Glu Leu
            100                 105                 110

Asn Leu Ile Val Gln Arg Ala Leu Gln Leu Gln Ser Met Lys Lys Glu
        115                 120                 125

Ile Arg His Leu His Gln Ala Leu Ser Thr Ser Trp Gln Trp Gly His
    130                 135                 140
```

```
Ile Leu Thr Asn Ser Pro Ala Met Met Asp Ile Cys Lys Asp Thr Ala
145                 150                 155                 160

Lys Ile Ala Leu Ser Gln Ala Ser Val Leu Ile Ser Gly Glu Ser Gly
            165                 170                 175

Thr Gly Lys Glu Leu Ile Ala Arg Ala Ile His Tyr Asn Ser Arg Arg
        180                 185                 190

Ala Lys Gly Pro Phe Ile Lys Val Asn Cys Ala Ala Leu Pro Glu Ser
    195                 200                 205

Leu Leu Glu Ser Glu Leu Phe Gly His Glu Lys Gly Ala Phe Thr Gly
210                 215                 220

Ala Gln Thr Leu Arg Gln Gly Leu Phe Glu Arg Ala Asn Glu Gly Thr
225                 230                 235                 240

Leu Leu Leu Asp Glu Ile Gly Glu Met Pro Leu Val Leu Gln Ala Lys
                245                 250                 255

Leu Leu Arg Ile Leu Gln Glu Arg Glu Phe Glu Arg Ile Gly Gly His
            260                 265                 270

Gln Thr Ile Lys Val Asp Ile Arg Ile Ala Ala Thr Asn Arg Asp
        275                 280                 285

Leu Gln Ala Met Val Lys Glu Gly Thr Phe Arg Glu Asp Leu Phe Tyr
    290                 295                 300

Arg Leu Asn Val Ile His Leu Ile Leu Pro Pro Leu Arg Asp Arg Arg
305                 310                 315                 320

Glu Asp Ile Ser Leu Leu Ala Asn His Phe Leu Gln Lys Phe Ser Ser
                325                 330                 335

Glu Asn Gln Arg Asp Ile Ile Asp Ile Asp Pro Met Ala Met Ser Leu
            340                 345                 350

Leu Thr Ala Trp Ser Trp Pro Gly Asn Ile Arg Glu Leu Ser Asn Val
        355                 360                 365

Ile Glu Arg Ala Val Val Met Asn Ser Gly Pro Ile Ile Phe Ser Glu
370                 375                 380

Asp Leu Pro Pro Gln Ile Arg Gln Pro Val Cys Asn Ala Gly Glu Val
385                 390                 395                 400

Lys Thr Ala Pro Val Gly Glu Arg Asn Leu Lys Glu Glu Ile Lys Arg
                405                 410                 415

Val Glu Lys Arg Ile Ile Met Glu Val Leu Glu Gln Gln Glu Gly Asn
            420                 425                 430

Arg Thr Arg Thr Ala Leu Met Leu Gly Ile Ser Arg Arg Ala Leu Met
        435                 440                 445

Tyr Lys Leu Gln Glu Tyr Gly Ile Asp Pro Ala Asp Val
    450                 455                 460

<210> SEQ ID NO 22
<211> LENGTH: 2046
<212> TYPE: DNA
<213> ORGANISM: Artificial sequence
<220> FEATURE:
<223> OTHER INFORMATION: synthetic nucleotide

<400> SEQUENCE: 22
atggcagatc tccatcacca tcatcaccat cacagcgcca ccaccggcgc acgcagtgca      60
tcggtcggat gggcggaaag cctgatcggg ttgcatttgg ggaaagttgc cttgattacc     120
ggtggcagcg ccggtattgg tgggcagatc gggcgcctcc tggctttgag tggcgcgcgc     180
gtgatgctgg cagcccgtga tcggcataag ctcgaacaga tgcaggcgat gatccaatct     240
```

```
gagctggctg aggtggggta taccgatgtc gaagatcgcg tccacattgc accgggctgc    300
gatgtgagta gcgaagcgca gcttgcggat cttgttgaac gtaccctgtc agcttttggc    360
accgtcgatt atctgatcaa caacgccggg atcgccggtg tcgaagagat ggttatcgat    420
atgccagttg agggatggcg ccatacccctc ttcgccaatc tgatcagcaa ctactcgttg    480
atgcgcaaac tggcgccgtt gatgaaaaaa cagggtagcg gttacatcct taacgtctca    540
tcatactttg gcggtgaaaa agatgcggcc attccctacc ccaaccgtgc cgattacgcc    600
gtctcgaagg ctggtcagcg ggcaatggcc gaagtctttg cgcgcttcct tggcccggag    660
atacagatca atgccattgc gccgggtccg gtcgaaggtg atcgcttgcg cggtaccggt    720
gaacgtcccg gcctctttgc ccgtcgggcg cggctgattt tggagaacaa gcggctgaat    780
gagcttcacg ctgctcttat cgcggctgcg cgcaccgatg agcgatctat gcacgaactg    840
gttgaactgc tcttacccaa tgatgtgccc gcactagagc agaatcccgc agcacctacc    900
gcgttgcgtg aactggcacg acgttttcgc agcgaaggcg atccggcggc atcatcaagc    960
agtgcgctgc tgaaccgttc aattgccgct aaattgctgg ctcgtttgca taatggtggc   1020
tatgtgttgc ctgccgacat ctttgcaaac ctgccaaacc cgcccgatcc cttcttcacc   1080
cgagcccaga ttgatcgcga ggctcgcaag gttcgtgacg gcatcatggg gatgctctac   1140
ctgcaacgga tgccgactga gttttgatgtc gcaatggcca ccgtctatta ccttgccgac   1200
cgcgtggtca gtggtgagac attccacccca tcaggtggtt tgcgttacga acgcacccct   1260
accggtggcg aactcttcgg cttgccctca ccggaacggc tggcggagct ggtcggaagc   1320
acggtctatc tgataggtga acatctgact gaacaccttta acctgcttgc ccgtgcgtac   1380
ctcgaacgtt acggggcacg tcaggtagtg atgattgttg agacagaaac cggggcagag   1440
acaatgcgtc gcttgctcca cgatcacgtc gaggctggtc ggctgatgac tattgtggcc   1500
ggtgatcaga tcgaagccgc tatcgaccag gctatcactc gctacggtcg cccagggccg   1560
gtcgtctgta cccccttccg gccactgccg acggtaccac tggtcgggcg taaagacagt   1620
gactggagca cagtgttgag tgaggctgaa tttgccgagt tgtgcgaaca ccagctcacc   1680 caccattttcc gggtagcgcg ctggattgcc ctgagtgatg gtgcccgtct cgcgctggtc   1740
actcccgaaa ctacggctac ctcaactacc gagcaatttg ctctggctaa cttcatcaaa   1800 acgaccctttc acgcttttac ggctacgatt ggtgtcgaga gcgaaagaac tgctcagcgc   1860
attctgatca atcaagtcga tctgacccgg cgtgcgcgtg ccgaagagcc gcgtgatccg   1920
cacgagcgtc aacaagaact ggaacgtttt atcgaggcag tcttgctggt cactgcacca   1980 ctccccgcctg aagccgatac ccgttacgcc gggcggattc atcgcggacg ggcgattacc   2040
gtgtaa                                                              2046
```

<210> SEQ ID NO 23
<211> LENGTH: 681
<212> TYPE: PRT
<213> ORGANISM: Artificial sequence
<220> FEATURE:
<223> OTHER INFORMATION: synthetic peptide

<400> SEQUENCE: 23

Met Ala Asp Leu His His His His His His Ser Ala Thr Thr Gly
1               5                   10                  15

Ala Arg Ser Ala Ser Val Gly Trp Ala Glu Ser Leu Ile Gly Leu His
            20                  25                  30

Leu Gly Lys Val Ala Leu Ile Thr Gly Gly Ser Ala Gly Ile Gly Gly

```
                35                    40                    45
Gln Ile Gly Arg Leu Leu Ala Leu Ser Gly Ala Arg Val Met Leu Ala
 50                    55                    60
Ala Arg Asp Arg His Lys Leu Glu Gln Met Gln Ala Met Ile Gln Ser
 65                    70                    75                    80
Glu Leu Ala Glu Val Gly Tyr Thr Asp Val Glu Asp Arg Val His Ile
                        85                    90                    95
Ala Pro Gly Cys Asp Val Ser Ser Glu Ala Gln Leu Ala Asp Leu Val
                100                   105                   110
Glu Arg Thr Leu Ser Ala Phe Gly Thr Val Asp Tyr Leu Ile Asn Asn
            115                   120                   125
Ala Gly Ile Ala Gly Val Glu Glu Met Val Ile Asp Met Pro Val Glu
        130                   135                   140
Gly Trp Arg His Thr Leu Phe Ala Asn Leu Ile Ser Asn Tyr Ser Leu
145                   150                   155                   160
Met Arg Lys Leu Ala Pro Leu Met Lys Lys Gln Gly Ser Gly Tyr Ile
                    165                   170                   175
Leu Asn Val Ser Ser Tyr Phe Gly Gly Glu Lys Asp Ala Ala Ile Pro
                180                   185                   190
Tyr Pro Asn Arg Ala Asp Tyr Ala Val Ser Lys Ala Gly Gln Arg Ala
            195                   200                   205
Met Ala Glu Val Phe Ala Arg Phe Leu Gly Pro Glu Ile Gln Ile Asn
210                   215                   220
Ala Ile Ala Pro Gly Pro Val Glu Gly Asp Arg Leu Arg Gly Thr Gly
225                   230                   235                   240
Glu Arg Pro Gly Leu Phe Ala Arg Arg Ala Arg Leu Ile Leu Glu Asn
                    245                   250                   255
Lys Arg Leu Asn Glu Leu His Ala Ala Leu Ile Ala Ala Ala Arg Thr
                260                   265                   270
Asp Glu Arg Ser Met His Glu Leu Val Glu Leu Leu Pro Asn Asp
            275                   280                   285
Val Ala Ala Leu Glu Gln Asn Pro Ala Ala Pro Thr Ala Leu Arg Glu
        290                   295                   300
Leu Ala Arg Arg Phe Arg Ser Glu Gly Asp Pro Ala Ala Ser Ser Ser
305                   310                   315                   320
Ser Ala Leu Leu Asn Arg Ser Ile Ala Ala Lys Leu Leu Ala Arg Leu
                    325                   330                   335
His Asn Gly Gly Tyr Val Leu Pro Ala Asp Ile Phe Ala Asn Leu Pro
                340                   345                   350
Asn Pro Pro Asp Pro Phe Phe Thr Arg Ala Gln Ile Asp Arg Glu Ala
            355                   360                   365
Arg Lys Val Arg Asp Gly Ile Met Gly Met Leu Tyr Leu Gln Arg Met
        370                   375                   380
Pro Thr Glu Phe Asp Val Ala Met Ala Thr Val Tyr Tyr Leu Ala Asp
385                   390                   395                   400
Arg Val Val Ser Gly Glu Thr Phe His Pro Ser Gly Leu Arg Tyr
                    405                   410                   415
Glu Arg Thr Pro Thr Gly Gly Glu Leu Phe Gly Leu Pro Ser Pro Glu
                420                   425                   430
Arg Leu Ala Glu Leu Val Gly Ser Thr Val Tyr Leu Ile Gly Glu His
            435                   440                   445
Leu Thr Glu His Leu Asn Leu Leu Ala Arg Ala Tyr Leu Glu Arg Tyr
        450                   455                   460
```

Gly Ala Arg Gln Val Val Met Ile Val Glu Thr Glu Thr Gly Ala Glu
465                 470                 475                 480

Thr Met Arg Arg Leu Leu His Asp His Val Glu Ala Gly Arg Leu Met
                485                 490                 495

Thr Ile Val Ala Gly Asp Gln Ile Glu Ala Ala Ile Asp Gln Ala Ile
            500                 505                 510

Thr Arg Tyr Gly Arg Pro Gly Pro Val Val Cys Thr Pro Phe Arg Pro
        515                 520                 525

Leu Pro Thr Val Pro Leu Val Gly Arg Lys Asp Ser Asp Trp Ser Thr
    530                 535                 540

Val Leu Ser Glu Ala Glu Phe Ala Glu Leu Cys Glu His Gln Leu Thr
545                 550                 555                 560

His His Phe Arg Val Ala Arg Trp Ile Ala Leu Ser Asp Gly Ala Arg
                565                 570                 575

Leu Ala Leu Val Thr Pro Glu Thr Thr Ala Thr Ser Thr Thr Glu Gln
            580                 585                 590

Phe Ala Leu Ala Asn Phe Ile Lys Thr Thr Leu His Ala Phe Thr Ala
        595                 600                 605

Thr Ile Gly Val Glu Ser Glu Arg Thr Ala Gln Arg Ile Leu Ile Asn
    610                 615                 620

Gln Val Asp Leu Thr Arg Arg Ala Arg Ala Glu Glu Pro Arg Asp Pro
625                 630                 635                 640

His Glu Arg Gln Gln Glu Leu Glu Arg Phe Ile Glu Ala Val Leu Leu
                645                 650                 655

Val Thr Ala Pro Leu Pro Pro Glu Ala Asp Thr Arg Tyr Ala Gly Arg
            660                 665                 670

Ile His Arg Gly Arg Ala Ile Thr Val
    675                 680

<210> SEQ ID NO 24
<211> LENGTH: 4293
<212> TYPE: DNA
<213> ORGANISM: Artificial sequence
<220> FEATURE:
<223> OTHER INFORMATION: synthetic nucleotide

<400> SEQUENCE: 24
aatgtgcctg tcaaatggac gaagcaggga ttctgcaaac cctatgctac tccgtcaagc      60
cgtcaattgt ctgattcgtt accaattatg acaacttgac ggctacatca ttcactttt     120 cttcacaacc ggcacggaac tcgctcgggc tggccccgt gcattttta atacccgcg      180 agaaatagag ttgatcgtca aaccaacat tgcgaccgac ggtggcgata ggcatccggg     240
tggtgctcaa aagcagcttc gcctggctga tacgttggtc ctcgcgccag cttaagacgc     300
taatccctaa ctgctggcgg aaaagatgtg acagacgcga cggcgacaag caaacatgct     360
gtgcgacgct ggcgatatca aaattgctgt ctgccaggtg atcgctgatg tactgacaag     420
cctcgcgtac ccgattatcc atcggtggat ggagcgactc gttaatcgct ccatgcgcc     480 gcagtaacaa ttgctcaagc agatttatcg ccagcagctc cgaatagcgc ccttcccctt     540
gcccggcgtt aatgatttgc ccaaacaggt cgctgaaatg cggctggtgc gcttcatccg     600
ggcgaaagaa ccccgtattg caaatattg acggccagtt aagccattca tgccagtagg     660
cgcgcggacg aaagtaaacc cactggtgat accattcgcg agcctccgga tgacgaccgt     720
agtgatgaat ctctcctggc gggaacagca aatatcacc cggtcggcaa acaaattctc     780

```
gtccctgatt tttcaccacc ccctgaccgc gaatggtgag attgagaata taacctttca    840
ttcccagcgg tcggtcgata aaaaaatcga gataaccgtt ggcctcaatc ggcgttaaac    900
ccgccaccag atgggcatta acgagtatc  ccggcagcag gggatcattt tgcgcttcag    960
ccatactttt catactcccg ccattcagag aagaaaccaa ttgtccatat tgcatcagac   1020
attgccgtca ctgcgtcttt tactggctct tctcgctaac caaaccggta accccgctta   1080
ttaaaagcat tctgtaacaa agcgggacca aagccatgaa aaaacgcgt  aacaaaagtg   1140
tctataatca cggcagaaaa gtccacattg attatttgca cggcgtcaca ctttgctatg   1200
ccatagcatt tttatccata agattagcgg atcctacctg acgcttttta tcgcaactct   1260
ctactgtttc tccatacccg ttttttgggc taacaggagg aattaaccat gggtacctct   1320
catcatcatc atcatcacag cagcggcctg gtgccgcgcg gcagcctcga gggtagatct   1380
ggtactagtg gtgaattcgg tgagctcggt ctgcagctgg tgccgcgcgg cagccaccac   1440
caccaccacc actaatacag attaaatcag aacgcagaag cggtctgata aaacagaatt   1500
tgcctggcgg cagtagcgcg gtggtccac  ctgaccccat gccgaactca gaagtgaaac   1560
gccgtagcgc cgatggtagt gtggggtctc cccatgcgag agtagggaac tgccaggcat   1620
caaataaaac gaaaggctca gtcgaaagac tgggcctttc gtcgacctaa ttcccatgtc   1680
agccgttaag tgttcctgtg tcactgaaaa ttgctttgag aggctctaag ggcttctcag   1740
tgcgttacat ccctggcttg ttgtccacaa ccgttaaacc ttaaaagctt taaaagcctt   1800
atatattctt ttttttctta taaaacttaa aaccttagag gctatttaag ttgctgattt   1860
atattaattt tattgttcaa acatgagagc ttagtacgtg aaacatgaga gcttagtacg   1920
ttagccatga gagcttagta cgttagccat gagggtttag ttcgttaaac atgagagctt   1980
agtacgttaa acatgagagc ttagtacgtg aaacatgaga gcttagtacg tactatcaac   2040
aggttgaact gcggatcttg atgagtggat agtacgttgc taaaacatga gataaaaatt   2100
gactctcatg ttattggcgt taagatatac agaatgatga ggttttttta tgagactcaa   2160
ggtcatgatg gacgtgaaca aaaaaacgaa aattcgccac cgaaacgagc taaatcacac   2220
cctggctcaa cttcctttgc ccgcaaagcg agtgatgtat atggcgcttg ctcccattga   2280
tagcaaggaa cctcttgaac gagggcgagt tttcaaaatt agggctgaag accttgcagc   2340
gctcgccaaa atcacccccat cgcttgctta tcgacaatta aaagagggtg gtaagttact   2400
tggtgccagc aaaatttcgc taagagggga tgatatcatt gcttcagcta aagagcttaa   2460
cctgctcttt actgctaaag actcccctga agagttagat cttaacatta ttgagtggat   2520
agcttattca aatgatgaag gatacttgtc tttaaaattc accagaacca tagaaccata   2580
tatctctagc cttattggga aaaaaataa  attcacaacg caattgttaa cggcaagctt   2640
acgcttaagt agccagtatt catcttctct ttatcaactt atcaggaagc attactctaa   2700
ttttaagaag aaaaattatt ttattatttc cgttgatgag ttaaaggaag agttaatagc   2760
ttatactttt gataaagatg gaagtattga gtacaaatac cctgactttc ctattttaa    2820
aagggatgta ttaaataaag ccattgctga aattaaaaag aaaacagaaa tatcgtttgt   2880
tggctttact gttcatgaaa agaaggaag  aaaaattagt aagctgaagt tcgaatttgt   2940
cgttgatgaa gatgaatttt ctggcgataa agatgatgaa gctttttta  tgaatttatc   3000
tgaagctaat gcagctttttc tcaaggtatt tgatgaaacc gtacctccca aaaaagctaa   3060
ggggtgatat atggctaaaa tttacgattt ccctcaagga gccgaacgcc gcaggatgca   3120
ccgcaaaatc cagtggaaca acgctgtaaa attatctaaa aatggctgga gtaagccaga   3180
```

```
ggttaaacgc tggtctttt tagcattcat ctcaactggc tggcggccgc ggaacccta      3240 tttgtttatt tttctaaata cattcaaata tgtatccgct catgagacaa taaccctgat   3300
aaatgcttca ataatattga aaaggaaga gtatgagtat tcaacatttc cgtgtcgccc    3360
ttattccctt ttttgcggca ttttgccttc ctgttttgc tcacccagaa acgctggtga    3420
aagtaaaaga tgctgaagat cagttgggtg cacgagtggg ttacatcgaa ctggatctca   3480
acagcggtaa gatccttgag agttttcgcc ccgaagaacg tttccaatg atgagcactt    3540 ttaaagttct gctatgtgat acactattat cccgtattga cgccgggcaa gagcaactcg   3600
gtcgccgcat acactattct cagaatgact tggttgagta ctcaccagtc acagaaaagc   3660
atcttacgga tggcatgaca gtaagagaat tatgcagtgc tgccataacc atgagtgata   3720
acactgcggc caacttactt ctgacaacga tcggaggacc gaaggagcta accgcttttt   3780
tgcacaacat gggggatcat gtaactcgcc ttgatcgttg gaaccggag ctgaatgaag    3840 ccataccaaa cgacgagcgt gacaccacga tgcctgtagc aatgccaaca acgttgcgca   3900
aactattaac tggcgaacta cttactctag cttcccggca acaattaata gactgaatgg   3960
aggcggataa agttgcagga ccacttctgc gctcggccct tccggctggc tggttttattg  4020 ctgataaatc tggagccggt gagcgtgggt ctcgcggtat cattgcagca ctggggccag   4080
atggtaagcg ctcccgtatc gtagttatct acaccacggg gagtcaggca actatggatg   4140
aacgaaatag acagatcgct gagataggtg cctcactgat taagcattgg taactgtcag   4200
accaagttta ctcatatata ctttagattg atttaaaact tcattttaa tttaaaagga   4260 tctaggtgaa gatccttttt gataatcgca tgc                                4293
```

<210> SEQ ID NO 25
<211> LENGTH: 3259
<212> TYPE: DNA
<213> ORGANISM: Artificial sequence
<220> FEATURE:
<223> OTHER INFORMATION: synthetic nucleotide

<400> SEQUENCE: 25

```
caggaggaat taacatgtca gtcgagacta ggaagatcac caaggttctt gtcgctaacc     60
gtggtgagat tgcaatccgc gtgttccgtg cagctcgaga tgaaggcatc ggatctgtcg    120
ccgtctacgc agagccagat gcagatgcac cattcgtgtc atatgcagac gaggcttttg    180
ccctcggtgg ccaaacatcc gctgagtcct accttgtcat tgacaagatc atcgatgcgg    240
cccgcaagtc cggcgccgac gccatccacc cggctacgg cttcctcgca gaaaacgctg    300
acttcgcaga agcagtcatc aacgaaggcc tgatctggat tggaccttca cctgagtcca    360
tccgctccct cggcgacaag gtcaccgctc gccacatcgc agataccgcc aaggctccaa    420
tggctcctgg caccaaggaa ccagtaaaag acgcagcaga agttgtggct ttcgctgaag    480
agttcggtct cccaatcgcc atcaaggcag ctttcggtgg cggcggacgt ggcatgaagg    540
ttgcctacaa gatggaagaa gtcgctgacc tcttcgagtc cgcaacccgt gaagcaaccg    600
cagcgttcgg ccgcggcgag tgcttcgtgg agcgctacct ggacaaggca cgccacgttg    660
aggctcaggt catcgccgat aagcacggca cgttgttgt cgccggaacc cgtgactgct    720
ccctccagcg ccgtttccag aagctcgtcg aagaagcacc agcaccattc ctcaccgatg    780
accagcgcga gcgtctccac tcctccgcga aggctatctg taaggaagct ggctactacg    840
gtgcaggcac cgttgagtac ctcgttggct ccgacggcct gatctccttc ctcgaggtca    900
```

```
acacccgcct ccaggtggaa cacccagtca ccgaagagac caccggcatc gacctggtcc   960
gcgaaatgtt ccgcatcgca gaaggccacg agctctccat caaggaagat ccagctccac  1020
gcggccacgc attcgagttc cgcatcaacg gcgaagacgc tggctccaac ttcatgcctg  1080
caccaggcaa gatcaccagc taccgcgagc cacagggccc aggcgtccgc atggactccg  1140
gtgtcgttga aggttccgaa atctccggac agttcgactc catgctggca aagctgatcg  1200
tttggggcga cacccgcgag caggctctcc agcgctcccg ccgtgcactt gcagagtacg  1260
ttgtcgaggg catgccaacc gttatcccat tccaccagca catcgtggaa acccagcat   1320
tcgtgggcaa cgacgaaggc ttcgagatct acaccaagtg gatcgaagag gtttgggata  1380
acccaatcgc accttacgtt gacgcttccg agctcgacga agatgaggac aagacccag   1440
cacagaaggt tgttgtggag atcaacggcc gtcgcgttga ggttgcactc ccaggcgatc  1500
tggcactcgg tggcaccgct ggtcctaaga agaaggccaa gaagcgtcgc gcaggtggtg  1560
caaaggctgg cgtatccggc gatgcagtgg cagctccaat gcagggcact gtcatcaagg  1620
tcaacgtcga agaaggcgct gaagtcaacg aaggcgcacg cgttgttgtc ctcgaggcta  1680
tgaagatgga aaaccctgtg aaggctcata gtccggaac cgtaaccggc cttactgtcg   1740
cagctggcga gggtgtcaac aagggcgttg ttctcctcga gatcaagtaa caggaggaat  1800
taacatggtg tggggcatgg aacacacttc agcattgacg ctcatagact cggttttgga  1860
ccctgacagc ttcatttctt ggaatgaaac tccccaatat gacaacctca atcaaggcta  1920
tgcagagacc ttggagcggg ctcgaagcaa ggccaaatgc gatgaatcgg taattactgg  1980
agaaggcacc gtggagggca ttccggtagc cgttattttg tccgatttt ccttcctcgg   2040
cggttctttg ggcacggtcg cgtcggtgcg catcatgaag gcgattcacc gcgccacaga  2100
gctgaaactc ccactgctgg tctcccctgc ttccggtggt gcgcgcatgc aggaagacaa  2160
tcgagctttt gtcatgatgg tgtccataac cgcggctgtg cagcgtcacc gcgaggcgca  2220
tttgccgttc ctggtgtatt tgcgcaatcc cacgatgggt ggcgccatgg cctcgtgggg  2280
ttcatctggg catctcactt ttgcggaacc cggcgcgcag ataggtttcc tgggtcctcg  2340
cgtggtggag ttaaccactg gcatgcgct tccagacggt gtgcagcagg cggagaattt   2400
ggtgaaaact ggtgtgattg atggaattgt gtcgccactc caattgcgtg cagcggtggc  2460
aaaaaccctc aaggttattc agccggtaga ggcaacggat cgttttctc caacaactcc   2520
tggcgtggca cttccggtga tggaggcgat tgcgcgttct cgtgacccgc agaggcctgg  2580
aatcggggag attatggaaa cgttgggggc agacgtcgtc aagctttctg gtgcgcgtgc  2640
tggcgcattg agcccggctg tgcgcgttgc cctggcgcgc atcggggggcc ggcccgtggt 2700
gctgattggg caggatcgcc gcttcacgct gggccgcag gagctgcgtt ttgcgcgtcg   2760
tggcatttcg ctggcgcgcg agctaaacct gccgatcgtg tccatcatcg acacctccgg  2820
cgccgaattg tcgcaggcgg ctgaggagct cggcatcgca agctcgattg cgcgcacctt  2880
gtccaagctt atcgacgctc ccctccccac cgtttcggtc attattggtc agggcgttgg  2940
cggtggcgcg ctggccatgc tgcccgccga tctggtctac gcggccgaaa acgcgtggct  3000
gtccgcattg ccaccagagg gcgcctcggc catcctcttc cgcgacacca accacgccgc  3060
ggaaatcata gagcgacaag gcgtgcaggc gcacgcactt ttaagccaag gcttatcga   3120
cgggatcgtc gccgaaaccg agcactttgt tgaagaaatt ctcggcacaa tcagcaacgc  3180
cctctccgaa ttggataaca atccggagag ggcgggacgc gacagtcgct tcacacgatt  3240
tgagcgttta gcgcagtaa                                               3259
```

<210> SEQ ID NO 26
<211> LENGTH: 591
<212> TYPE: PRT
<213> ORGANISM: Artificial sequence
<220> FEATURE:
<223> OTHER INFORMATION: synthetic peptide

<400> SEQUENCE: 26

```
Met Ser Val Glu Thr Arg Lys Ile Thr Lys Val Leu Val Ala Asn Arg
1               5                   10                  15

Gly Glu Ile Ala Ile Arg Val Phe Arg Ala Ala Arg Asp Glu Gly Ile
                20                  25                  30

Gly Ser Val Ala Val Tyr Ala Glu Pro Asp Ala Asp Ala Pro Phe Val
            35                  40                  45

Ser Tyr Ala Asp Glu Ala Phe Ala Leu Gly Gly Gln Thr Ser Ala Glu
50                  55                  60

Ser Tyr Leu Val Ile Asp Lys Ile Ile Asp Ala Ala Arg Lys Ser Gly
65                  70                  75                  80

Ala Asp Ala Ile His Pro Gly Tyr Gly Phe Leu Ala Glu Asn Ala Asp
                85                  90                  95

Phe Ala Glu Ala Val Ile Asn Glu Gly Leu Ile Trp Ile Gly Pro Ser
                100                 105                 110

Pro Glu Ser Ile Arg Ser Leu Gly Asp Lys Val Thr Ala Arg His Ile
            115                 120                 125

Ala Asp Thr Ala Lys Ala Pro Met Ala Pro Gly Thr Lys Glu Pro Val
130                 135                 140

Lys Asp Ala Ala Glu Val Val Ala Phe Ala Glu Glu Phe Gly Leu Pro
145                 150                 155                 160

Ile Ala Ile Lys Ala Ala Phe Gly Gly Gly Gly Arg Gly Met Lys Val
                165                 170                 175

Ala Tyr Lys Met Glu Glu Val Ala Asp Leu Phe Glu Ser Ala Thr Arg
                180                 185                 190

Glu Ala Thr Ala Ala Phe Gly Arg Gly Glu Cys Phe Val Glu Arg Tyr
            195                 200                 205

Leu Asp Lys Ala Arg His Val Glu Ala Gln Val Ile Ala Asp Lys His
210                 215                 220

Gly Asn Val Val Ala Gly Thr Arg Asp Cys Ser Leu Gln Arg Arg
225                 230                 235                 240

Phe Gln Lys Leu Val Glu Glu Ala Pro Ala Pro Phe Leu Thr Asp Asp
                245                 250                 255

Gln Arg Glu Arg Leu His Ser Ser Ala Lys Ala Ile Cys Lys Glu Ala
            260                 265                 270

Gly Tyr Tyr Gly Ala Gly Thr Val Glu Tyr Leu Val Gly Ser Asp Gly
            275                 280                 285

Leu Ile Ser Phe Leu Glu Val Asn Thr Arg Leu Gln Val Glu His Pro
290                 295                 300

Val Thr Glu Glu Thr Thr Gly Ile Asp Leu Val Arg Glu Met Phe Arg
305                 310                 315                 320

Ile Ala Glu Gly His Glu Leu Ser Ile Lys Asp Pro Ala Pro Arg
                325                 330                 335

Gly His Ala Phe Glu Phe Arg Ile Asn Gly Glu Asp Ala Gly Ser Asn
            340                 345                 350

Phe Met Pro Ala Pro Gly Lys Ile Thr Ser Tyr Arg Glu Pro Gln Gly
            355                 360                 365
```

Pro Gly Val Arg Met Asp Ser Gly Val Glu Gly Glu Ile Ser
    370                 375                 380

Gly Gln Phe Asp Ser Met Leu Ala Lys Leu Ile Val Trp Gly Asp Thr
385                 390                 395                 400

Arg Glu Gln Ala Leu Gln Arg Ser Arg Arg Ala Leu Ala Glu Tyr Val
            405                 410                 415

Val Glu Gly Met Pro Thr Val Ile Pro Phe His Gln His Ile Val Glu
        420                 425                 430

Asn Pro Ala Phe Val Gly Asn Asp Glu Gly Phe Glu Ile Tyr Thr Lys
            435                 440                 445

Trp Ile Glu Glu Val Trp Asp Asn Pro Ile Ala Pro Tyr Val Asp Ala
    450                 455                 460

Ser Glu Leu Asp Glu Asp Glu Asp Lys Thr Pro Ala Gln Lys Val Val
465                 470                 475                 480

Val Glu Ile Asn Gly Arg Arg Val Glu Val Ala Leu Pro Gly Asp Leu
            485                 490                 495

Ala Leu Gly Gly Thr Ala Gly Pro Lys Lys Ala Lys Lys Arg Arg
            500                 505                 510

Ala Gly Gly Ala Lys Ala Gly Val Ser Gly Asp Ala Val Ala Ala Pro
    515                 520                 525

Met Gln Gly Thr Val Ile Lys Val Asn Val Glu Glu Gly Ala Glu Val
    530                 535                 540

Asn Glu Gly Asp Thr Val Val Leu Glu Ala Met Lys Met Glu Asn
545                 550                 555                 560

Pro Val Lys Ala His Lys Ser Gly Thr Val Thr Gly Leu Thr Val Ala
            565                 570                 575

Ala Gly Glu Gly Val Asn Lys Gly Val Val Leu Leu Glu Ile Lys
            580                 585                 590

<210> SEQ ID NO 27
<211> LENGTH: 484
<212> TYPE: PRT
<213> ORGANISM: Artificial sequence
<220> FEATURE:
<223> OTHER INFORMATION: synthetic peptide

<400> SEQUENCE: 27

Met Val Trp Gly Met Glu His Thr Ser Ala Leu Thr Leu Ile Asp Ser
1               5                   10                  15

Val Leu Asp Pro Asp Ser Phe Ile Ser Trp Asn Glu Thr Pro Gln Tyr
            20                  25                  30

Asp Asn Leu Asn Gln Gly Tyr Ala Glu Thr Leu Glu Arg Ala Arg Ser
        35                  40                  45

Lys Ala Lys Cys Asp Glu Ser Val Ile Thr Gly Glu Gly Thr Val Glu
    50                  55                  60

Gly Ile Pro Val Ala Val Ile Leu Ser Asp Phe Ser Phe Leu Gly Gly
65                  70                  75                  80

Ser Leu Gly Thr Val Ala Ser Val Arg Ile Met Lys Ala Ile His Arg
                85                  90                  95

Ala Thr Glu Leu Lys Leu Pro Leu Leu Val Ser Pro Ala Ser Gly Gly
            100                 105                 110

Ala Arg Met Gln Glu Asp Asn Arg Ala Phe Val Met Met Val Ser Ile
        115                 120                 125

Thr Ala Ala Val Gln Arg His Arg Glu Ala His Leu Pro Phe Leu Val
    130                 135                 140

```
Tyr Leu Arg Asn Pro Thr Met Gly Gly Ala Met Ala Ser Trp Gly Ser
145                 150                 155                 160

Ser Gly His Leu Thr Phe Ala Glu Pro Gly Ala Gln Ile Gly Phe Leu
                165                 170                 175

Gly Pro Arg Val Val Glu Leu Thr Thr Gly His Ala Leu Pro Asp Gly
            180                 185                 190

Val Gln Gln Ala Glu Asn Leu Val Lys Thr Gly Val Ile Asp Gly Ile
        195                 200                 205

Val Ser Pro Leu Gln Leu Arg Ala Ala Val Lys Thr Leu Lys Val
210                 215                 220

Ile Gln Pro Val Glu Ala Thr Asp Arg Phe Ser Pro Thr Thr Pro Gly
225                 230                 235                 240

Val Ala Leu Pro Val Met Glu Ala Ile Ala Arg Ser Arg Asp Pro Gln
                245                 250                 255

Arg Pro Gly Ile Gly Glu Ile Met Glu Thr Leu Gly Ala Asp Val Val
            260                 265                 270

Lys Leu Ser Gly Ala Arg Ala Gly Ala Leu Ser Pro Ala Val Arg Val
        275                 280                 285

Ala Leu Ala Arg Ile Gly Gly Arg Pro Val Val Leu Ile Gly Gln Asp
290                 295                 300

Arg Arg Phe Thr Leu Gly Pro Gln Glu Leu Arg Phe Ala Arg Arg Gly
305                 310                 315                 320

Ile Ser Leu Ala Arg Glu Leu Asn Leu Pro Ile Val Ser Ile Ile Asp
                325                 330                 335

Thr Ser Gly Ala Glu Leu Ser Gln Ala Ala Glu Glu Leu Gly Ile Ala
            340                 345                 350

Ser Ser Ile Ala Arg Thr Leu Ser Lys Leu Ile Asp Ala Pro Leu Pro
        355                 360                 365

Thr Val Ser Val Ile Ile Gly Gln Gly Val Gly Gly Gly Ala Leu Ala
370                 375                 380

Met Leu Pro Ala Asp Leu Val Tyr Ala Ala Glu Asn Ala Trp Leu Ser
385                 390                 395                 400

Ala Leu Pro Pro Glu Gly Ala Ser Ala Ile Leu Phe Arg Asp Thr Asn
                405                 410                 415

His Ala Ala Glu Ile Ile Glu Arg Gln Gly Val Gln Ala His Ala Leu
            420                 425                 430

Leu Ser Gln Gly Leu Ile Asp Gly Ile Val Ala Glu Thr Glu His Phe
        435                 440                 445

Val Glu Glu Ile Leu Gly Thr Ile Ser Asn Ala Leu Ser Glu Leu Asp
450                 455                 460

Asn Asn Pro Glu Arg Ala Gly Arg Asp Ser Arg Phe Thr Arg Phe Glu
465                 470                 475                 480

Arg Leu Ala Gln
```

<210> SEQ ID NO 28
<211> LENGTH: 686
<212> TYPE: DNA
<213> ORGANISM: Artificial sequence
<220> FEATURE:
<223> OTHER INFORMATION: synthetic nucleotide

<400> SEQUENCE: 28

```
caggaggaat taacatgaaa cctaaaatca ttagtaaagt gtcattagtt gcctttctgt      60
tactgtcact ggccgcaagt ttagcgaatg cacagagtga acctgtgtat agtcgcggcg     120
```

```
attgggttgt tggcttaaat gctactagag tgctgacgga tgaggacctg cgtagcgcct    180
cagccggctc agctccggtt ccgaactcaa atttgagcat caacaacgat acgaccgtga    240
gttttgatgt gagctatttt ctgagcaatc agttagcctt taatatcttt ggtggcatcc    300
ctgcgagtgc cgatctacag ggcgaagaat cactgagcgg cctgtttctg ggccagacag    360
attatggtcc ggttatcctg tctctacagt atcatgtgct gacgggtagc aattttagtc    420 catatttgg tgcaggtgtg ggtcgtatct tatttctgga tgaaaaagat cgcgcactga    480
ccgattttga tgtggaagat acatgggcac cagccgttca ggcaggcttt cgctggcgca    540
ttcataataa ctggagcgcc aattttgatg ttcgctatgc cccgtttgaa gcggatatta    600
ccggtaatct gggtccagct ccagttcagg ccaaagtgga agtagaccct accatcgtgt    660
ctatcggcgt tgcgtatcgc ttttaa                                        686
```

<210> SEQ ID NO 29
<211> LENGTH: 223
<212> TYPE: PRT
<213> ORGANISM: Artificial sequence
<220> FEATURE:
<223> OTHER INFORMATION: synthetic peptide

<400> SEQUENCE: 29

```
Met Lys Pro Lys Ile Ile Ser Lys Val Ser Leu Val Ala Phe Leu Leu
1               5                   10                  15

Leu Ser Leu Ala Ala Ser Leu Ala Asn Ala Gln Ser Glu Pro Val Tyr
                20                  25                  30

Ser Arg Gly Asp Trp Val Val Gly Leu Asn Ala Thr Arg Val Leu Thr
            35                  40                  45

Asp Glu Asp Leu Arg Ser Ala Ser Ala Gly Ser Ala Pro Val Pro Asn
        50                  55                  60

Ser Asn Leu Ser Ile Asn Asn Asp Thr Thr Val Ser Phe Asp Val Ser
65                  70                  75                  80

Tyr Phe Leu Ser Asn Gln Leu Ala Phe Asn Ile Phe Gly Gly Ile Pro
                85                  90                  95

Ala Ser Ala Asp Leu Gln Gly Glu Glu Ser Leu Ser Gly Leu Phe Leu
            100                 105                 110

Gly Gln Thr Asp Tyr Gly Pro Val Ile Leu Ser Leu Gln Tyr His Val
        115                 120                 125

Leu Thr Gly Ser Asn Phe Ser Pro Tyr Phe Gly Ala Gly Val Gly Arg
    130                 135                 140

Ile Leu Phe Leu Asp Glu Lys Asp Arg Ala Leu Thr Asp Phe Asp Val
145                 150                 155                 160

Glu Asp Thr Trp Ala Pro Ala Val Gln Ala Gly Phe Arg Trp Arg Ile
                165                 170                 175

His Asn Asn Trp Ser Ala Asn Phe Asp Val Arg Tyr Ala Pro Phe Glu
            180                 185                 190

Ala Asp Ile Thr Gly Asn Leu Gly Pro Ala Pro Val Gln Ala Lys Val
        195                 200                 205

Glu Val Asp Pro Thr Ile Val Ser Ile Gly Val Ala Tyr Arg Phe
    210                 215                 220
```

<210> SEQ ID NO 30
<211> LENGTH: 4792
<212> TYPE: DNA
<213> ORGANISM: Artificial sequence
<220> FEATURE:

<223> OTHER INFORMATION: synthetic nucleotide

<400> SEQUENCE: 30

```
aatgtgcctg tcaaatggac gaagcaggga ttctgcaaac cctatgctac tccgtcaagc      60
cgtcaattgt ctgattcgtt accaattatg acaacttgac ggctacatca ttcactttt     120
cttcacaacc ggcacggaac tcgctcgggc tggccccggt gcatttttta aatacccgcg    180
agaaatagag ttgatcgtca aaccaacat tgcgaccgac ggtggcgata ggcatccggg     240
tggtgctcaa aagcagcttc gcctggctga tacgttggtc ctcgcgccag cttaagacgc    300
taatccctaa ctgctggcgg aaaagatgtg acagacgcga cggcgacaag caaacatgct    360
gtgcgacgct ggcgatatca aaattgctgt ctgccaggtg atcgctgatg tactgacaag    420
cctcgcgtac ccgattatcc atcggtggat ggagcgactc gttaatcgct tccatgcgcc    480
gcagtaacaa ttgctcaagc agatttatcg ccagcagctc cgaatagcgc ccttccccctt    540
gcccggcgtt aatgatttgc ccaaacaggt cgctgaaatg cggctggtgc gcttcatccg    600
ggcgaaagaa cccgtattg gcaaatattg acggccagtt aagccattca tgccagtagg    660
cgcgcggacg aaagtaaacc cactggtgat accattcgcg agcctccgga tgacgaccgt    720
agtgatgaat ctctcctggc gggaacagca aaatatcacc cggtcggcaa acaaattctc    780
gtccctgatt tttcaccacc ccctgaccgc gaatggtgag attgagaata taaccttca    840
ttcccagcgg tcggtcgata aaaaaatcga gataaccgtt ggcctcaatc ggcgttaaac    900
ccgccaccag atgggcatta acgagtatc ccggcagcag gggatcattt tgcgcttcag    960
ccatactttt catactcccg ccattcagag aagaaaccaa ttgtccatat tgcatcagac   1020
attgccgtca ctgcgtcttt tactggctct tctcgctaac caaaccggta accccgctta   1080
ttaaaagcat tctgtaacaa agcgggacca aagccatgaa aaaaacgcgt aacaaaagtg   1140
tctataatca cggcagaaaa gtccacattg attatttgca cggcgtcaca ctttgctatg   1200
ccatagcatt tttatccata agattagcgg atcctacctg acgcttttta tcgcaactct   1260
ctactgtttc tccatacccg ttttttgggc taacaggagg aattaaccat gggtacctct   1320
catcatcatc atcatcacag cagcggcctg gtgccgcgcg gcagcctcga gggtagatct   1380
ggtactagtg gtgaattcgg tgagctcggt ctgcagctgg tgccgcgcgg cagccaccac   1440
caccaccacc actaatacag attaaatcag aacgcagaag cggtctgata aaacagaatt   1500
tgcctggcgg cagtagcgcg gtggtcccac ctgaccccat gccgaactca gaagtgaaac   1560
gccgtagcgc cgatggtagt gtggggtctc cccatgcgag agtagggaac tgccaggcat   1620
caaataaaac gaaaggctca gtcgaaagac tgggcctttc gtcgaccaga cccgccataa   1680
aacgccctga gaagcccgtg acgggctttt cttgtattat gggtagtttc cttgcatgaa   1740
tccataaaag gcgcctgtag tgccatttac ccccattcac tgccagagcc gtgagcgcag   1800
cgaactgaat gtcacgaaaa agacagcgac tcaggtgcct gatggtcgga gacaaaagga   1860
atattcagcg atttgcccga gcttgcgagg gtgctactta agcctttagg gttttaaggt   1920
ctgtttttgta gaggagcaaa cagcgtttgc gacatccttt tgtaatactg cggaactgac   1980
taaagtagtg agttatacac agggctggga tctattcttt ttatcttttt ttattctttc   2040
tttattctat aaattataac cacttgaata taaacaaaaa aaacacacaa aggtctagcg   2100
gaatttacag agggtctagc agaatttaca agttttccag caaaggtcta gcagaattta   2160
cagataccca caactcaaag gaaaaggtct agtaattatc attgactagc ccatctcaat   2220
tggtatagtg attaaaatca cctagaccaa ttgagatgta tgtctgaatt agttgttttc   2280
```

```
aaagcaaatg aactagcgat tagtcgctat gacttaacgg agcatgaaac caagctaatt      2340
ttatgctgtg tggcactact caaccccacg attgaaaacc ctacaaggaa agaacggacg      2400
gtatcgttca cttataacca atacgctcag atgatgaaca tcagtaggga aaatgcttat      2460
ggtgtattag ctaaagcaac cagagagctg atgacgagaa ctgtggaaat caggaatcct      2520
ttggttaaag gctttgagat tttccagtgg acaaactatg ccaagttctc aagcgaaaaa      2580
ttagaattag tttttagtga agagatattg ccttatcttt tccagttaaa aaaattcata      2640
aaatataatc tggaacatgt taagtctttt gaaaacaaat actctatgag gatttatgag      2700
tggttattaa agaactaac acaaaagaaa actcacaagg caaatataga gattagcctt       2760
gatgaattta agttcatgtt aatgcttgaa ataactacc atgagtttaa aaggcttaac        2820
caatgggttt tgaaaccaat aagtaaagat ttaaacactt acagcaatat gaaattggtg      2880
gttgataagc gaggccgccc gactgatacg ttgatttttcc aagttgaact agatagacaa     2940
atggatctcg taaccgaact tgagaacaac cagataaaaa tgaatggtga caaaatacca      3000
acaaccatta catcagattc ctacctacgt aacggactaa gaaaaacact acacgatgct      3060
ttaactgcaa aaattcagct caccagtttt gaggcaaaat ttttgagtga catgcaaagt     3120
aagcatgatc tcaatggttc gttctcatgg ctcacgcaaa acaacgaac cacactagag       3180 aacatactgg ctaaatacgg aaggatctga ggttcttatg gctcttgtat ctatcagtga     3240
agcatcaaga ctaacaaaca aaagtagaac aactgttcac cgttagatat caaagggaaa    3300
actgtcgata tgcacagatg aaaacggtgt aaaaaagata gatacatcag agcttttacg    3360 agttttttggt gcatttaaag ctgttcacca tgaacagatc gacaatgtaa cagatgaaca   3420
gcatgtaaca cctaatagaa caggtgaaac cagtaaaaca aagcaactag aacatgaaat     3480
tgaacacctg agacaacttg ttacagctca acagtcacac atagacagcc tgaaacaggc    3540
gatgctgctt atcgaatcaa agctgccgac aacacgggag ccagtgacgc ctcccgtggg    3600
gaaaaaatca tggcaattct ggaagaaata gcgctttcag ccggcaaacc tgaagccgga   3660
tctgcgattc tgataacaaa ctagcaacac cagaacagcc cgtttgcggg cagcaaaacc   3720
cgcggccgcc tatttgttta ttttttctaaa tacattcaaa tatgtatccg ctcatgagac    3780
aataaccctg ataaatgctt caataatatt gaaaaaggaa gagtatgagg gaagcggtga   3840
tcgccgaagt atcgactcaa ctatcagagg tagttggcgt catcgagcgc catctcgaac    3900
cgacgttgct ggccgtacat ttgtacggct ccgcagtgga tggcggcctg aagccacaca    3960
gtgatattga tttgctggtt acggtgaccg taaggcttga tgaaacaacg cggcgagctt    4020
tgatcaacga ccttttggaa acttcggctt ccctggaga gagcgagatt ctccgcgctg     4080
tagaagtcac cattgttgtg cacgacgaca tcattccgtg gcgttatcca gctaagcgcg    4140
aactgcaatt tggagaatgg cagcgcaatg acattcttgc aggtatcttc gagccagcca    4200
cgatcgacat tgatctggct atcttgctga caaaagcaag agaacatagc gttgccttgg    4260
taggtccagc ggcggaggaa ctctttgatc cggttcctga acaggatcta tttgaggcgc    4320
taaatgaaac cttaacgcta tggaactcgc cgcccgactg gctggcgat gagcgaaatg      4380 tagtgcttac gttgtcccgc atttggtaca gcgcagtaac cggcaaaatc gcgccgaagg    4440
atgtcgctgc cgactgggca atggagcgcc tgccggccca gtatcagccc gtcatacttg    4500
aagctagaca ggcttatctt ggacaagaag aagatcgctt ggcctcgcgc gcagatcagt    4560
tggaagaatt tgtccactac gtgaaaggcg agatcaccaa ggtagtcggc aaataatgtc     4620
```

```
taacaattcg ttcaagccga ggggccgcaa gatccggcca cgatgacccg gtcgtcggtt    4680
cagggcaggg tcgttaaata gccgcttatg tctattgctg gtttaccggt ttattgacta    4740
ccggaagcag tgtgaccgtg tgcttctcaa atgcctgagg tttcaggcat gc            4792
```

<210> SEQ ID NO 31
<211> LENGTH: 1266
<212> TYPE: DNA
<213> ORGANISM: Artificial sequence
<220> FEATURE:
<223> OTHER INFORMATION: synthetic nucleotide

<400> SEQUENCE: 31

```
atgagcaaca atgaattcca tcagcgtcgt ctttctgcca ctccgcgcgg ggttggcgtg      60
atgtgtaact tcttcgccca gtcggctgaa aacgccacgc tgaaggatgt tgagggcaac     120
gagtacatcg atttcgccgc aggcattgcg gtgctgaata ccggacatcg ccaccctgat     180
ctggtcgcgg cggtggagca gcaactgcaa cagtttaccc acaccgcgta tcagattgtg     240
ccgtatgaaa gctacgtcac cctggcggag aaaatcaacg cccttgcccc ggtgagcggg     300
caggccaaaa ccgcgttctt caccaccggt gcggaagcgg tggaaaacgc ggtgaaaatt     360
gctcgcgccc ataccggacg ccctggcgtg attgcgttta gcggcggctt tcacggtcgt     420
acgtatatga ccatggcgct gaccggaaaa gttgcgccgt acaaaatcgg cttcggcccg     480
ttccctggtt cggtgtatca cgtaccttat ccgtcagatt tacacggcat ttcaacacag     540
gactccctcg acgccatcga acgcttgttt aaatcagaca tcgaagcgaa gcaggtggcg     600
gcgattattt tcgaaccggt gcagggcgag ggcggtttca acgttgcgcc aaaagagctg     660
gttgccgcta ttcgccgcct gtgcgacgag cacggtattg tgatgattgc tgatgaagtg     720
caaagcggct ttgcgcgtac cggtaagctg tttgccatgg atcattacgc cgataagccg     780
gatttaatga cgatggcgaa aagcctcgcg ggcgggatgc cgctttcggg cgtggtcggt     840
aacgcgaata ttatggacgc acccgcgccg ggcgggcttg gcggcaccta cgccggtaac     900
ccgctggcgg tggctgccgc gcacgcggtg ctcaacatta tcgacaaaga tcactctgc      960 gaacgcgcga tcaactgggg ccagcgtctc aaaaacacgt tgattgatgc aaagaaagc     1020 gttccggcca ttgctgcggt acgcggcctg gggtcgatga ttgcggtaga gtttaacgat    1080
ccgcaaacgg gcgagccgtc agcggcgatt gcacagaaaa tccagcaacg cgcgctggcg    1140
caggggctgc tcctgctgac ctgtggcgca tacggcaacg tgattcgctt cctgtatccg    1200
ctgaccatcc cggatgcgca attcgatgcg gcaatgaaaa ttttgcagga tgcgctgagc    1260
gattaa                                                              1266
```

<210> SEQ ID NO 32
<211> LENGTH: 421
<212> TYPE: PRT
<213> ORGANISM: Artificial sequence
<220> FEATURE:
<223> OTHER INFORMATION: synthetic peptide

<400> SEQUENCE: 32

```
Met Ser Asn Asn Glu Phe His Gln Arg Arg Leu Ser Ala Thr Pro Arg
1               5                   10                  15

Gly Val Gly Val Met Cys Asn Phe Phe Ala Gln Ser Ala Glu Asn Ala
            20                  25                  30

Thr Leu Lys Asp Val Glu Gly Asn Glu Tyr Ile Asp Phe Ala Ala Gly
        35                  40                  45
```

Ile Ala Val Leu Asn Thr Gly His Arg His Pro Asp Leu Val Ala Ala
 50                 55                  60

Val Glu Gln Gln Leu Gln Gln Phe Thr His Thr Ala Tyr Gln Ile Val
 65                  70                  75                  80

Pro Tyr Glu Ser Tyr Val Thr Leu Ala Glu Lys Ile Asn Ala Leu Ala
                 85                  90                  95

Pro Val Ser Gly Gln Ala Lys Thr Ala Phe Phe Thr Thr Gly Ala Glu
            100                 105                 110

Ala Val Glu Asn Ala Val Lys Ile Ala Arg Ala His Thr Gly Arg Pro
                115                 120                 125

Gly Val Ile Ala Phe Ser Gly Phe His Gly Arg Thr Tyr Met Thr
130                 135                 140

Met Ala Leu Thr Gly Lys Val Ala Pro Tyr Lys Ile Gly Phe Gly Pro
145                 150                 155                 160

Phe Pro Gly Ser Val Tyr His Val Pro Tyr Pro Ser Asp Leu His Gly
                165                 170                 175

Ile Ser Thr Gln Asp Ser Leu Asp Ala Ile Glu Arg Leu Phe Lys Ser
            180                 185                 190

Asp Ile Glu Ala Lys Gln Val Ala Ala Ile Phe Glu Pro Val Gln
            195                 200                 205

Gly Glu Gly Gly Phe Asn Val Ala Pro Lys Glu Leu Val Ala Ala Ile
210                 215                 220

Arg Arg Leu Cys Asp Glu His Gly Ile Val Met Ile Ala Asp Glu Val
225                 230                 235                 240

Gln Ser Gly Phe Ala Arg Thr Gly Lys Leu Phe Ala Met Asp His Tyr
                245                 250                 255

Ala Asp Lys Pro Asp Leu Met Thr Met Ala Lys Ser Leu Ala Gly Gly
            260                 265                 270

Met Pro Leu Ser Gly Val Val Gly Asn Ala Asn Ile Met Asp Ala Pro
275                 280                 285

Ala Pro Gly Gly Leu Gly Gly Thr Tyr Ala Gly Asn Pro Leu Ala Val
            290                 295                 300

Ala Ala His Ala Val Leu Asn Ile Ile Asp Lys Glu Ser Leu Cys
305                 310                 315                 320

Glu Arg Ala Asn Gln Leu Gly Gln Arg Leu Lys Asn Thr Leu Ile Asp
                325                 330                 335

Ala Lys Glu Ser Val Pro Ala Ile Ala Ala Val Arg Gly Leu Gly Ser
            340                 345                 350

Met Ile Ala Val Glu Phe Asn Asp Pro Gln Thr Gly Glu Pro Ser Ala
355                 360                 365

Ala Ile Ala Gln Lys Ile Gln Gln Arg Ala Leu Ala Gln Gly Leu Leu
            370                 375                 380

Leu Leu Thr Cys Gly Ala Tyr Gly Asn Val Ile Arg Phe Leu Tyr Pro
385                 390                 395                 400

Leu Thr Ile Pro Asp Ala Gln Phe Asp Ala Ala Met Lys Ile Leu Gln
                405                 410                 415

Asp Ala Leu Ser Asp
            420

<210> SEQ ID NO 33
<211> LENGTH: 1289
<212> TYPE: DNA
<213> ORGANISM: Artificial sequence
<220> FEATURE:
<223> OTHER INFORMATION: synthetic nucleotide

<400> SEQUENCE: 33

```
caggaggaat taacatgtca gcaaagcaag tctcgaaaga tgaagaaaaa gaagctctta      60
acttatttct gtctacccaa acaatcatta aggaagccct tcggaagctg ggttatccgg     120
gagatatgta tgaactcatg aaagagccgc agagaatgct cactgtccgc attccggtca     180
aaatggacaa tgggagcgtc aaagtgttca caggctaccg gtcacagcac aatgatgctg     240
tcggtccgac aaagggggc gttcgcttcc atccagaagt taatgaagag gaagtaaagg     300
cattatccat ttggatgacg ctcaaatgcg ggattgccaa tcttccttac ggcggcggga     360
agggcggtat tatttgtgat ccgcggacaa tgtcatttgg agaactggaa aggctgagca     420
gggggtatgt ccgtgccatc agccagatcg tcggtccgac aaaggatatt ccagctcccg     480
atgtgtacac caattcgcag attatggcgt ggatgatgga tgagtacagc cggctgcggg     540
aattcgattc tccgggcttt attacaggta aaccgcttgt tttgggagga tcgcaaggac     600
gggaaacagc gacggcacag ggcgtcacga tttgtattga agaggcggtg aagaaaaaag     660
ggatcaagct gcaaaacgcg cgcatcatca tacagggctt tggaaacgcg ggtagcttcc     720
tggccaaatt catgcacgat gcgggcgcga aggtgatcgg gatttctgat gccaatggcg     780
ggctctacaa cccagacggc cttgatatcc cttatttgct cgataaacgg gacagctttg     840
gtatggtcac caattattt actgacgtca tcacaaatga ggagctgctt gaaaaggatt     900
gcgatatttt agtgcctgcc gcgatctcca atcaaatcac agccaaaaac gcacataaca     960
ttcaggcgtc aatcgtcgtt gaagcggcga acggcccgac aaccattgat gccactaaga    1020
tcctgaatga agaggcgtg ctgcttgtgc cggatatcct agcgagtgcc ggcggcgtca    1080
cggtttctta ttttgaatgg gtgcaaaaca accaaggata ttattggtcg aagaagagg    1140
ttgcagaaaa actgagaagc gtcatggtca gctcgttcga acaatttat caaacagcgg    1200
caacacataa agtggatatg cgtttggcgg cttacatgac gggcatcaga aaatcggcag    1260
aagcatcgcg tttccgcgga tgggtctaa                                      1289
```

<210> SEQ ID NO 34
<211> LENGTH: 424
<212> TYPE: PRT
<213> ORGANISM: Artificial sequence
<220> FEATURE:
<223> OTHER INFORMATION: synthetic peptide

<400> SEQUENCE: 34

```
Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
            20                  25                  30

Gly Tyr Pro Gly Asp Met Tyr Glu Leu Met Lys Glu Pro Gln Arg Met
        35                  40                  45

Leu Thr Val Arg Ile Pro Val Lys Met Asp Asn Gly Ser Val Lys Val
    50                  55                  60

Phe Thr Gly Tyr Arg Ser Gln His Asn Asp Ala Val Gly Pro Thr Lys
65                  70                  75                  80

Gly Gly Val Arg Phe His Pro Glu Val Asn Glu Glu Val Lys Ala
                85                  90                  95

Leu Ser Ile Trp Met Thr Leu Lys Cys Gly Ile Ala Asn Leu Pro Tyr
            100                 105                 110

Gly Gly Gly Lys Gly Gly Ile Ile Cys Asp Pro Arg Thr Met Ser Phe
```

```
                115                 120                 125
Gly Glu Leu Glu Arg Leu Ser Arg Gly Tyr Val Arg Ala Ile Ser Gln
            130                 135                 140

Ile Val Gly Pro Thr Lys Asp Ile Pro Ala Pro Asp Val Tyr Thr Asn
145                 150                 155                 160

Ser Gln Ile Met Ala Trp Met Met Asp Glu Tyr Ser Arg Leu Arg Glu
                165                 170                 175

Phe Asp Ser Pro Gly Phe Ile Thr Gly Lys Pro Leu Val Leu Gly Gly
            180                 185                 190

Ser Gln Gly Arg Glu Thr Ala Thr Ala Gln Gly Val Thr Ile Cys Ile
                195                 200                 205

Glu Glu Ala Val Lys Lys Gly Ile Lys Leu Gln Asn Ala Arg Ile
            210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
            245                 250                 255

Leu Tyr Asn Pro Asp Gly Leu Asp Ile Pro Tyr Leu Leu Asp Lys Arg
                260                 265                 270

Asp Ser Phe Gly Met Val Thr Asn Leu Phe Thr Asp Val Ile Thr Asn
            275                 280                 285

Glu Glu Leu Leu Glu Lys Asp Cys Asp Ile Leu Val Pro Ala Ala Ile
            290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                325                 330                 335

Leu Asn Glu Arg Gly Val Leu Leu Val Pro Asp Ile Leu Ala Ser Ala
            340                 345                 350

Gly Gly Val Thr Val Ser Tyr Phe Glu Trp Val Gln Asn Asn Gln Gly
                355                 360                 365

Tyr Tyr Trp Ser Glu Glu Val Ala Glu Lys Leu Arg Ser Val Met
370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
                405                 410                 415

Ala Ser Arg Phe Arg Gly Trp Val
            420

<210> SEQ ID NO 35
<211> LENGTH: 3650
<212> TYPE: DNA
<213> ORGANISM: Artificial sequence
<220> FEATURE:
<223> OTHER INFORMATION: synthetic nucleotide

<400> SEQUENCE: 35
aatgtgcctg tcaaatggac gaagcaggga ttctgcaaac cctatgctac tccgtcaagc      60
cgtcaattgt ctgattcgtt accaattatg acaacttgac ggctacatca ttcactttt     120 cttcacaacc ggcacggaac tcgctcgggc tggccccggt gcattttta aatacccgcg     180 agaaatagag ttgatcgtca aaaccaacat tgcgaccgac ggtggcgata ggcatccggg     240
tggtgctcaa aagcagcttc gcctggctga tacgttggtc ctcgcgccag cttaagacgc     300
```

| | |
|---|---|
| taatccctaa ctgctggcgg aaaagatgtg acagacgcga cggcgacaag caaacatgct | 360 |
| gtgcgacgct ggcgatatca aaattgctgt ctgccaggtg atcgctgatg tactgacaag | 420 |
| cctcgcgtac ccgattatcc atcggtggat ggagcgactc gttaatcgct ccatgcgcc | 480 |
| gcagtaacaa ttgctcaagc agatttatcg ccagcagctc cgaatagcgc cttcccctt | 540 |
| gcccggcgtt aatgatttgc ccaaacaggt cgctgaaatg cggctggtgc gcttcatccg | 600 |
| ggcgaaagaa ccccgtattg gcaaatattg acggccagtt aagccattca tgccagtagg | 660 |
| cgcgcggacg aaagtaaacc cactggtgat accattcgcg agcctccgga tgacgaccgt | 720 |
| agtgatgaat ctctcctggc gggaacagca aaatatcacc cggtcggcaa acaaattctc | 780 |
| gtccctgatt tttcaccacc ccctgaccgc gaatggtgag attgagaata taacctttca | 840 |
| ttcccagcgg tcggtcgata aaaaaatcga gataaccgtt ggcctcaatc ggcgttaaac | 900 |
| ccgccaccag atgggcatta acgagtatc ccggcagcag gggatcattt tgcgcttcag | 960 |
| ccatactttt catactcccg ccattcagag aagaaaccaa ttgtccatat tgcatcagac | 1020 |
| attgccgtca ctgcgtcttt tactggctct ctcgctaac caaaccggta accccgctta | 1080 |
| ttaaaagcat tctgtaacaa agcgggacca aagccatgac aaaaacgcgt aacaaaagtg | 1140 |
| tctataatca cggcagaaaa gtccacattg attatttgca cggcgtcaca ctttgctatg | 1200 |
| ccatagcatt tttatccata agattagcgg atcctacctg acgcttttta tcgcaactct | 1260 |
| ctactgtttc tccatacccg ttttttgggc taacaggagg aattaaccat gggtacctct | 1320 |
| catcatcatc atcatcacag cagcggcctg gtgccgcgcg gcagcctcga gggtagatct | 1380 |
| ggtactagtg gtgaattcgg tgagctcggt ctgcagctgg tgccgcgcgg cagccaccac | 1440 |
| caccaccacc actaatacag attaaatcag aacgcagaag cggtctgata aaacagaatt | 1500 |
| tgcctggcgg cagtagcgcg gtggtcccac ctgaccccat gccgaactca gaagtgaaac | 1560 |
| gccgtagcgc cgatggtagt gtggggtctc cccatgcgag agtagggaac tgccaggcat | 1620 |
| caaataaaac gaaaggctca gtcgaaagac tgggcctttc gtcgacgcgc tagcggagtg | 1680 |
| tatactggct tactatgttg gcactgatga gggtgtcagt gaagtgcttc atgtggcagg | 1740 |
| agaaaaaagg ctgcaccggt gcgtcagcag aatatgtgat acaggatata ttccgcttcc | 1800 |
| tcgctcactg actcgctacg ctcggtcgtt cgactgcggc gagcggaaat ggcttacgaa | 1860 |
| cggggcggag atttcctgga agatgccagg aagatactta acaggaagt gagagggccg | 1920 |
| cggcaaagcc gttttccat aggctccgcc ccctgacaa gcatcacgaa atctgacgct | 1980 |
| caaatcagtg gtggcgaaac ccgacaggac tataaagata ccaggcgttt ccccctggcg | 2040 |
| gctccctcgt gcgctctcct gttcctgcct ttcggtttac cggtgtcatt ccgctgttat | 2100 |
| ggccgcgttt gtctcattcc acgcctgaca ctcagttccg ggtaggcagt tcgctccaag | 2160 |
| ctggactgta tgcacgaacc ccccgttcag tccgaccgct gcgccttatc cggtaactat | 2220 |
| cgtcttgagt ccaacccgga agacatgca aaagcaccac tggcagcagc cactggtaat | 2280 |
| tgatttagag gagttagtct tgaagtcatg cgccggttaa ggctaaactg aaaggacaag | 2340 |
| ttttggtgac tgcgctcctc caagccagtt acctcggttc aaagagttgg tagctcagag | 2400 |
| aaccttcgaa aaaccgccct gcaaggcggt ttttcgttt tcagagcaag agattacgcg | 2460 |
| cagaccaaaa cgatctcaag aagatcatct tattaatcag ataaaatatt tctagatttc | 2520 |
| agtgcaattt atctcttcaa atgtagcacc tgaagtcagc cccatacgat ataagttgtg | 2580 |
| cggccgccct atttgtttat ttttctaaat acattcaaat atgtatccgc tcatgagaca | 2640 |
| ataaccctga taaatgcttc aataatattg aaaaaggaag agtatgagcc atattcaacg | 2700 |

```
ggaaacgtct tgctctaggc cgcgattaaa ttccaacatg gatgctgatt tatatgggta    2760
taaatgggct cgcgataatg tcgggcaatc aggtgcgaca atctatcgat tgtatgggaa    2820
gcccgatgcg ccagagttgt ttctgaaaca tggcaaaggt agcgttgcca atgatgttac    2880
agatgagatg gtcagactaa actggctgac ggaatttatg cctcttccga ccatcaagca    2940
ttttatccgt actcctgatg atgcatggtt actcaccact gcgatccccg ggaaaacagc    3000
attccaggta ttagaagaat atcctgattc aggtgaaaat attgttgatg cgctggcagt    3060
gttcctgcgc cggttgcatt cgattcctgt ttgtaattgt ccttttaaca gcgaccgcgt    3120
atttcgtctc gctcaggcgc aatcacgaat gaataacggt ttggttgatg cgagtgattt    3180
tgatgacgag cgtaatggct ggcctgttga acaagtctgg aaagaaatgc ataaactttt    3240
gccattctca ccggattcag tcgtcactca tggtgatttc tcacttgata accttatttt    3300
tgacgagggg aaattaatag gttgtattga tgttggacga gtcggaatcg cagaccgata    3360
ccaggatctt gccatcctat ggaactgcct cggtgagttt tctccttcat acagaaacg    3420 gcttttcaa aaatatggta ttgataatcc tgatatgaat aaattgcagt tcatttgat    3480 gctcgatgag tttttctaag aattaattca tgagcggata catatttgaa tgtatttaga    3540
aaaataaaca aatagggggtt ccgcgcacat ttccccgaaa agtgccactt gcggagaccc    3600
ggtcgtcagc ttgtcgtcgg ttcagggcag ggtcgttaaa tagcgcatgc                3650
```

<210> SEQ ID NO 36
<211> LENGTH: 3749
<212> TYPE: DNA
<213> ORGANISM: Artificial sequence
<220> FEATURE:
<223> OTHER INFORMATION: synthetic nucleotide

<400> SEQUENCE: 36

```
atgggcagca gccatcacca tcatcaccac agccaggatc cgagcggaac aggacgactg      60
gcaggaaaga ttgcgttaat taccggtggc gccggcaata tcggcagtga attgacacgt     120
cgctttctcg cagagggagc gacggtcatt attagtggac ggaatcgggc gaagttgacc     180
gcactggccg aacggatgca ggcagaggca ggagtgccgg caaagcgcat cgatctcgaa     240
gtcatggatg ggagtgatcc ggtcgcggta cgtgccggta cgaagcgat tgtggcccgt     300 cacggccaga tcgacattct ggtcaacaat gcaggaagtg ccggtgccca gcgtcgtctg     360
gccgagattc cactcactga agctgaatta ggccctggcg ccgaagagac gcttcatgcc     420
agcatcgcca atttacttgg tatgggatgg catctgatgc gtattgcggc acctcatatg     480
ccggtaggaa gtgcggtcat caatgtctcg accatctttt cacgggctga gtactacggg     540
cggattccgt atgtcacccc taaagctgct cttaatgctc tatctcaact tgctgcgcgt     600
gagttaggtg cacgtggcat ccgcgttaat acgatctttc ccggcccgat tgaaagtgat     660
cgcatccgta cagtgttcca gcgtatggat cagctcaagg gcggccccga aggcgacaca     720
gcgcaccatt ttttgaacac catgcgattg tgtcgtgcca acgaccaggg cgcgcttgaa     780
cgtcggttcc cctccgtcgg tgatgtggca gacgccgctg tctttctggc cagtgccgaa     840
tccgccgctc tctccggtga gacgattgag gttacgcacg gaatggagtt gccggcctgc    900
agtgagacca gctgctggcc cgtactgat ctgcgcacga ttgatgccag tggccgcacg     960
acgctcatct gcgccggcga ccagattgaa gaggtgatgg cgctcaccgg tatgttgcgt    1020
acctgtggga gtgaagtgat catcggcttc cgttcggctg cggcgctggc ccagttcgag    1080
```

```
caggcagtca atgagagtcg gcggctggcc ggcgcagact ttacgcctcc cattgccttg    1140
ccactcgatc cacgcgatcc ggcaacaatt gacgctgtct tcgattgggc cggcgagaat    1200
accggcggga ttcatgcagc ggtgattctg cctgctacca gtcacgaacc ggcaccgtgc    1260
gtgattgagg ttgatgatga gcgggtgctg aattttctgg ccgatgaaat caccgggaca    1320
attgtgattg ccagtcgcct ggcccgttac tggcagtcgc aacggcttac ccccggcgca    1380
cgtgcgcgtg ggccgcgtgt cattttctc tcgaacggtg ccgatcaaaa tgggaatgtt    1440
tacggacgca ttcaaagtgc cgctatcggt cagctcattc gtgtgtggcg tcacgaggct    1500
gaacttgact atcagcgtgc cagcgccgcc ggtgatcatg tgctgccgcc ggtatgggcc    1560
aatcagattg tgcgcttcgc taaccgcagc cttgaagggt tagaatttgc ctgtgcctgg    1620
acagctcaat tgctccatag tcaacgccat atcaatgaga ttaccctcaa catccctgcc    1680
aacatttaac aggaggaatt aacatggcag atctccatca ccatcatcac catcacagcg    1740
ccaccaccgg cgcacgcagt gcatcggtcg gatgggcgga aagcctgatc gggttgcatt    1800
tggggaaagt tgccttgatt accggtggca gcgccggtat tggtgggcag atcgggcgcc    1860
tcctggcttt gagtggcgcg cgcgtgatgc tggcagcccg tgatcggcat aagctcgaac    1920
agatgcaggc gatgatccaa tctgagctgg ctgaggtggg gtataccgat gtcgaagatc    1980
gcgtccacat tgcaccgggc tgcgatgtga gtagcgaagc gcagcttgcg gatcttgttg    2040
aacgtaccct gtcagctttt ggcaccgtcg attatctgat caacaacgcc gggatcgccg    2100
gtgtcgaaga gatggttatc gatatgccag ttgagggatg cgccatacc ctcttcgcca    2160 atctgatcag caactactcg ttgatgcgca aactggcgcc gttgatgaaa aacagggta    2220 gcggttacat ccttaacgtc tcatcatact ttggcggtga aaaagatgcg gccattccct    2280
accccaaccg tgccgattac gccgtctcga aggctggtca gcgggcaatg gccgaagtct    2340
ttgcgcgctt ccttggcccg gagatacaga tcaatgccat tgcgccgggt ccggtcgaag    2400
gtgatcgctt gcgcggtacc ggtgaacgtc ccggcctctt tgcccgtcgg gcgcggctga    2460
ttttggagaa caagcggctg aatgagcttc acgctgctct tatcgcggct gcgcgcaccg    2520
atgagcgatc tatgcacgaa ctggttgaac tgctcttacc caatgatgtg gccgcactag    2580
agcagaatcc cgcagcacct accgcgttgc gtgaactggc acgacgtttt cgcagcgaag    2640
gcgatccggc ggcatcatca agcagtgcgc tgctgaaccg ttcaattgcc gctaaattgc    2700
tggctcgttt gcataatggt ggctatgtgt tgcctgccga catctttgca aacctgccaa    2760
acccgcccga tcccttcttc acccgagccc agattgatcg cgaggctcgc aaggttcgtg    2820
acggcatcat ggggatgctc tacctgcaac ggatgccgac tgagtttgat gtcgcaatgg    2880
ccaccgtcta ttaccttgcc gaccgcgtgg tcagtggtga acattccac ccatcaggtg    2940 gtttgcgtta cgaacgcacc cctaccggtg gcgaactctt cggcttgccc tcaccggaac    3000
ggctggcgga gctggtcgga agcacggtct atctgatagg tgaacatctg actgaacacc    3060
ttaacctgct tgcccgtgcg tacctcgaac gttacgggc acgtcaggta gtgatgattg    3120
ttgagacaga aaccggggca gagacaatgc gtcgcttgct ccacgatcac gtcgaggctg    3180
gtcggctgat gactattgtg ccggtgatc agatcgaagc cgctatcgac caggctatca    3240
ctcgctacgg tcgcccaggg ccggtcgtct gtaccccctt ccggccactg ccgacggtac    3300
cactggtcgg gcgtaaagac agtgactgga gcacagtgtt gagtgaggct gaatttgccg    3360
agttgtgcga acaccagctc acccaccatt tccgggtagc gcgctggatt gccctgagtg    3420
atggtgcccg tctcgcgctg gtcactcccg aaactacggc tacctcaact accgagcaat    3480
```

```
ttgctctggc taacttcatc aaaacgaccc ttcacgcttt tacggctacg attggtgtcg    3540
agagcgaaag aactgctcag cgcattctga tcaatcaagt cgatctgacc cggcgtgcgc    3600
gtgccgaaga gccgcgtgat ccgcacgagc gtcaacaaga actggaacgt tttatcgagg    3660
cagtcttgct ggtcactgca ccactcccgc ctgaagccga tacccgttac gccgggcgga    3720
ttcatcgcgg acgggcgatt accgtgtaa                                      3749
```

<210> SEQ ID NO 37
<211> LENGTH: 1243
<212> TYPE: PRT
<213> ORGANISM: Artificial sequence
<220> FEATURE:
<223> OTHER INFORMATION: synthetic peptide

<400> SEQUENCE: 37

```
Met Gly Ser Ser His His His His Ser Gln Asp Pro Ser Gly
1               5                   10                  15

Thr Gly Arg Leu Ala Gly Lys Ile Ala Leu Ile Thr Gly Gly Ala Gly
            20                  25                  30

Asn Ile Gly Ser Glu Leu Thr Arg Arg Phe Leu Ala Glu Gly Ala Thr
        35                  40                  45

Val Ile Ile Ser Gly Arg Asn Arg Ala Lys Leu Thr Ala Leu Ala Glu
    50                  55                  60

Arg Met Gln Ala Glu Ala Gly Val Pro Ala Lys Arg Ile Asp Leu Glu
65                  70                  75                  80

Val Met Asp Gly Ser Asp Pro Val Ala Val Arg Ala Gly Ile Glu Ala
                85                  90                  95

Ile Val Ala Arg His Gly Gln Ile Asp Ile Leu Val Asn Asn Ala Gly
            100                 105                 110

Ser Ala Gly Ala Gln Arg Arg Leu Ala Glu Ile Pro Leu Thr Glu Ala
        115                 120                 125

Glu Leu Gly Pro Gly Ala Glu Glu Thr Leu His Ala Ser Ile Ala Asn
    130                 135                 140

Leu Leu Gly Met Gly Trp His Leu Met Arg Ile Ala Ala Pro His Met
145                 150                 155                 160

Pro Val Gly Ser Ala Val Ile Asn Val Ser Thr Ile Phe Ser Arg Ala
                165                 170                 175

Glu Tyr Tyr Gly Arg Ile Pro Tyr Val Thr Pro Lys Ala Ala Leu Asn
            180                 185                 190

Ala Leu Ser Gln Leu Ala Ala Arg Glu Leu Gly Ala Arg Gly Ile Arg
        195                 200                 205

Val Asn Thr Ile Phe Pro Gly Pro Ile Glu Ser Asp Arg Ile Arg Thr
    210                 215                 220

Val Phe Gln Arg Met Asp Gln Leu Lys Gly Arg Pro Glu Gly Asp Thr
225                 230                 235                 240

Ala His His Phe Leu Asn Thr Met Arg Leu Cys Arg Ala Asn Asp Gln
                245                 250                 255

Gly Ala Leu Glu Arg Arg Phe Pro Ser Val Gly Asp Val Ala Asp Ala
            260                 265                 270

Ala Val Phe Leu Ala Ser Ala Glu Ser Ala Ala Leu Ser Gly Glu Thr
        275                 280                 285

Ile Glu Val Thr His Gly Met Glu Leu Pro Ala Cys Ser Glu Thr Ser
    290                 295                 300

Leu Leu Ala Arg Thr Asp Leu Arg Thr Ile Asp Ala Ser Gly Arg Thr
```

```
            305                 310                 315                 320
        Thr Leu Ile Cys Ala Gly Asp Gln Ile Glu Glu Val Met Ala Leu Thr
                        325                 330                 335
        Gly Met Leu Arg Thr Cys Gly Ser Glu Val Ile Ile Gly Phe Arg Ser
                        340                 345                 350
        Ala Ala Ala Leu Ala Gln Phe Glu Gln Ala Val Asn Glu Ser Arg Arg
                        355                 360                 365
        Leu Ala Gly Ala Asp Phe Thr Pro Pro Ile Ala Leu Pro Leu Asp Pro
        370                 375                 380
        Arg Asp Pro Ala Thr Ile Asp Ala Val Phe Asp Trp Ala Gly Glu Asn
        385                 390                 395                 400
        Thr Gly Gly Ile His Ala Ala Val Ile Leu Pro Ala Thr Ser His Glu
                        405                 410                 415
        Pro Ala Pro Cys Val Ile Glu Val Asp Asp Glu Arg Val Leu Asn Phe
                        420                 425                 430
        Leu Ala Asp Glu Ile Thr Gly Thr Ile Val Ile Ala Ser Arg Leu Ala
                        435                 440                 445
        Arg Tyr Trp Gln Ser Gln Arg Leu Thr Pro Gly Ala Arg Ala Arg Gly
                        450                 455                 460
        Pro Arg Val Ile Phe Leu Ser Asn Gly Ala Asp Gln Asn Gly Asn Val
        465                 470                 475                 480
        Tyr Gly Arg Ile Gln Ser Ala Ala Ile Gly Gln Leu Ile Arg Val Trp
                        485                 490                 495
        Arg His Glu Ala Glu Leu Asp Tyr Gln Arg Ala Ser Ala Ala Gly Asp
                        500                 505                 510
        His Val Leu Pro Pro Val Trp Ala Asn Gln Ile Val Arg Phe Ala Asn
                        515                 520                 525
        Arg Ser Leu Glu Gly Leu Glu Phe Ala Cys Ala Trp Thr Ala Gln Leu
                        530                 535                 540
        Leu His Ser Gln Arg His Ile Asn Glu Ile Thr Leu Asn Ile Pro Ala
        545                 550                 555                 560
        Asn Ile Met Ala Asp Leu His His His His His His Ser Ala Thr
                        565                 570                 575
        Thr Gly Ala Arg Ser Ala Ser Val Gly Trp Ala Glu Ser Leu Ile Gly
                        580                 585                 590
        Leu His Leu Gly Lys Val Ala Leu Ile Thr Gly Gly Ser Ala Gly Ile
                        595                 600                 605
        Gly Gly Gln Ile Gly Arg Leu Leu Ala Leu Ser Gly Ala Arg Val Met
                        610                 615                 620
        Leu Ala Ala Arg Asp Arg His Lys Leu Glu Gln Met Gln Ala Met Ile
        625                 630                 635                 640
        Gln Ser Glu Leu Ala Glu Val Gly Tyr Thr Asp Val Glu Asp Arg Val
                        645                 650                 655
        His Ile Ala Pro Gly Cys Asp Val Ser Ser Glu Ala Gln Leu Ala Asp
                        660                 665                 670
        Leu Val Glu Arg Thr Leu Ser Ala Phe Gly Thr Val Asp Tyr Leu Ile
                        675                 680                 685
        Asn Asn Ala Gly Ile Ala Gly Val Glu Glu Met Val Ile Asp Met Pro
        690                 695                 700
        Val Glu Gly Trp Arg His Thr Leu Phe Ala Asn Leu Ile Ser Asn Tyr
        705                 710                 715                 720
        Ser Leu Met Arg Lys Leu Ala Pro Leu Met Lys Lys Gln Gly Ser Gly
                        725                 730                 735
```

```
Tyr Ile Leu Asn Val Ser Ser Tyr Phe Gly Gly Glu Lys Asp Ala Ala
                740                 745                 750

Ile Pro Tyr Pro Asn Arg Ala Asp Tyr Ala Val Ser Lys Ala Gly Gln
        755                 760                 765

Arg Ala Met Ala Glu Val Phe Ala Arg Phe Leu Gly Pro Glu Ile Gln
770                 775                 780

Ile Asn Ala Ile Ala Pro Gly Pro Val Glu Gly Asp Arg Leu Arg Gly
785                 790                 795                 800

Thr Gly Glu Arg Pro Gly Leu Phe Ala Arg Ala Arg Leu Ile Leu
                805                 810                 815

Glu Asn Lys Arg Leu Asn Glu Leu His Ala Ala Leu Ile Ala Ala Ala
                820                 825                 830

Arg Thr Asp Glu Arg Ser Met His Glu Leu Val Glu Leu Leu Leu Pro
                835                 840                 845

Asn Asp Val Ala Ala Leu Glu Gln Asn Pro Ala Ala Pro Thr Ala Leu
                850                 855                 860

Arg Glu Leu Ala Arg Arg Phe Arg Ser Glu Gly Asp Pro Ala Ala Ser
865                 870                 875                 880

Ser Ser Ser Ala Leu Leu Asn Arg Ser Ile Ala Ala Lys Leu Leu Ala
                885                 890                 895

Arg Leu His Asn Gly Gly Tyr Val Leu Pro Ala Asp Ile Phe Ala Asn
                900                 905                 910

Leu Pro Asn Pro Pro Asp Pro Phe Phe Thr Arg Ala Gln Ile Asp Arg
                915                 920                 925

Glu Ala Arg Lys Val Arg Asp Gly Ile Met Gly Met Leu Tyr Leu Gln
                930                 935                 940

Arg Met Pro Thr Glu Phe Asp Val Ala Met Ala Thr Val Tyr Tyr Leu
945                 950                 955                 960

Ala Asp Arg Val Val Ser Gly Glu Thr Phe His Pro Ser Gly Gly Leu
                965                 970                 975

Arg Tyr Glu Arg Thr Pro Thr Gly Gly Glu Leu Phe Gly Leu Pro Ser
                980                 985                 990

Pro Glu Arg Leu Ala Glu Leu Val Gly Ser Thr Val Tyr Leu Ile Gly
                995                 1000                1005

Glu His Leu Thr Glu His Leu Asn Leu Leu Ala Arg Ala Tyr Leu
    1010                1015                1020

Glu Arg Tyr Gly Ala Arg Gln Val Val Met Ile Val Glu Thr Glu
    1025                1030                1035

Thr Gly Ala Glu Thr Met Arg Arg Leu Leu His Asp His Val Glu
    1040                1045                1050

Ala Gly Arg Leu Met Thr Ile Val Ala Gly Asp Gln Ile Glu Ala
    1055                1060                1065

Ala Ile Asp Gln Ala Ile Thr Arg Tyr Gly Arg Pro Gly Pro Val
    1070                1075                1080

Val Cys Thr Pro Phe Arg Pro Leu Pro Thr Val Pro Leu Val Gly
    1085                1090                1095

Arg Lys Asp Ser Asp Trp Ser Thr Val Leu Ser Glu Ala Glu Phe
    1100                1105                1110

Ala Glu Leu Cys Glu His Gln Leu Thr His His Phe Arg Val Ala
    1115                1120                1125

Arg Trp Ile Ala Leu Ser Asp Gly Ala Arg Leu Ala Leu Val Thr
    1130                1135                1140
```

| | | | | | | | | | | | |
|---|---|---|---|---|---|---|---|---|---|---|---|
|Pro|Glu|Thr|Thr|Ala|Thr|Ser|Thr|Thr|Glu|Gln|Phe|Ala|Leu|Ala|
| |1145| | | | |1150| | | | |1155| | | |

| | | | | | | | | | | | |
|---|---|---|---|---|---|---|---|---|---|---|---|
|Asn|Phe|Ile|Lys|Thr|Thr|Leu|His|Ala|Phe|Thr|Ala|Thr|Ile|Gly|
| |1160| | | | |1165| | | | |1170| | | |

| | | | | | | | | | | | |
|---|---|---|---|---|---|---|---|---|---|---|---|
|Val|Glu|Ser|Glu|Arg|Thr|Ala|Gln|Arg|Ile|Leu|Ile|Asn|Gln|Val|
| |1175| | | | |1180| | | | |1185| | | |

| | | | | | | | | | | | |
|---|---|---|---|---|---|---|---|---|---|---|---|
|Asp|Leu|Thr|Arg|Arg|Ala|Arg|Ala|Glu|Glu|Pro|Arg|Asp|Pro|His|
| |1190| | | | |1195| | | | |1200| | | |

| | | | | | | | | | | | |
|---|---|---|---|---|---|---|---|---|---|---|---|
|Glu|Arg|Gln|Gln|Glu|Leu|Glu|Arg|Phe|Ile|Glu|Ala|Val|Leu|Leu|
| |1205| | | | |1210| | | | |1215| | | |

| | | | | | | | | | | | |
|---|---|---|---|---|---|---|---|---|---|---|---|
|Val|Thr|Ala|Pro|Leu|Pro|Pro|Glu|Ala|Asp|Thr|Arg|Tyr|Ala|Gly|
| |1220| | | | |1225| | | | |1230| | | |

| | | | | | | | |
|---|---|---|---|---|---|---|---|
|Arg|Ile|His|Arg|Gly|Arg|Ala|Ile|Thr|Val|
| |1235| | | | |1240| | | |

<210> SEQ ID NO 38
<211> LENGTH: 825
<212> TYPE: DNA
<213> ORGANISM: Artificial sequence
<220> FEATURE:
<223> OTHER INFORMATION: synthetic nucleotide

<400> SEQUENCE: 38

```
atggtcgcac ccattccgc gaaacgcggc agaaaacccg ccgttgccac cgcaccagcg      60
actggacagg ttcagtcttt aacgcgtggc ctgaaattac tggagtggat tgccgaatcc    120
aatggcagtg tggcactcac ggaactggcg caacaagccg ggttacccaa ttccacgacc    180
caccgcctgc taaccacgat gcaacagcag ggtttcgtgc gtcaggttgg cgaactggga    240
cattgggcaa tcggcgcaca tgcctttatg gtcggcagca gctttctcca gagccgtaat    300
tgttagcga ttgttcaccc tatcctgcgc aatctaatgg aagagtctgg cgaaacggtc    360
aatatggcgg tgcttgatca aagcgatcac gaagcgatta ttatcgacca ggtacagtgt    420
acgcatctga tgcgaatgtc cgcgcctatc ggcggtaaat tgccgatgca cgcttccggt    480
gcgggtaaag cctttttagc ccaactgagc gaagaacagg tgacgaagct gctgcaccgc    540
aaagggttac atgcctatac ccacgcaacg ctggtgtctc ctgtgcattt aaaagaagat    600
ctcgcccaaa cgcgcaaacg gggttattca tttgacgatg aggaacatgc actgggcta    660
cgttgccttg cagcgtgtat tttcgatgag caccgtgaac cgtttgccgc aatttctatt    720
tccggaccga tttcacgtat taccgatgac cgcgtgaccg agtttggcgc gatggtgatt    780
aaagcggcga aggaagtgac gctggcgtac ggtggaatgc gctga                    825
```

<210> SEQ ID NO 39
<211> LENGTH: 274
<212> TYPE: PRT
<213> ORGANISM: Artificial sequence
<220> FEATURE:
<223> OTHER INFORMATION: synthetic peptide

<400> SEQUENCE: 39

| | | | | | | | | | | | |
|---|---|---|---|---|---|---|---|---|---|---|---|
|Met|Val|Ala|Pro|Ile|Pro|Ala|Lys|Arg|Gly|Arg|Lys|Pro|Ala|Val|Ala|
|1| | | |5| | | | |10| | | | |15| |

| | | | | | | | | | | | |
|---|---|---|---|---|---|---|---|---|---|---|---|
|Thr|Ala|Pro|Ala|Thr|Gly|Gln|Val|Gln|Ser|Leu|Thr|Arg|Gly|Leu|Lys|
| | | | |20| | | | |25| | | | |30| |

| | | | | | | | | | | | |
|---|---|---|---|---|---|---|---|---|---|---|---|
|Leu|Leu|Glu|Trp|Ile|Ala|Glu|Ser|Asn|Gly|Ser|Val|Ala|Leu|Thr|Glu|
| | | | |35| | | | |40| | | | |45| |

| | | | | | | | |
|---|---|---|---|---|---|---|---|
|Leu|Ala|Gln|Gln|Ala|Gly|Leu|Pro|Asn|Ser|Thr|Thr|His|Arg|Leu|Leu|

```
                    50                    55                    60
Thr Thr Met Gln Gln Gln Gly Phe Val Arg Gln Val Gly Glu Leu Gly
 65                  70                  75                  80

His Trp Ala Ile Gly Ala His Ala Phe Met Val Gly Ser Ser Phe Leu
                     85                  90                  95

Gln Ser Arg Asn Leu Leu Ala Ile Val His Pro Ile Leu Arg Asn Leu
                100                 105                 110

Met Glu Glu Ser Gly Glu Thr Val Asn Met Ala Val Leu Asp Gln Ser
                115                 120                 125

Asp His Glu Ala Ile Ile Ile Asp Gln Val Gln Cys Thr His Leu Met
                130                 135                 140

Arg Met Ser Ala Pro Ile Gly Gly Lys Leu Pro Met His Ala Ser Gly
145                 150                 155                 160

Ala Gly Lys Ala Phe Leu Ala Gln Leu Ser Glu Glu Val Thr Lys
                    165                 170                 175

Leu Leu His Arg Lys Gly Leu His Ala Tyr Thr His Ala Thr Leu Val
                180                 185                 190

Ser Pro Val His Leu Lys Glu Asp Leu Ala Gln Thr Arg Lys Arg Gly
                195                 200                 205

Tyr Ser Phe Asp Asp Glu Glu His Ala Leu Gly Leu Arg Cys Leu Ala
                210                 215                 220

Ala Cys Ile Phe Asp Glu His Arg Glu Pro Phe Ala Ala Ile Ser Ile
225                 230                 235                 240

Ser Gly Pro Ile Ser Arg Ile Thr Asp Asp Arg Val Thr Glu Phe Gly
                    245                 250                 255

Ala Met Val Ile Lys Ala Ala Lys Glu Val Thr Leu Ala Tyr Gly Gly
                260                 265                 270

Met Arg
```

<210> SEQ ID NO 40
<211> LENGTH: 2802
<212> TYPE: DNA
<213> ORGANISM: Artificial sequence
<220> FEATURE:
<223> OTHER INFORMATION: synthetic nucleotide

<400> SEQUENCE: 40

```
atgcagaaca gcgctttgaa agcctggttg gactcttctt acctctctgg cgcaaaccag    60
agctggatag aacagctcta tgaagacttc ttaaccgatc ctgactcggt tgacgctaac   120
tggcgttcga cgttccagca gttacctggt acgggagtca aaccggatca attccactct   180
caaacgcgtg aatatttccg ccgcctggcg aaagacgctt cacgttactc ttcaacgatc   240
tccgaccctg acaccaatgt gaagcaggtt aaagtcctgc agctcattaa cgcataccgc   300
ttccgtggtc accagcatgc gaatctcgat ccgctgggac tgtggcagca agataaagtg   360
gccgatctgg atccgtcttt ccacgatctg accgaagcag acttccagga gaccttcaac   420
gtcggttcat tgccagcggg caaagaaacc atgaaactcg gcgagctgct ggaagccctc   480
aagcaaacct actgcggccc gattggtgcc gagtatatgc acattaccag caccgaagaa   540
aaacgctgga tccaacagcg tatcgagtct ggtcgcgcga ctttcaatag cgaagagaaa   600
aaacgcttct taagcgaact gaccgccgct gaaggtcttg aacgttacct cggcgcaaaa   660
ttccctggcg caaaacgctt ctcgctggaa ggcggtgacg cgttaatccc gatgcttaaa   720
gagatgatcc gccacgctgg caacagcggc acccgcgaag tggttctcgg gatggcgcac   780
```

```
cgtggtcgtc tgaacgtgct ggtgaacgtg ctgggtaaaa aaccgcaaga cttgttcgac    840
gagttcgccg gtaaacataa agaacacctc ggcacgggtg acgtgaaata ccacatgggc    900
ttctcgtctg acttccagac cgatggcggc ctggtgcacc tggcgctggc gtttaacccg    960
tctcaccttg agattgtaag cccggtagtt atcggttctg ttcgtgcccg tctggacaga   1020
cttgatgagc cgagcagcaa caaagtgctg ccaatcacca tccacggtga cgccgcagtg   1080
accgggcagg gcgtggttca ggaaaccctg aacatgtcga agcgcgtgg ttatgaagtt    1140
ggcggtacgg tacgtatcgt tatcaacaac caggttggtt tcaccacctc taatccgctg   1200
gatgcccgtt ctacgccgta ctgtactgat atcggtaaga tggttcaggc cccgattttc   1260
cacgttaacg cggacgatcc ggaagccgtt gcctttgtga cccgtctggc gctcgatttc   1320
cgtaacacct ttaaacgtga tgtcttcatc gacctggtgt gctaccgccg tcacggccac   1380
aacgaagccg acgagccgag cgcaacccag ccgctgatgt atcagaaaat caaaaaacat   1440
ccgacaccgc gcaaaatcta cgctgacaag ctggagcagg aaaaagtggc gacgctggaa   1500
gatgccaccg agatggttaa cctgtaccgc gatgcgctgg atgctggcga ttgcgtagtg   1560
gcagagtggc gtccgatgaa catgcactct ttcacctggt cgccgtacct caaccacgaa   1620
tgggacgaag agtacccgaa caaagttgag atgaagcgcc tgcaggagct ggcgaaacgc   1680
atcagcacgg tgccggaagc agttgaaatg cagtctcgcg ttgccaagat ttatggcgat   1740
cgccaggcga tggctgccgg tgagaaactg ttcgactggg gcggtgcgga aaacctcgct   1800
tacgccacgc tggttgatga aggcattccg gttcgcctgt cgggtgaaga ctccggtcgc   1860
ggtaccttct ccaccgcca cgcggtgatc cacaaccagt ctaacggttc cacttacacg   1920
ccgctgcaac atatccataa cgggcagggc gcgttccgtg tctgggactc cgtactgtct   1980
gaagaagcag tgctggcgtt tgaatatggt tatgccaccg cagaaccacg cactctgacc   2040
atctgggaag cgcagttcgg tgacttcgcc aacggtgcgc aggtggttat cgaccagttc   2100
atctcctctg cgaacagaa atggggccgg atgtgtggtc tggtgatgtt gctgccgcac   2160
ggttacgaag ggcaggggcc ggagcactcc tccgcgcgtc tggaacgtta tctgcaactt   2220
tgtgctgagc aaaacatgca ggtttgcgta ccgtctaccc cggcacaggt ttaccacatg   2280
ctgcgtcgtc aggcgctgcg cgggatgcgt cgtccgctgg tcgtgatgtc gccgaaatcc   2340
ctgctgcgtc atccgctggc ggtttccagc ctcgaagaac tggcgaacgg caccttcctg   2400
ccagccatcg gtgaaatcga cgagcttgat ccgaagggcg tgaagcgcgt agtgatgtgt   2460
tctggtaagg tttattacga cctgctggaa cagcgtcgta agaacaatca acacgatgtc   2520
gccattgtgc gtatcgagca actctacccg ttcccgcata agcgatgca ggaagtgttg    2580
cagcagtttg ctcacgtcaa ggattttgtc tggtgccagg aagagccgct caaccagggc   2640
gcatggtact gcagccagca tcatttccgt gaagtgattc cgtttggggc ttctctgcgt   2700
tatgcaggcc gcccggcctc cgcctctccg gcggtagggt atatgtccgt tcaccagaaa   2760
cagcaacaag atctggttaa tgacgcgctg aacgtcgaat aa                      2802
```

<210> SEQ ID NO 41
<211> LENGTH: 933
<212> TYPE: PRT
<213> ORGANISM: Artificial sequence
<220> FEATURE:
<223> OTHER INFORMATION: synthetic peptide

<400> SEQUENCE: 41

Met Gln Asn Ser Ala Leu Lys Ala Trp Leu Asp Ser Ser Tyr Leu Ser

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   |   | 10 |   |   |   |   | 15 |

Gly Ala Asn Gln Ser Trp Ile Glu Gln Leu Tyr Glu Asp Phe Leu Thr
                    20                  25                  30

Asp Pro Asp Ser Val Asp Ala Asn Trp Arg Ser Thr Phe Gln Gln Leu
                35                  40                  45

Pro Gly Thr Gly Val Lys Pro Asp Gln Phe His Ser Gln Thr Arg Glu
            50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                    85                  90                  95

Asn Ala Tyr Arg Phe Arg Gly His Gln His Ala Asn Leu Asp Pro Leu
                100                 105                 110

Gly Leu Trp Gln Gln Asp Lys Val Ala Asp Leu Asp Pro Ser Phe His
            115                 120                 125

Asp Leu Thr Glu Ala Asp Phe Gln Glu Thr Phe Asn Val Gly Ser Phe
        130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
                180                 185                 190

Ala Thr Phe Asn Ser Glu Glu Lys Lys Arg Phe Leu Ser Glu Leu Thr
            195                 200                 205

Ala Ala Glu Gly Leu Glu Arg Tyr Leu Gly Ala Lys Phe Pro Gly Ala
        210                 215                 220

Lys Arg Phe Ser Leu Glu Gly Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
            260                 265                 270

Lys Lys Pro Gln Asp Leu Phe Asp Glu Phe Ala Gly Lys His Lys Glu
        275                 280                 285

His Leu Gly Thr Gly Asp Val Lys Tyr His Met Gly Phe Ser Ser Asp
        290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
        370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430

```
Val Thr Arg Leu Ala Leu Asp Phe Arg Asn Thr Phe Lys Arg Asp Val
        435                 440                 445

Phe Ile Asp Leu Val Cys Tyr Arg Arg His Gly His Asn Glu Ala Asp
450                 455                 460

Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510

Leu Asp Ala Gly Asp Cys Val Val Ala Glu Trp Arg Pro Met Asn Met
        515                 520                 525

His Ser Phe Thr Trp Ser Pro Tyr Leu Asn His Glu Trp Asp Glu Glu
    530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
        595                 600                 605

Ile Pro Val Arg Leu Ser Gly Glu Asp Ser Gly Arg Gly Thr Phe Phe
    610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
        755                 760                 765

Met Arg Arg Pro Leu Val Val Met Ser Pro Lys Ser Leu Leu Arg His
    770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
        835                 840                 845
```

```
Tyr Pro Phe Pro His Lys Ala Met Gln Glu Val Leu Gln Gln Phe Ala
    850                 855                 860
His Val Lys Asp Phe Val Trp Cys Gln Glu Pro Leu Asn Gln Gly
865                 870                 875                 880
Ala Trp Tyr Cys Ser Gln His His Phe Arg Glu Val Ile Pro Phe Gly
                885                 890                 895
Ala Ser Leu Arg Tyr Ala Gly Arg Pro Ala Ser Ala Ser Pro Ala Val
                900                 905                 910
Gly Tyr Met Ser Val His Gln Lys Gln Gln Gln Asp Leu Val Asn Asp
        915                 920                 925
Ala Leu Asn Val Glu
    930
```

<210> SEQ ID NO 42
<211> LENGTH: 1722
<212> TYPE: DNA
<213> ORGANISM: Artificial sequence
<220> FEATURE:
<223> OTHER INFORMATION: synthetic nucleotide

<400> SEQUENCE: 42

| | |
|---|---:|
| cgttaagcga ttcagcacct tacctcaggc accttcgggt gccttttta gtctcgagaa | 60 |
| tatcctcctt ataacttcgt ataatgtatg ctatacgaac ggtaagagcg cttttgaagc | 120 |
| tggggtgggc gaagaactcc agcatgagat ccccgcgctg gaggatcatc cagccggcgt | 180 |
| cccggaaaac gattccgaag cccaaccttt catagaaggc ggcggtggaa tcgaaatctc | 240 |
| gtgatggcag gttgggcgtc gcttggtcgg tcatttggaa ccccagagtc ccgctcagaa | 300 |
| gaactcgtca agaaggcgat agaaggcgat gcgctgcgaa tcgggagcgg cgataccgta | 360 |
| aagcacgagg aagcggtcag cccattcgcc gccaagctct tcagcaatat cacgggtagc | 420 |
| caacgctatg tcctgatagc ggtccgccac acccagccgg ccacagtcga tgaatccaga | 480 |
| aaagcggcca ttttccacca tgatattcgg caagcaggca tcgccatggg tcacgacgag | 540 |
| atcctcgccg tcgggcatgc gcgccttgag cctggcgaac agttcggctg cgcgagccc | 600 |
| ctgatgctct tcgtccagat catcctgatc gacaagaccg gcttccatcc gagtacgtgc | 660 |
| tcgctcgatg cgatgtttcg cttggtggtc gaatgggcag gtagccggat caagcgtatg | 720 |
| cagccgccgc attgcatcag ccatgatgga ctttctcg gcaggagcaa ggtgagatga | 780 |
| caggagatcc tgccccggca cttcgcccaa tagcagccag tcccttcccg cttcagtgac | 840 |
| aacgtcgagc acagctgcgc aaggaacgcc cgtcgtggcc agccacgata gccgcgctgc | 900 |
| ctcgtcctgc agttcattca gggcaccgga caggtcggtc ttgacaaaaa gaaccgggcg | 960 |
| cccctgcgct gacagccgga acacggcggc atcagagcag ccgattgtct gttgtgccca | 1020 |
| gtcatagccg aatagcctct ccacccaagc ggccggagaa cctgcgtgca atccatcttg | 1080 |
| ttcaatcatg cgaaacgatc ctcatcctgt ctcttgatca gatcttgatc ccctgcgcca | 1140 |
| tcagatcctt ggcggcaaga aagccatcca gtttactttg cagggcttcc caaccttacc | 1200 |
| agagggcgcc ccagctggca attccggttc gcttgctgtc cataaaaccg cccagtctag | 1260 |
| ctatcgccat gtaagcccac tgcaagctac ctgctttctc tttgcgcttg cgttttccct | 1320 |
| tgtccagata gcccagtagc tgacattcat ccggggtcag caccgtttct gcggactggc | 1380 |
| tttctacgtg ttccgcttcc tttagcagcc cttgcgccct gagtgcttgc ggcagcgtga | 1440 |
| ggggatcttt accgttcgta taatgtatgc tataccaagt tatgaagcta gcttatcaaa | 1500 |
| aagagtattg acataaagtc taacctatag ataattacag ccatcgagag ggacacggcg | 1560 |

```
atttgctgtc accggatgtg ctttccggtc tgatgagtcc gtgaggacga aacagcctct    1620
acaaataatt ttgtttaaga attcaaaaga tcttttaaga aggagatata ccatgactga    1680
acaggcaaca caaccgatg aactggcttt cacaaggccg ta                        1722
```

<210> SEQ ID NO 43
<211> LENGTH: 1602
<212> TYPE: DNA
<213> ORGANISM: Artificial sequence
<220> FEATURE:
<223> OTHER INFORMATION: synthetic nucleotide

<400> SEQUENCE: 43

```
atgactgaac aggcaacaac aaccgatgaa ctggctttca aaggccgta tggcgagcag      60 gagaagcaaa ttcttactgc cgaagcggta gaatttctga ctgagctggt gacgcatttt    120
acgccacaac gcaataaact tctggcagcg cgcattcagc agcagcaaga tattgataac    180
ggaacgttgc ctgattttat ttcggaaaca gcttccattc gcgatgctga ttggaaaatt    240
cgcgggattc ctgcggactt agaagaccgc cgcgtagaga taactggccc ggtagagcgc    300
aagatggtga tcaacgcgct caacgccaat gtgaaagtct ttatggccga tttcgaagat    360
tcactggcac cagactggaa caaagtgatc gacgggcaaa ttaacctgcg tgatgcggtt    420
aacggcacca tcagttacac caatgaagca ggcaaaattt accagctcaa gcccaatcca    480
gcggttttga tttgtcgggt acgcggtctg cacttgccgg aaaaacatgt cacctggcgt    540
ggtgaggcaa tccccggcag cctgtttgat tttgcgctct atttcttcca caactatcag    600
gcactgttgg caaagggcag tggtccctat ttctatctgc gaaaacccca gtcctggcag    660
gaagcggcct ggtggagcga agtcttcagc tatgcagaag atcgctttaa tctgccgcgc    720
ggcaccatca aggcgacgtt gctgattgaa acgctgcccg ccgtgttcca gatggatgaa    780
atccttcacg cgctgcgtga ccatattgtt ggtctgaact gcggtcgttg ggattacatc    840
ttcagctata tcaaaacgtt gaaaaactat cccgatcgcg tcctgccaga cagacaggca    900
gtgacgatgg ataaaccatt cctgaatgct tactcacgcc tgttgattaa aacctgccat    960
aaacgcggtg cttttgcgat gggcggcatg gcggcgttta ttccgagcaa agatgaagag   1020
cacaataacc aggtgctcaa caaagtaaaa gcggataaat cgctggaagc caataacggt   1080
cacgatggca catggatcgc tcacccaggc cttgcggaca cggcaatggc ggtattcaac   1140
gacattctcg ctcccgtaa aaatcagctt gaagtgatgc gcgaacaaga cgcgccgatt   1200
actgccgatc agctgctggc accttgtgat ggtgaacgca ccgaagaagg tatgcgcgcc   1260
aacattcgcg tggctgtgca gtacatcgaa gcgtggatct ctggcaacgg ctgtgtgccg   1320
atttatggcc tgatggaaga tgcggcgacg gctgaaattt cccgtacctc gatctggcag   1380
tggatccatc atcaaaaaac gttgagcaat ggcaaaccgg tgaccaaagc cttgttccgc   1440
cagatgctgg cgaagagat gaaagtcatt gccagcgaac tgggcgaaga acgtttctcc   1500
caggggcgtt ttgacgatgc cgcacgcttg atggaacaga tcaccacttc cgatgagtta   1560
attgatttcc tgaccctgcc aggctaccgc ctgttagcgt aa                       1602
```

<210> SEQ ID NO 44
<211> LENGTH: 533
<212> TYPE: PRT
<213> ORGANISM: Artificial sequence
<220> FEATURE:
<223> OTHER INFORMATION: synthetic peptide

<400> SEQUENCE: 44

```
Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
                20                  25                  30

Leu Thr Glu Leu Val Thr His Phe Thr Pro Gln Arg Asn Lys Leu Leu
            35                  40                  45

Ala Ala Arg Ile Gln Gln Gln Asp Ile Asp Asn Gly Thr Leu Pro
        50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Val Glu Ile Thr Gly
                85                  90                  95

Pro Val Glu Arg Lys Met Val Ile Asn Ala Leu Asn Ala Asn Val Lys
                100                 105                 110

Val Phe Met Ala Asp Phe Glu Asp Ser Leu Ala Pro Asp Trp Asn Lys
            115                 120                 125

Val Ile Asp Gly Gln Ile Asn Leu Arg Asp Ala Val Asn Gly Thr Ile
130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415
```

```
Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
            435                 440                 445

Ala Thr Ala Glu Ile Ser Arg Thr Ser Ile Trp Gln Trp Ile His His
        450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
        530
```

<210> SEQ ID NO 45
<211> LENGTH: 1305
<212> TYPE: DNA
<213> ORGANISM: Artificial sequence
<220> FEATURE:
<223> OTHER INFORMATION: synthetic nucleotide

<400> SEQUENCE: 45

| | | |
|---|---|---|
| atgaaaaccc gtacacaaca aattgaagaa ttacagaaag agtggactca accgcgttgg | 60 |
| gaaggcatta ctcgcccata cagtgcggaa gatgtggtga aattacgcgg ttcagtcaat | 120 |
| cctgaatgca cgctggcgca actgggcgca gcgaaaatgt ggcgtctgct gcacggtgag | 180 |
| tcgaaaaaag gctacatcaa cagcctcggc gcactgactg gcgtcaggc gctgcaacag | 240 |
| gcgaaagcgg gtattgaagc agtctatctg tcgggatggc aggtagcggc ggacgctaac | 300 |
| ctggcggcca gcatgtatcc ggatcagtcg ctctatccgg caaactcggt gccagctgtg | 360 |
| gtggagcgga tcaacaacac cttccgtcgt gccgatcaga tccaatggtc gcgcggcatt | 420 |
| gagccgggcg atccgcgcta tgtcgattac ttcctgccga tcgttgccga tgcggaagcc | 480 |
| ggttttggcg gtgtcctgaa tgcctttgaa ctgatgaaag cgatgattga agccggtgca | 540 |
| gcggcagttc acttcgaaga tcagctggcg tcagtgaaga atgcggtca catgggcggc | 600 |
| aaagttttag tgccaactca ggaagctatt cagaaactgg tcgcggcgcg tctggcagct | 660 |
| gacgtgacgg gcgttccaac cctgctggtt gcccgtaccg atgctgatgc ggcggatctg | 720 |
| atcacctccg attgcgaccc gtatgacagc gaatttatta ccggcgagcg taccagtgaa | 780 |
| ggcttcttcc gtactcatgc gggcattgag caagcgatca gccgtggcct ggcgtatgcg | 840 |
| ccatatgctg aactggtctg tgtgaaaccc tccacgccgg atctggaact ggcgcgtcgc | 900 |
| tttgcacaag ctatccacgc gaaatatccg gcaaactgc tggcttataa ctgctcgccg | 960 |
| tcgttcaact ggcagaaaaa cctcgacgac aaaactattg ccagcttcca gcagcagctg | 1020 |
| tcggatatgg gctacaagtt ccagttcatc accctggcag gtatccacag catgtggttc | 1080 |
| aacatgtttg acctggcaaa cgcctatgcc cagggcgagg gtatgaagca ctacgttgag | 1140 |
| aaagtgcagc agccggaatt tgccgccgcg aaagatggct ataccttcgt atctcaccag | 1200 |
| caggaagtgg gtacaggtta cttcgataaa gtgacgacta ttattcaggg cggcacgtct | 1260 |
| tcagtcaccg cgctgaccgg ctccactgaa gaatcgcagt tctaa | 1305 |

```
<210> SEQ ID NO 46
<211> LENGTH: 434
<212> TYPE: PRT
<213> ORGANISM: Artificial sequence
<220> FEATURE:
<223> OTHER INFORMATION: synthetic peptide

<400> SEQUENCE: 46

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365
```

Tyr Ala Gln Gly Glu Gly Met Lys His Tyr Val Glu Lys Val Gln Gln
        370                 375                 380

Pro Glu Phe Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
                420                 425                 430

Gln Phe

<210> SEQ ID NO 47
<211> LENGTH: 1191
<212> TYPE: DNA
<213> ORGANISM: Artificial sequence
<220> FEATURE:
<223> OTHER INFORMATION: synthetic nucleotide

<400> SEQUENCE: 47

| | |
|---|---|
| atgtttgaga acattaccgc cgctcctgcc gacccgattc tgggcctggc cgatctgttt | 60 |
| cgtgccgatg aacgtcccgg caaaattaac ctcgggattg tgtctataa agatgagacg | 120 |
| ggcaaaaccc cggtactgac cagcgtgaaa aaggctgaac agtatctgct cgaaaatgaa | 180 |
| accaccaaaa attacctcgg cattgacggc atccctgaat tggtcgctg cactcaggaa | 240 |
| ctgctgtttg gtaaaggtag cgccctgatc aatgacaaac gtgctcgcac ggcacagact | 300 |
| ccgggggggca ctggcgcact acgcgtggct gccgatttcc tggcaaaaaa taccagcgtt | 360 |
| aagcgtgtgt gggtgagcaa cccaagctgg ccgaaccata gagcgtctt taactctgca | 420 |
| ggtctggaag ttcgtgaata cgcttattat gatgcggaaa atcacactct tgacttcgat | 480 |
| gcactgatta cagcctgaa tgaagctcag gctggcacg tagtgctgtt ccatggctgc | 540 |
| tgccataacc caaccggtat cgaccctacg ctggaacaat ggcaaacact ggcacaactc | 600 |
| tccgttgaga aaggctggtt accgctgttt gacttcgctt accagggttt tgcccgtggt | 660 |
| ctggaagaag atgctgaagg actgcgcgct tcgcggcta tgcataaaga gctgattgtt | 720 |
| gccagttcct actctaaaaa ctttggcctg tacaacgagc gtgttggcgc ttgtactctg | 780 |
| gttgctgccg acagtgaaac cgttgatcgc gcattcagcc aaatgaaagc ggcgattcgc | 840 |
| gctaactact ctaacccacc agcacacggc gcttctgttg ttgccaccat cctgagcaac | 900 |
| gatgcgttac gtgcgatttg ggaacaagag ctgactgata tgcgccagcg tattcagcgt | 960 |
| atgcgtcagt tgttcgtcaa tacgctgcag gaaaaaggcg caaaccgcga cttcagcttt | 1020 |
| atcatcaaac agaacggcat gttctccttc agtggcctga caaagaaca agtgctgcgt | 1080 |
| ctgcgcgaag agtttggcgt atatgcggtt gcttctggtc gcgtaaatgt ggccgggatg | 1140 |
| acaccagata acatggctcc gctgtgcgaa gcgattgtgg cagtgctgta a | 1191 |

<210> SEQ ID NO 48
<211> LENGTH: 396
<212> TYPE: PRT
<213> ORGANISM: Artificial sequence
<220> FEATURE:
<223> OTHER INFORMATION: synthetic peptide

<400> SEQUENCE: 48

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
                20                  25                  30

Ile Gly Val Tyr Lys Asp Glu Thr Gly Lys Thr Pro Val Leu Thr Ser
         35                  40                  45

Val Lys Lys Ala Glu Gln Tyr Leu Leu Glu Asn Glu Thr Thr Lys Asn
 50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                 85                  90                  95

Thr Ala Gln Thr Pro Gly Gly Thr Gly Ala Leu Arg Val Ala Ala Asp
                100                 105                 110

Phe Leu Ala Lys Asn Thr Ser Val Lys Arg Val Trp Val Ser Asn Pro
                115                 120                 125

Ser Trp Pro Asn His Lys Ser Val Phe Asn Ser Ala Gly Leu Glu Val
                130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
                180                 185                 190

Gln Trp Gln Thr Leu Ala Gln Leu Ser Val Glu Lys Gly Trp Leu Pro
                195                 200                 205

Leu Phe Asp Phe Ala Tyr Gln Gly Phe Ala Arg Gly Leu Glu Glu Asp
                210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
                260                 265                 270

Ser Gln Met Lys Ala Ala Ile Arg Ala Asn Tyr Ser Asn Pro Pro Ala
                275                 280                 285

His Gly Ala Ser Val Val Ala Thr Ile Leu Ser Asn Asp Ala Leu Arg
                290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
                340                 345                 350

Leu Thr Lys Glu Gln Val Leu Arg Leu Arg Glu Glu Phe Gly Val Tyr
                355                 360                 365

Ala Val Ala Ser Gly Arg Val Asn Val Ala Gly Met Thr Pro Asp Asn
                370                 375                 380

Met Ala Pro Leu Cys Glu Ala Ile Val Ala Val Leu
385                 390                 395

<210> SEQ ID NO 49
<211> LENGTH: 1358
<212> TYPE: DNA
<213> ORGANISM: Artificial sequence
<220> FEATURE:
<223> OTHER INFORMATION: synthetic nucleotide

<400> SEQUENCE: 49

-continued

```
caggaggaat taacatggat cagacatatt ctctggagtc attcctcaac catgtccaaa    60
agcgcgaccc gaatcaaacc gagttcgcgc aagccgttcg tgaagtaatg accacactct   120
ggccttttct tgaacaaaat ccaaaatatc gccagatgtc attactggag cgtctggttg   180
aaccggagcg cgtgatccag tttcgcgtgg tatgggttga tgatcgcaac cagatacagg   240
tcaaccgtgc atggcgtgtg cagttcagct ctgccatcgg cccgtacaaa ggcggtatgc   300
gcttccatcc gtcagttaac cttcccattc tcaaattcct cggctttgaa caaaccttca   360
aaaatgccct gactactctg ccgatgggcg gtggtaaagg cggcagcgat ttcgatccga   420
aaggaaaaag cgaaggtgaa gtgatgcgtt tttgccaggc gctgatgact gaactgtatc   480
gccacctggg cgcggatacc gacgttccgg caggtgatat cggggttggt ggtcgtgaag   540
tcggctttat ggcggggatg atgaaaaagc tctccaacaa taccgcctgc gtcttcaccg   600
gtaagggcct ttcatttggc ggcagtctta ttcgcccgga agctaccggc tacggtctgg   660
tttatttcac agaagcaatg ctaaaacgcc acggtatggg ttttgaaggg atgcgcgttt   720
ccgtttctgg ctccggcaac gtcgcccagt acgctatcga aaaagcgatg gaatttggtg   780
ctcgtgtgat cactgcgtca gactccagcg gcactgtagt tgatgaaagc ggattcacga   840
aagagaaact ggcacgtctt atcgaaatca agccagccg cgatggtcga gtggcagatt   900
acgccaaaga atttggtctg gtctatctcg aaggccaaca gccgtggtct ctaccggttg   960
atatcgccct gccttgcgcc acccagaatg aactggatgt tgacgccgcg catcagctta  1020
tcgctaatgg cgttaaagcc gtcgccgaag gggcaaatat gccgaccacc atcgaagcga  1080
ctgaactgtt ccagcaggca ggcgtactat ttgcaccggg taaagcggct aatgctggtg  1140
gcgtcgctac atcgggcctg gaaatggcac aaaacgctgc cgcctgggc tggaaagccg  1200
agaaagttga cgcacgtttg catcacatca tgctggatat ccaccatgcc tgtgttgagc  1260
atggtggtga aggtgagcaa accaactacg tgcagggcgc gaacattgcc ggttttgtga  1320
aggttgccga tgcgatgctg gcgcagggtg tgatttaa                          1358
```

<210> SEQ ID NO 50  
<211> LENGTH: 447  
<212> TYPE: PRT  
<213> ORGANISM: Artificial sequence  
<220> FEATURE:  
<223> OTHER INFORMATION: synthetic peptide

<400> SEQUENCE: 50

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
```

```
            115                 120                 125
Gly Gly Ser Asp Phe Asp Pro Lys Gly Lys Ser Glu Gly Glu Val Met
            130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
            195                 200                 205

Glu Ala Thr Gly Tyr Gly Leu Val Tyr Phe Thr Glu Ala Met Leu Lys
            210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
            275                 280                 285

Arg Asp Gly Arg Val Ala Asp Tyr Ala Lys Glu Phe Gly Leu Val Tyr
290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
            355                 360                 365

Gly Lys Ala Ala Asn Ala Gly Gly Val Ala Thr Ser Gly Leu Glu Met
            370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
            435                 440                 445

<210> SEQ ID NO 51
<211> LENGTH: 1543
<212> TYPE: DNA
<213> ORGANISM: Artificial sequence
<220> FEATURE:
<223> OTHER INFORMATION: synthetic nucleotide

<400> SEQUENCE: 51
atgccagcaa ccggtgagga tcaggatctg gtgcaggacc taattgaaga gccagcgaca      60
ttcagtgatg cagtactgtc tagcgacgaa gaattgttcc accagaaatg tccgaaaccg     120
gctccgattt actctccggt atccaaacca gtgtcttttg aaagcctgcc gaaccgtcgc     180
ctgcatgaag aatttctgcg cagctctgtg gacgttttgt tgcaggaagc cgtgttcgaa     240
```

```
ggtaccaacc gtaaaaaccg tgtgttacag tggcgtgaac cggaagaact gcgccgtcta    300
atggatttcg gtgttcgttc tgctccgtca actcacgaag agctgctgga ggtgctgaag    360
aaagttgtca cctactccgt gaaaacgggt caccccttatt tcgtaaacca gctgttcagt   420
gcggtggacc gtatggcct ggttgccaa tgggcaaccg atgccctgaa cccatccgtt     480
tatacctatg aagtgtctcc ggtgttcgta ctgatggaag aggtggttct gcgcgaaatg    540
cgtgcgatcg ttggttttga gggcggaaaa ggtgatggta tcttctgccc aggcggttct    600
attgccaacg gttacgcaat cagctgcgct cgttaccgtt tcatgccgga catcaagaaa    660
aagggcctgc attctctgcc gcgtctggtc ctgtttacct ccgaggacgc tcattacagc    720
attaagaaac tggcgtcctt ccagggtatc ggcacggata acgtgtatct catccgtacc    780
gatgcgcgtg tcgtatgga cgtgtcccat ctcgttgagg aaatcgaacg ttctctgcgt    840
gaaggcgcag ctccattcat ggtctcggct actgccggta ctactgttat cggtgctttc    900
gacccgatca aaaaaatcgc ggatgtatgt cagaaataca aactctggtt gcacgtagac    960
gcagcgtggg gtggcggtgc actggtgagc gcaaagcatc gtcacctgct gaaaggtatc   1020
gaacgtgccg actccgttac atggaacccg cacaaactgc ttaccgcacc gcagcagtgc   1080
agcactctgc tgttgcgtca cgaaggcgtg ctggcagaag cacactctac taacgcagca   1140
tatctgttcc agaaggacaa gttctacgat accaagtatg acactggcga taaacacatc   1200
cagtgtggtc gccgtgcaga cgttctgaaa ttctggttca tgtggaaagc aaaaggtact   1260
tctggactgg aaaacacgt tgacaaagtt ttcgaaaatg cacgtttctt caccgattgc   1320
atcaaaaacc gtgaaggctt tgaaatggtg atcgcggagc cggaatatac caacatttgc   1380
ttctggtacg tgccgaaatc tctgcgtggc cgtaaagatg aagcagacta caaagataaa   1440
ctccacaaag tagcaccgcg tattaaagaa cgtatgatga agaaggttc tatgatggtt    1500 acctaccagg cacagaaagg ccatccgaac ttcttccgca tcg                    1543
```

<210> SEQ ID NO 52
<211> LENGTH: 514
<212> TYPE: PRT
<213> ORGANISM: Artificial sequence
<220> FEATURE:
<223> OTHER INFORMATION: synthetic peptide

<400> SEQUENCE: 52

```
Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
            20                  25                  30

Phe His Gln Lys Cys Pro Lys Pro Ala Pro Ile Tyr Ser Pro Val Ser
        35                  40                  45

Lys Pro Val Ser Phe Glu Ser Leu Pro Asn Arg Arg Leu His Glu Glu
    50                  55                  60

Phe Leu Arg Ser Ser Val Asp Val Leu Leu Gln Glu Ala Val Phe Glu
65                  70                  75                  80

Gly Thr Asn Arg Lys Asn Arg Val Leu Gln Trp Arg Glu Pro Glu Glu
                85                  90                  95

Leu Arg Arg Leu Met Asp Phe Gly Val Arg Ser Ala Pro Ser Thr His
            100                 105                 110

Glu Glu Leu Leu Glu Val Leu Lys Lys Val Val Thr Tyr Ser Val Lys
        115                 120                 125
```

```
Thr Gly His Pro Tyr Phe Val Asn Gln Leu Phe Ser Ala Val Asp Pro
        130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Gly Lys Gly Asp
                180                 185                 190

Gly Ile Phe Cys Pro Gly Gly Ser Ile Ala Asn Gly Tyr Ala Ile Ser
            195                 200                 205

Cys Ala Arg Tyr Arg Phe Met Pro Asp Ile Lys Lys Lys Gly Leu His
210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255

Leu Ile Arg Thr Asp Ala Arg Gly Arg Met Asp Val Ser His Leu Val
                260                 265                 270

Glu Glu Ile Glu Arg Ser Leu Arg Glu Gly Ala Ala Pro Phe Met Val
            275                 280                 285

Ser Ala Thr Ala Gly Thr Thr Val Ile Gly Ala Phe Asp Pro Ile Glu
        290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
                340                 345                 350

Leu Leu Thr Ala Pro Gln Gln Cys Ser Thr Leu Leu Leu Arg His Glu
            355                 360                 365

Gly Val Leu Ala Glu Ala His Ser Thr Asn Ala Ala Tyr Leu Phe Gln
370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
                420                 425                 430

Asn Ala Arg Phe Phe Thr Asp Cys Ile Lys Asn Arg Glu Gly Phe Glu
            435                 440                 445

Met Val Ile Ala Glu Pro Glu Tyr Thr Asn Ile Cys Phe Trp Tyr Val
450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495

Ser Met Met Val Thr Tyr Gln Ala Gln Lys Gly His Pro Asn Phe Phe
            500                 505                 510

Arg Ile
```